United States Patent
Thor et al.

(10) Patent No.: US 11,872,151 B2
(45) Date of Patent: Jan. 16, 2024

(54) METHOD OF MANUFACTURING AN ANKLE FOOT ORTHOSIS

(71) Applicant: AST DESIGN LLC, Coronado, CA (US)

(72) Inventors: Arni Thor, Coronado, CA (US); Efrain Navarrete, Perris, CA (US)

(73) Assignee: AST Design, LLC, Coronado, CA (US)

( * ) Notice: Subject to any disclaimer, the term of this patent is extended or adjusted under 35 U.S.C. 154(b) by 515 days.

(21) Appl. No.: 16/997,925

(22) Filed: Aug. 19, 2020

(65) Prior Publication Data

US 2020/0375776 A1 Dec. 3, 2020

Related U.S. Application Data

(63) Continuation-in-part of application No. 15/977,880, filed on May 11, 2018, now Pat. No. 11,484,426.

(60) Provisional application No. 63/059,580, filed on Jul. 31, 2020, provisional application No. 62/990,726, filed on Mar. 17, 2020, provisional application No. 62/980,743, filed on Feb. 24, 2020, provisional application No. 62/889,720, filed on Aug. 21, 2019, (Continued)

(51) Int. Cl.
*A61F 5/01* (2006.01)
*A61F 5/14* (2022.01)

(52) U.S. Cl.
CPC ........... *A61F 5/0113* (2013.01); *A61F 5/0111* (2013.01); *A61F 5/14* (2013.01)

(58) Field of Classification Search
CPC ........ A61F 5/01; A61F 5/0102; A61F 5/0104; A61F 5/0111; A61F 5/0113; A61F 5/0127; A61F 5/14
See application file for complete search history.

(56) References Cited

U.S. PATENT DOCUMENTS

| 2,949,111 A | 8/1960 | Ruotoistenmaki |
| 4,646,726 A | 3/1987 | Westin et al. |

(Continued)

FOREIGN PATENT DOCUMENTS

| DE | 29704669 | 5/1997 |
| DE | 19941368 | 4/2001 |

(Continued)

OTHER PUBLICATIONS

Written Opinion of the International Searching Authority for PCT/US2020/047228 dated Dec. 2, 2020.

*Primary Examiner* — Keri J Nelson
(74) *Attorney, Agent, or Firm* — Garson & Gutierrez, PC

(57) ABSTRACT

Ankle foot orthoses and methods of manufacturing an ankle foot orthosis. In one embodiment, an ankle foot orthosis is disclosed that includes a foot plate constructed to have both a trimmable portion and a non-trimmable portion. The ankle foot orthosis includes a spiral strut coupled with either the hindfoot region of the foot plate laterally of a mid-line for the foot plate or the midfoot region of the foot plate laterally of the mid-line. The spiral strut includes a transition portion that spirals by approximately sixty-five degrees (65°) over less than one-hundred sixty millimeters (160 mm) in height from the bottom surface of the foot plate. The spiral strut also includes an adjustable portion that enables a cuff coupled thereto to be height adjustable. Methods of manufacturing the aforementioned ankle foot orthoses are also disclosed.

20 Claims, 46 Drawing Sheets

Related U.S. Application Data provisional application No. 62/625,893, filed on Feb. 2, 2018, provisional application No. 62/505,740, filed on May 12, 2017.

(56) References Cited

U.S. PATENT DOCUMENTS

| | | | |
|---|---|---|---|
| 5,776,090 | A | 7/1998 | Bergmann et al. |
| 5,817,041 | A | 10/1998 | Bader |
| 5,897,515 | A | 4/1999 | Willner et al. |
| 6,110,135 | A | 8/2000 | Madow et al. |
| 6,146,344 | A | 11/2000 | Bader |
| 6,146,349 | A | 11/2000 | Rothschild et al. |
| 6,676,618 | B2 | 1/2004 | Andersen |
| 6,945,947 | B2 | 9/2005 | Ingimundarson et al. |
| 7,077,818 | B2 | 7/2006 | Ingimundarson et al. |
| 7,266,910 | B2 | 9/2007 | Ingimundarson |
| 7,270,644 | B2 | 9/2007 | Ingimundarson |
| 7,354,413 | B2 | 4/2008 | Fisher |
| 7,513,880 | B2 | 4/2009 | Ingimundarson et al. |
| 7,749,423 | B2 | 7/2010 | Bader |
| 7,753,864 | B2 | 7/2010 | Beckwith et al. |
| 7,766,851 | B2 | 8/2010 | Lindh et al. |
| 8,021,316 | B2 | 9/2011 | Franke et al. |
| 8,323,224 | B2 | 12/2012 | Shlomovitz |
| 8,403,872 | B2 | 3/2013 | Franke et al. |
| 8,540,655 | B2 | 9/2013 | Franke et al. |
| 9,121,673 | B2 | 9/2015 | Popovici |
| 9,192,504 | B2 | 11/2015 | Andrews et al. |
| 9,211,208 | B2 | 12/2015 | Blum et al. |
| 9,326,880 | B2 | 5/2016 | Szczepanski |
| 9,433,522 | B2 | 9/2016 | Bader |
| 9,526,651 | B2 | 12/2016 | Kozasa et al. |
| 9,562,742 | B2 | 2/2017 | Popovici |
| 9,855,161 | B1 | 1/2018 | Bonaroti |
| 9,889,035 | B2 | 2/2018 | Jordan et al. |
| 9,901,475 | B2 | 2/2018 | Jordan et al. |
| 9,980,847 | B2 | 5/2018 | Andrews et al. |
| 10,052,221 | B2 | 8/2018 | Albertsson et al. |
| 10,105,252 | B2 | 10/2018 | Bader |
| 10,561,514 | B2 | 2/2020 | Romo et al. |
| 2004/0102727 | A1 | 5/2004 | Smits |
| 2005/0234378 | A1 | 10/2005 | Ingimundarson et al. |
| 2007/0038169 | A1 | 2/2007 | Alon et al. |
| 2007/0073202 | A1 | 3/2007 | Bader |
| 2007/0100268 | A1 | 5/2007 | Fisher |
| 2008/0077066 | A1 | 3/2008 | Lewis |
| 2008/0300525 | A1 | 12/2008 | Shlomovitz |
| 2009/0247920 | A1 | 10/2009 | Clements et al. |
| 2009/0287128 | A1 | 11/2009 | Ingimundarson et al. |
| 2011/0028877 | A1 | 2/2011 | Vollbrecht et al. |
| 2013/0072841 | A1 | 3/2013 | Bader |
| 2013/0131569 | A1 | 5/2013 | Blum et al. |
| 2014/0276318 | A1 | 9/2014 | Faux |
| 2014/0276320 | A1 | 9/2014 | Faux et al. |
| 2014/0378881 | A1 | 12/2014 | Wagner |
| 2015/0065934 | A1 | 3/2015 | Bader |
| 2015/0119781 | A1 | 4/2015 | Ponce |
| 2015/0148725 | A1 | 5/2015 | Johnsson et al. |
| 2015/0150709 | A1 | 6/2015 | Ljubimir et al. |
| 2015/0265450 | A1 | 9/2015 | Rodgers |
| 2015/0320581 | A1 | 11/2015 | Causse |
| 2016/0074199 | A1 | 3/2016 | Bader |
| 2016/0213552 | A1 | 7/2016 | Lindsay |
| 2016/0220406 | A1 | 8/2016 | Bader |
| 2017/0165094 | A1 | 6/2017 | Voskuilen et al. |
| 2017/0165095 | A1 | 6/2017 | Romo et al. |
| 2017/0196720 | A1* | 7/2017 | Hassel ............. A61F 5/0113 |
| 2017/0216071 | A1 | 8/2017 | Bader |
| 2017/0348132 | A1 | 12/2017 | Cooney |
| 2018/0333285 | A1 | 11/2018 | Thor et al. |

FOREIGN PATENT DOCUMENTS

| | | |
|---|---|---|
| DE | 102013019079 | 5/2015 |
| DE | 202016100379 | 5/2017 |
| EP | 0270661 | 6/1987 |
| EP | 2932944 | 10/2015 |
| EP | 3301680 | 9/2017 |
| FR | 2993452 | 1/2014 |
| GB | 2375962 | 12/2002 |
| GB | 25355612 | 8/2016 |
| GB | 2556317 | 5/2018 |
| GB | 2571963 | 9/2019 |
| GB | 2571965 | 9/2019 |
| RU | 2277394 | 6/2006 |
| WO | 1998034572 | 8/1998 |
| WO | 2001034071 | 5/2001 |
| WO | 2004066890 | 8/2004 |
| WO | 2008001394 | 1/2008 |
| WO | 2009139019 | 11/2009 |
| WO | 2011029837 | 3/2011 |
| WO | 2014001793 | 1/2014 |
| WO | 2017103621 | 6/2017 |
| WO | 2017134429 | 8/2017 |
| WO | 2017207532 | 12/2017 |
| WO | 2017212242 | 12/2017 |
| WO | 2019101602 | 5/2019 |
| WO | 2019175589 | 9/2019 |
| WO | 2019175592 | 9/2019 |

* cited by examiner $\Sigma F_x = 0 \quad F\cos 45 = R_x$
$\Sigma F_y = 0 \quad F\sin 45 + R_y = W + F - F_L$
$\Sigma M_A = 0 \quad F(s\sqrt{2}) + F_L(s) = F(s) + W(\frac{s}{2})$ For $F_L = 0$ (Assuming enough force to lift foot)

$F(s\sqrt{2} - s) = W(\frac{s}{2})$ $F = 1.21 W$ $\Sigma F_x = 0 \quad F\cos 4s = R_x$
$\Sigma F_y = 0 \quad F\sin 4s + R_y = W$
$\Sigma M_A = 0 \quad F(s\sqrt{2}) = W(\frac{s}{2})$ $\therefore F = .35 W$

METHOD OF MANUFACTURING AN ANKLE FOOT ORTHOSIS

PRIORITY

This application claims the benefit or priority to co-owned U.S. Provisional Patent Application Ser. No. 63/059,580 filed Jul. 31, 2020 entitled "Methods and Apparatus for Human Anatomical Orthoses", U.S. Provisional Patent Application Ser. No. 62/990,726 filed Mar. 17, 2020 of the same title, U.S. Provisional Patent Application Ser. No. 62/980,743 filed Feb. 24, 2020 of the same title and U.S. Provisional Patent Application Ser. No. 62/889,720 filed Aug. 21, 2019 of the same title, the contents of each of the foregoing being incorporated herein by reference in its entirety.

This application also claims the benefit of priority to, and is a continuation-in-part of, co-owned and co-pending U.S. patent application Ser. No. 15/977,880 filed May 11, 2018 of the same title, which claims the benefit of priority to both of co-owned U.S. Provisional Patent Application Ser. No. 62/505,740 filed May 12, 2017 of the same title and U.S. Provisional Patent Application Ser. No. 62/625,893 filed Feb. 2, 2018 of the same title, the contents of each of the foregoing being incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE DISCLOSURE

Field of the Disclosure

The present disclosure relates generally to the field of the correction of disorders of the lower limbs by use of braces and other devices to correct alignment or provide support and in one exemplary aspect, to ankle foot orthoses and methods for manufacturing and using the same.

Description of Related Art

Drop foot is a common medical condition that has its source in various different pathological conditions. The condition may be caused by trauma in which the peroneal nerve that innervates the peroneal muscles becomes damaged. Drop foot may also be present following a stroke, or because of various disorders such as multiple sclerosis (MS) and amyotrophic lateral sclerosis (ALS), or after injury. Many orthotic treatments exist for the treatment of drop foot including, for example: rigid ankle foot orthoses (AFOs); semi-rigid foot orthoses; soft AFOs (such as "Foot Up"-type devices or a soft ankle brace with straps); and functional electrical stimulation systems. For example, carbon fiber AFOs are known for their lightweight and low-profile nature making them easier to fit into a shoe as compared with non-carbon fiber AFOs that are manufactured from fabric and/or plastic.

Existing AFO devices are designed to address deficiencies, such as the aforementioned drop foot condition, by controlling dorsiflexion or plantar flexion of a wearer's foot. However, many patients also have additional underlying conditions such as, for example, valgus or varus deformities and instability associated with their ankle and/or knees which existing OTS AFO solutions do not address well.

Moreover, various anatomical differences between patients as well as varying degrees of severity for their conditions leads to a large number of size and stiffness options for these AFO devices in order to properly address any given patient's specific medical condition. For example, most AFO devices come in extra-small, small, medium, large, and extra-large sizes. In addition to these varying sizes, AFO devices may also come in a variety of different stiffnesses such as, for example, light stiffness, standard stiffness, and maximum stiffness. Moreover, a given patient may have this condition in either (or both) of their left or right leg. Accordingly, for a treating physician to properly address a particular patient's condition, the treating physician may be required to stock thirty (30) or more different AFO devices in order to effectively handle any given patient's needs. However, due to AFO device costs, as well as limited inventory space, physicians typically only stock a limited subset of all available AFO device options resulting in sub-optimal treatment outcomes for their patients.

Accordingly, despite the wide variety of the foregoing solutions, there remains a salient need for an orthotic device that addresses the foregoing problems by: providing adequate support for everyday use dependent upon a given patient's medical condition; is comfortable to wear; is inexpensive to stock within a given treating physician's place of business; is easy to put on and take off by the wearer; and can be easily adjusted throughout the day by either the patient or practitioner in order to provide an appropriate amount of support dependent upon the activity level required of the user.

SUMMARY

The present disclosure satisfies the foregoing needs by providing, inter alia, an orthoses apparatus for addressing some or all of the foregoing deficiencies as well as methods of their manufacture and methods of their use.

In one aspect, an ankle foot orthosis (AFO) is disclosed. In one embodiment, the AFO includes a foot plate having a trimmable portion and a non-trimmable portion; a spiral strut coupled with a hindfoot region of the foot plate laterally of a mid-line of the foot plate at an interface region, the spiral strut including a transition portion that spirals approximately sixty-five degrees (65°) over less than one-hundred sixty millimeters (160 mm) in height from a bottom surface of the foot plate, the spiral strut further including an adjustable portion; and a cuff that is height adjustable over the adjustable portion of the spiral strut.

In one variant, the trimmable portion of the foot plate is located in both a hindfoot region of the foot plate as well as portions anterior to the hindfoot region of the foot plate.

In another variant, at least a portion of the trimmable portion located in the hindfoot region of the foot plate is located posterior from the interface region between the spiral strut and the foot plate.

In yet another variant, the transition portion of the spiral strut includes a curved surface adjacent to the foot plate that transitions towards a flat surface adjacent to the adjustable portion of the spiral strut.

In yet another variant, the curved surface adjacent to the foot plate includes at least two differing radial dimensions in a plane that are parallel with a top surface of the footplate.

In yet another variant, the trimmable portion of the foot plate shares a common surface with the non-trimmable portion of the foot plate and the non-trimmable portion of the foot plate extends below the trimmable portion of the foot plate. A concaved junction is disposed on at least a portion of an interface between the trimmable portion and the non-trimmable portion.

In yet another variant, the cuff that is height adjustable over the adjustable portion of the spiral strut enables the overall height of the AFO to vary between three hundred and twenty millimeters (320 mm) and three hundred and sixty-five millimeters (365 mm).

In yet another variant, the cuff that is height adjustable over the adjustable portion of the spiral strut enables the overall height of the AFO to vary between two hundred and ninety-five millimeters (295 mm) and three hundred and eighty-four millimeters (384 mm).

In another embodiment, the AFO includes a foot plate having a trimmable portion and a non-trimmable portion; a spiral strut coupled with a mid-foot region of the foot plate lateral of a mid-line of the foot plate at an interface region, the spiral strut including a transition portion that spirals approximately ninety degrees (90°) over less than one-hundred sixty millimeters (160 mm) in height, the spiral strut further including an adjustable portion; and a cuff that is height adjustable over the adjustable portion of the spiral strut.

In one variant, the trimmable portion of the foot plate is located in both a hindfoot region of the foot plate as well as portions anterior to the hindfoot region of the foot plate.

In another variant, the trimmable portion located in the hindfoot region of the foot plate enables an overall length of the foot plate to be trimmed by greater than fifteen millimeters (15 mm).

In yet another variant, the trimmable portion of the foot plate enables an overall length of the foot plate to be trimmed by greater than seventy-five millimeters (75 mm).

In yet another variant, the trimmable portion of the foot plate shares a common surface with the non-trimmable portion of the foot plate and the non-trimmable portion of the foot plate extends below the trimmable portion of the foot plate. A concaved junction is disposed on at least a portion of an interface between the trimmable portion and the non-trimmable portion.

In yet another variant, the transition portion of the spiral strut includes a curved surface that transitions towards a flat surface adjacent to the adjustable portion of the spiral strut.

In yet another variant, the adjustable portion of the spiral strut includes the flat surface, the flat surface enabling an overall height of the AFO to vary between three hundred and seventy-five millimeters (375 mm) and four hundred and thirteen millimeters (413 mm).

In yet another variant, the flat surface of the adjustable portion of the spiral strut enables an overall height of the AFO to vary between three hundred and sixty millimeters (360 mm) and four hundred and thirty-two millimeters (432 mm).

In yet another embodiment, the ankle foot orthoses includes a calf piece with a lockable height adjustment on a strut that comes down the leg and connects to a footplate that is trimmable to size. The lockable height adjustment along with the footplate that is trimmable to size enable the ankle foot orthoses to be a one size fits all solution to patient's with various anatomical deficiencies associated with their lower leg. This requires a certain length of a completely vertical strut section which allows the calf piece to travel enough distance to cover all anthropometric sizes.

In one variant, the calf piece includes a rotary tensioning device that enables the calf piece to tighten around the wearer's anatomy.

In another variant, the calf piece may be moldable and trimmable to a wearer's anatomy to enhance the support that the ankle foot orthosis provides.

In yet another variant, the ankle foot orthoses further includes a support strap which connects to the footplate, crosses over the footplate so that it sits properly underneath the arch of the foot for support and is configured to spiral over the foot and up the leg of the wearer in one of multiple configurations and connect directly to the calf piece.

In yet another variant, the support strap may be constructed with an elastic-like material, may include portions that are less elastic than the elastic-like material, may include an integrated rotary tensioning mechanism.

In yet another variant a second support strap may be integrated which connects on top of the heel section of the footplate, crosses around the calcaneus, over the dorsum of the foot and anchors to the first support strap.

In yet another variant an insole is used to hold both straps down on the footplate to ensure that the straps do not move within the shoe.

In yet another variant the insole includes a heel cup/midfoot support so that in combination with the two straps provides ankle stability.

In yet another variant a supra malleolar orthotics (SMO) is provided with the AFO in combination with both straps for greater control.

In yet another variant the two straps are integrated into one knitted structure that captures the foot and heel.

In yet another variant, the calf piece may include one or more keyholes to assist with the donning and doffing of the ankle foot orthosis and may further include a locking ring to prevent the mechanism inserted into the keyhole from accidentally coming undone.

In yet another embodiment, an AFO is disclosed that consists of a footplate, a medial and lateral strut that connect in the back with an open heel that extends upwards to the calf section. In one variant, the AFO includes two struts that can accommodate all sizes with a slide feature to change the width of the footplate, a slide feature or trim ability to change the height of the AFO and a slide feature or trim ability to change the length and width of the footplate.

In yet another embodiment, an AFO is disclosed that can be universal in size with the footplate being trimmable to accommodate both left and right foot configurations.

In another aspect, a trimmable foot plate for use with the aforementioned ankle foot orthoses is disclosed.

In yet another aspect, a support strap for use with the aforementioned ankle foot orthoses is disclosed.

In yet another aspect a moldable or adjustable supero malleolus orthosis (SMO) is attached to the AFO.

In yet another aspect, an insole for use with the aforementioned ankle foot orthoses is disclosed.

In yet another aspect, a knitted supero malleolus orthosis for use with the aforementioned ankle foot orthoses is disclosed.

In one variant, the knitted supero malleolus orthoses is connected to both support straps.

In yet another aspect, a carbon orthosis is disclosed. In one embodiment, the carbon orthosis extends to the front of the tibia where the tibia shell can slide up and down on the carbon strut but can also telescope independently from the carbon strut, upwards to lengthen the contact area of the tibia shell.

In yet another aspect, a tibia shell is disclosed. In one embodiment, the tibia shell can be lengthened upwards by snapping a second shell onto the first shell where such shell may be heat formable and trimmable to accommodate each body shape.

In yet another aspect, methods of manufacturing the aforementioned AFO are disclosed. In one embodiment, the method includes acquiring a pre-impregnated carbon fiber sheet of material; cutting the pre-impregnated carbon fiber sheet of material to a desired shape; inserting the cut pre-impregnated carbon fiber sheet of material into a multi-piece mold, the multi-piece mold manufactured from a metallic material; compressing the multi-piece mold with the inserted and cut pre-impregnated carbon fiber sheet of material disposed therein; heating the multi-piece mold so as to activate resin within the cut pre-impregnated carbon fiber sheet of material; and removing the activated cut pre-impregnated carbon fiber sheet of material from the multi-piece mold.

In one variant, individual strands of the cut pre-impregnated carbon fiber sheet are greater than one hundred and twenty-six millimeters (126 mm) in length.

In another variant, individual strands of the cut pre-impregnated carbon fiber sheet are greater than one hundred and sixty millimeters (160 mm) in length.

In yet another variant, the multi-piece mold includes a cavity to form a transition portion and an adjustable portion of an ankle foot orthosis (AFO) strut and the method further includes placing the cut pre-impregnated carbon fiber sheet into the multi-piece mold such that the individual strands of the cut pre-impregnated carbon fiber sheet are present within each of the transition portion and the adjustable portion of the AFO strut as well as a foot plate portion of the AFO.

Other features and advantages of the present disclosure will immediately be recognized by persons of ordinary skill in the art with reference to the attached drawings and detailed description of exemplary implementations as given below.

BRIEF DESCRIPTION OF THE DRAWINGS

FIG. 1C is a side view of the exemplary strapping of FIG. 1A that has been integrated into a rigid or semi-rigid AFO, in accordance with the principles of the present disclosure.

FIG. 2I is a perspective view of an exemplary connection structure for use with the AFO of, for example, FIG. 2A, in accordance with the principles of the present disclosure.

FIGS. 3F-3J are various views of an exemplary posterior AFO device, in accordance with the principles of the present disclosure.

Figure 1A:
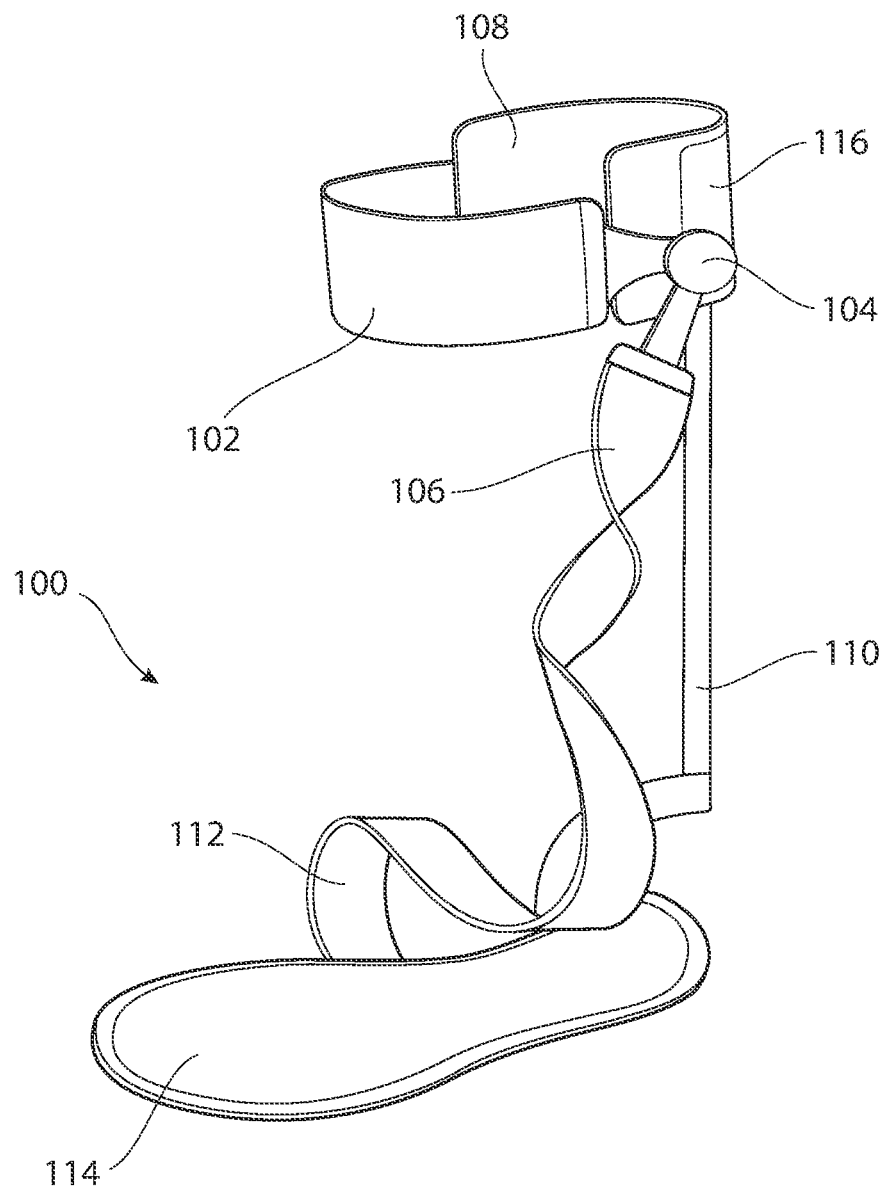
FIG. 1A is a perspective view of exemplary strapping that has been integrated into a rigid or semi-rigid AFO, in accordance with the principles of the present disclosure.

All Figures disclosed herein are © Copyright 2017-2020 AST Design, LLC. All rights reserved.

DETAILED DESCRIPTION

Implementations of the present technology will now be described in detail with reference to the drawings, which are provided as illustrative examples so as to enable those skilled in the art to practice the technology. Notably, the figures and examples below are not meant to limit the scope of the present disclosure to any single implementation or implementations, but other implementations are possible by way of interchange of, substitution of, or combination with some or all of the described or illustrated elements. Wherever convenient, the same reference numbers will be used throughout the drawings to refer to same or like parts.

In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention. Unless a contrary meaning is explicitly stated, all ranges are inclusive of their endpoints, and open-ended ranges are to be interpreted as bounded on the open end by commercially feasible embodiments.

Furthermore, while specific embodiments are illustrated and discussed, it would be readily apparent to one of ordinary skill given the contents of the present disclosure that various features illustrated and described within certain embodiments may be bodily incorporated into other disclosed embodiments. For example, various features disclosed within, for example, FIGS. 1A-1C may be readily incorporated into other disclosed variants including, for example, those variants shown with respect to FIGS. 2A-4B, and 6A-11 and vice versa. These and other variants would be readily apparent to one of ordinary skill given the contents of the present disclosure.

Figure 1B:
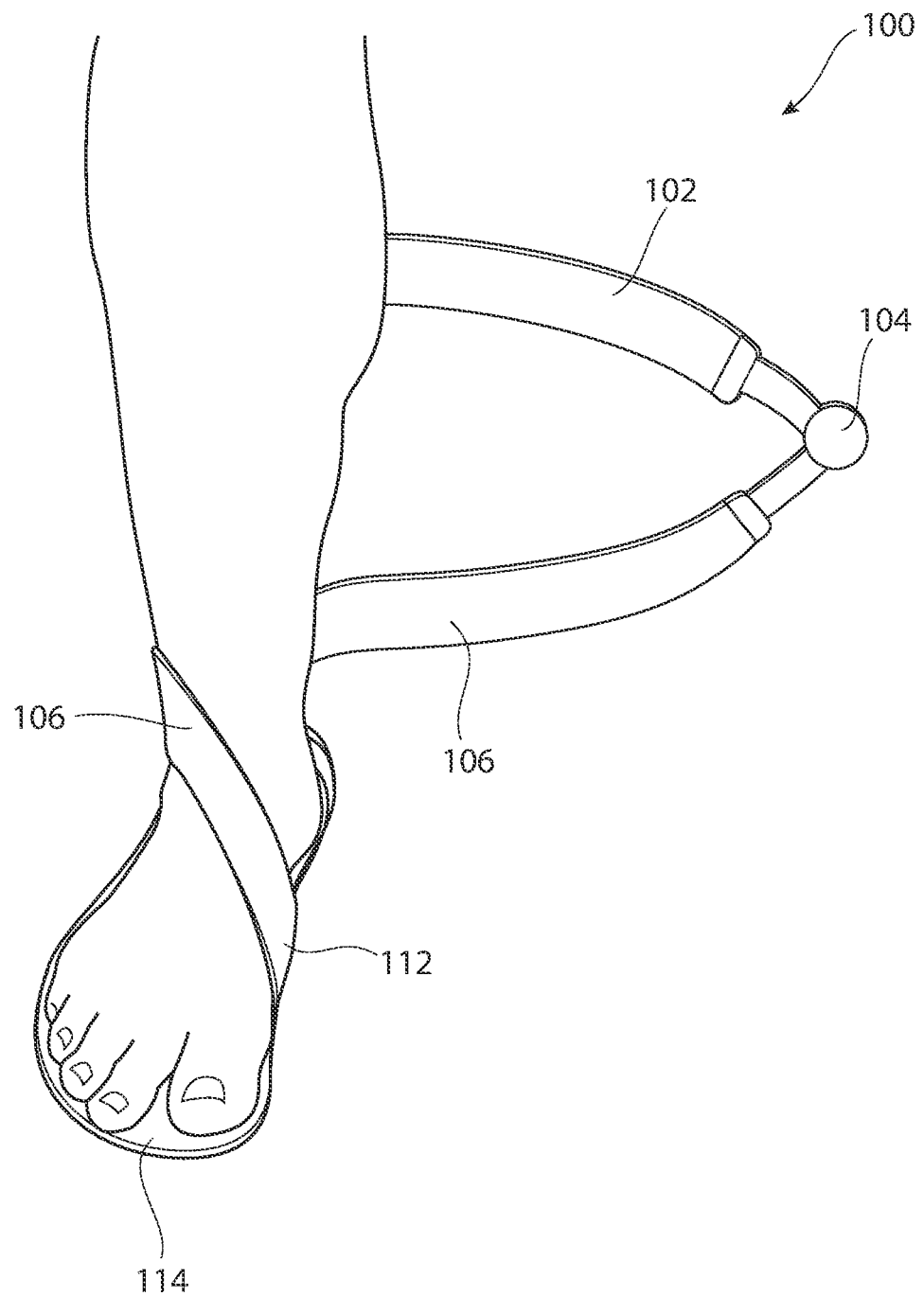
FIG. 1B is a front view of the exemplary strapping of FIG. 1A that has been integrated into a rigid or semi-rigid AFO, in accordance with the principles of the present disclosure.
Figure 1B:
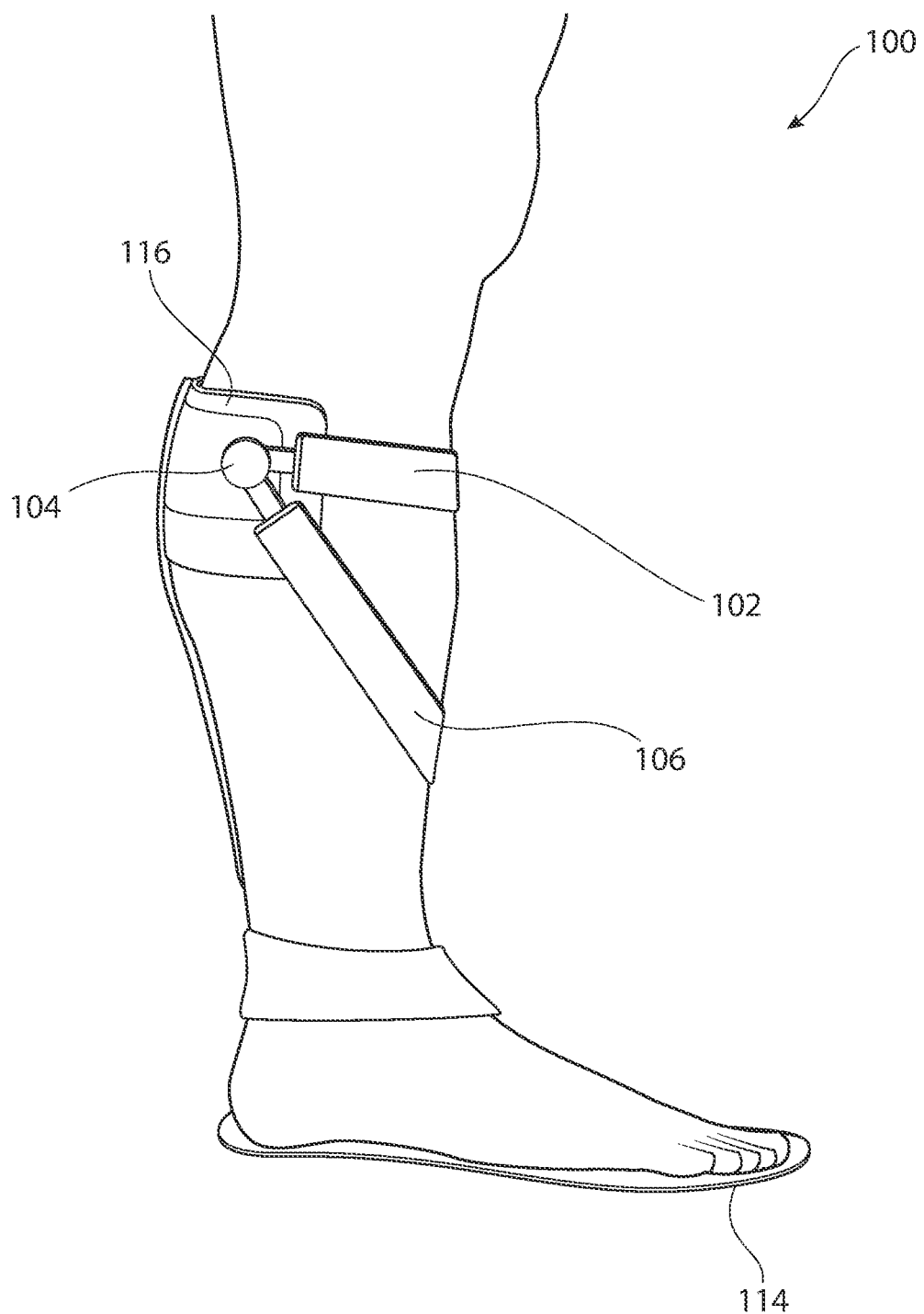

Referring now to FIGS. 1A-1C, one exemplary ankle foot orthosis (AFO) 100 is shown and described in detail. For example, FIG. 1A illustrates a rigid or semi-rigid AFO that includes a dynamic semi-flexible foot plate 114, a strut 110 (e.g., a so-called "spiral strut") that is configured to be disposed around the foot and ankle either medially, laterally, or posteriorly and run up along a user's calf muscle, and a supporting structure 108 that is configured to fit adjacent to a user's knee. In some implementations, supporting structure 108 may be manufactured from a heat-moldable plastic, metal, leather, a carbon composite material, or various combinations of the foregoing. Support strap 106 may be anchored on the medial side of the foot in region 112, and further be anchored to a rotary tensioning system 104. Orthosis 100 may further include an adjustable strap 102 which may be secured to anchoring fabric 116 that is disposed on the supporting structure 108.

Referring now to FIG. 1B, orthosis 100 is shown being put on (or taken off) the leg of a user. As can now more readily be seen, support strap 106 may be wrapped in, for example, a clockwise direction around the lower leg of the user where both adjustable strap 102 and support strap 106 are attached to a rotary tensioning system 104. Accordingly, when the rotary tensioning system 104 is secured to, for example, anchoring fabric (116, FIG. 1A), both the adjustable strap 102 and support strap 106 may be simultaneously placed under tension through adjustments made through the rotary tensioning system 104. Such simultaneous tensioning eases the donning and doffing of the orthosis 100 so that the device may be adjusted using a single hand. Such a configuration may be particularly advantageous for users that may have, for example, an impairment to one of their hands and/or arms as the orthosis 100 may be put on (or taken off) using one hand. In some implementations, two (or more)

rotary tensioning mechanisms 104 may be included with the orthosis 100. For example, one rotary tensioning mechanism 104 may assist with the tensioning of the adjustable strap 102, while another rotary tensioning mechanism 104 may assist with the tensioning of the support strap 106. In some implementations, the support strap 106 may be obviated altogether and hence, a single rotary tensioning mechanism 104 may assist with the tensioning of the adjustable strap 102.

FIG. 1C illustrates orthosis 100 after an appropriate amount of tension has been applied via rotary tensioning system 104. The orthosis 100 as shown in FIGS. 1A-1C may include carbon fiber in, for example, the strut 110 and/or the foot plate 114. Via inclusion of the support strap 106 (which may be elastic and/or inelastic in portions of the strap 106), an additional dorsiflexion (and/or plantar flexion) support is provided, as well as inversion/eversion (valgus/varus) support dependent upon the direction of rotation for the support strap 106 resulting in proper tibia alignment throughout the gait. Adding such a strap 106 onto the orthosis 100 may add increased complexity of donning, however when configured with a rotary tensioning system 104 (e.g., a BOA dial) that allows for two (or more) straps to be adjusted at the same time, one can provide a greater level of function to the orthosis 100 while simultaneously adding to the ease of donning and doffing (e.g., by enabling use of a single hand for donning and doffing).

While the support strap 106 is illustrated as coming up off the medial side of the foot (e.g., in FIGS. 1A and 1B) and spiraling around the tibia to the lateral side of the leg and around the back of leg, it would be readily appreciated by one of ordinary skill given the contents of the present disclosure that the support strap 106 may be positioned in other configurations. For example, the support strap 106 may start on the lateral side of the foot and spiral around the medial side of the leg in some implementations. In some implementations, orthosis 100 may include two (or more) support straps 106. For example, one support strap 106 may come up off the medial side of the foot and spiral around the lateral side of the leg, while another support strap 106 may come up off the lateral side of the foot and spiral around the medial side of the leg. Regardless of the configuration chosen, the support strap 106 may ultimately be secured to either the lateral or medial side of the leg, dependent upon the particular needs of the wearer. The support strap 106 may also attach underneath the foot plate 114 and spiral up on either the medial or lateral side of the foot. For example, support strap 106 may attach underneath the foot plate 114 on the lateral side of the foot, cross under the foot plate 114 and then cross up over the foot medially. Such a configuration is able to pick up the medial arch by spiraling across the lower leg and being anchored to the adjustable calf strap 102 on the lateral side of the calf.

The strapping system for orthosis 100 may be modified to control dorsiflexion, plantar flexion, as well as various varus and valgus deformities and/or other instabilities. For example, if the support strap 106 fully spirals around the leg of the wearer (see e.g., FIG. 1A), the support strap 106 will tighten in both plantar flexion as well as dorsiflexion, with a minimal amount of tension when the foot is in a relaxed position. However, if the support strap 106 does not fully spiral around the leg of the wearer (see e.g., FIG. 2G), the support strap 106 will tighten during plantar flexion and will loosen during dorsiflexion. These and other configurations can be readily modified dependent upon the needs of the wearer. For example, if the support strap 106 comes up medially on the foot and only stays in front of the leg, the support strap 106 is controlling a valgus condition and supporting plantar flexion. If the support strap 106 comes up laterally on the foot and only stays in front of the leg, the support strap 106 is controlling a varus condition and supporting plantar flexion. If the support strap 106 comes up medially on the foot and spirals around the leg so that it covers both the front and back of the leg, the support strap 106 is controlling a valgus condition as well as supporting both plantar flexion and dorsiflexion. If the support strap 106 comes up laterally on the foot and spirals around the leg so that it covers both the front and back of the leg, the support strap 106 is controlling a varus condition as well as supporting both plantar flexion and dorsiflexion.

In some implementations, the configurability of the support strap 106 is enabled by the inclusion of a plurality of attachment points located on the foot plate 114, as well as one or more attachment points located on the adjustable strap 102, anchoring fabric 116 and/or supporting structure 108. The attachment points may take on any number of suitable forms including, for example, a hook and loop fastener (e.g., Velcro®), a clasp, a button, and/or any other suitable type of fastening mechanisms. For example, the foot plate 114 may include one or more alligator-clip type fastening mechanisms as is described in, for example, FIG. 2H discussed infra. As but another non-limiting example, one or more attachment points on one or more of the adjustable strap 102, anchoring fabric 116 and/or supporting structure 108 may utilize the backside of the rotary tensioning mechanism 104 in combination with a D-ring as illustrated in FIG. 2I. These and other variants would be readily apparent to one of ordinary skill given the contents of the present disclosure.

Figure 2A:
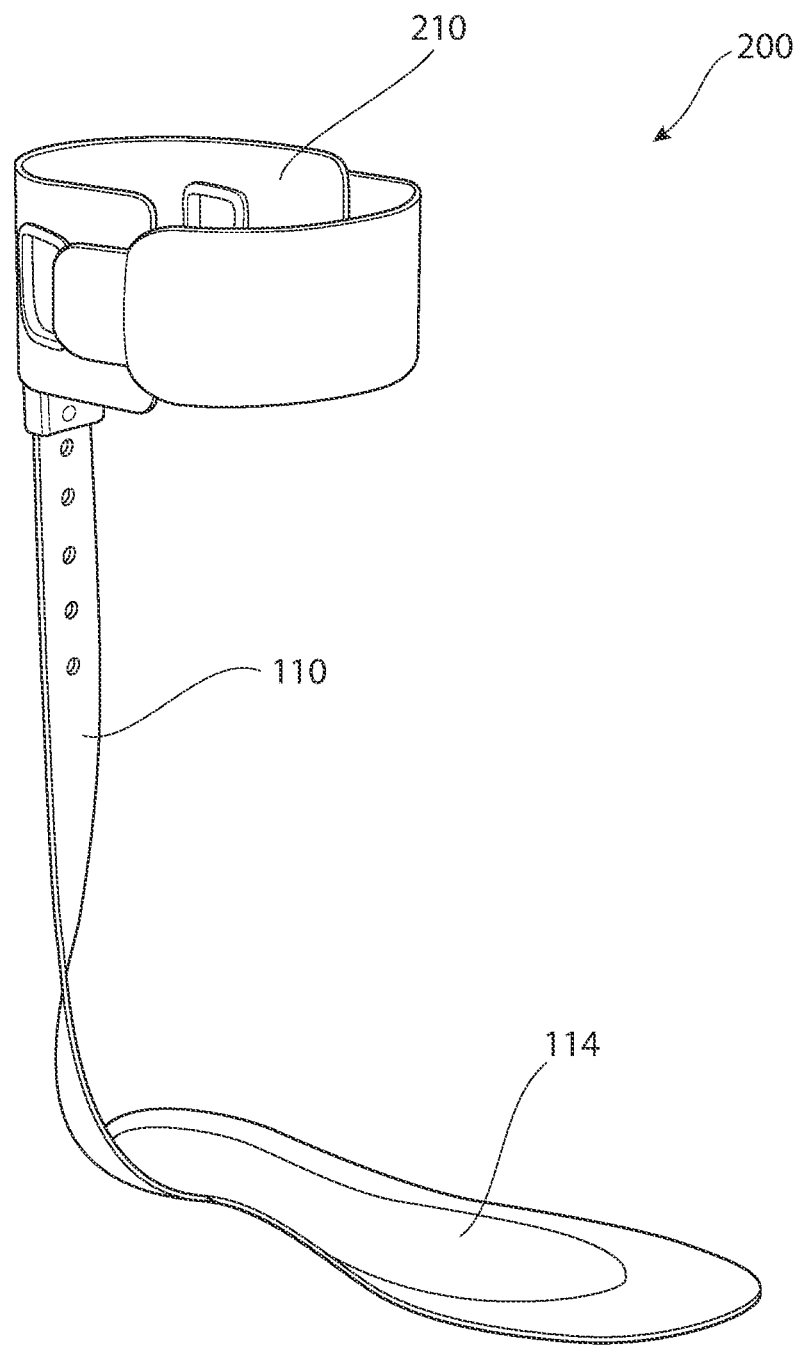
FIG. 2A is a perspective view of yet another exemplary AFO device, in accordance with the principles of the present disclosure.

Referring now to FIGS. 2A-2I, another variant of a rigid or semi-rigid AFO 200 (or portions thereof) are shown and described in detail. Similar to that shown in FIGS. 1A-1C, AFO 200 includes a foot plate 114, a spiral strut 110 that is configured to be disposed around the foot and ankle either laterally (as shown) or medially and run up along a user's calf muscle, and a supporting structure 210. While FIG. 2A illustrates the strut 110 coming up the lateral side of the foot to the posterior side of the wearer's leg, it would be readily apparent to one of ordinary skill that other variants may have different configurations. For example, the strut 110 may come up the lateral side of the foot to the anterior side of the wearer's leg. As but another non-limiting example, the strut 110 may come up the medial side of the foot to the anterior side of the wearer's leg. As but yet another non-limiting example, the strut 110 may come up the medial side of the foot to the posterior side of the wearer's leg in some implementations. As but yet another non-limiting example, the strut 110 may come up straight posteriorly from the footplate such that the strut 110 is positioned behind the wearer's leg.

Figure 2B:
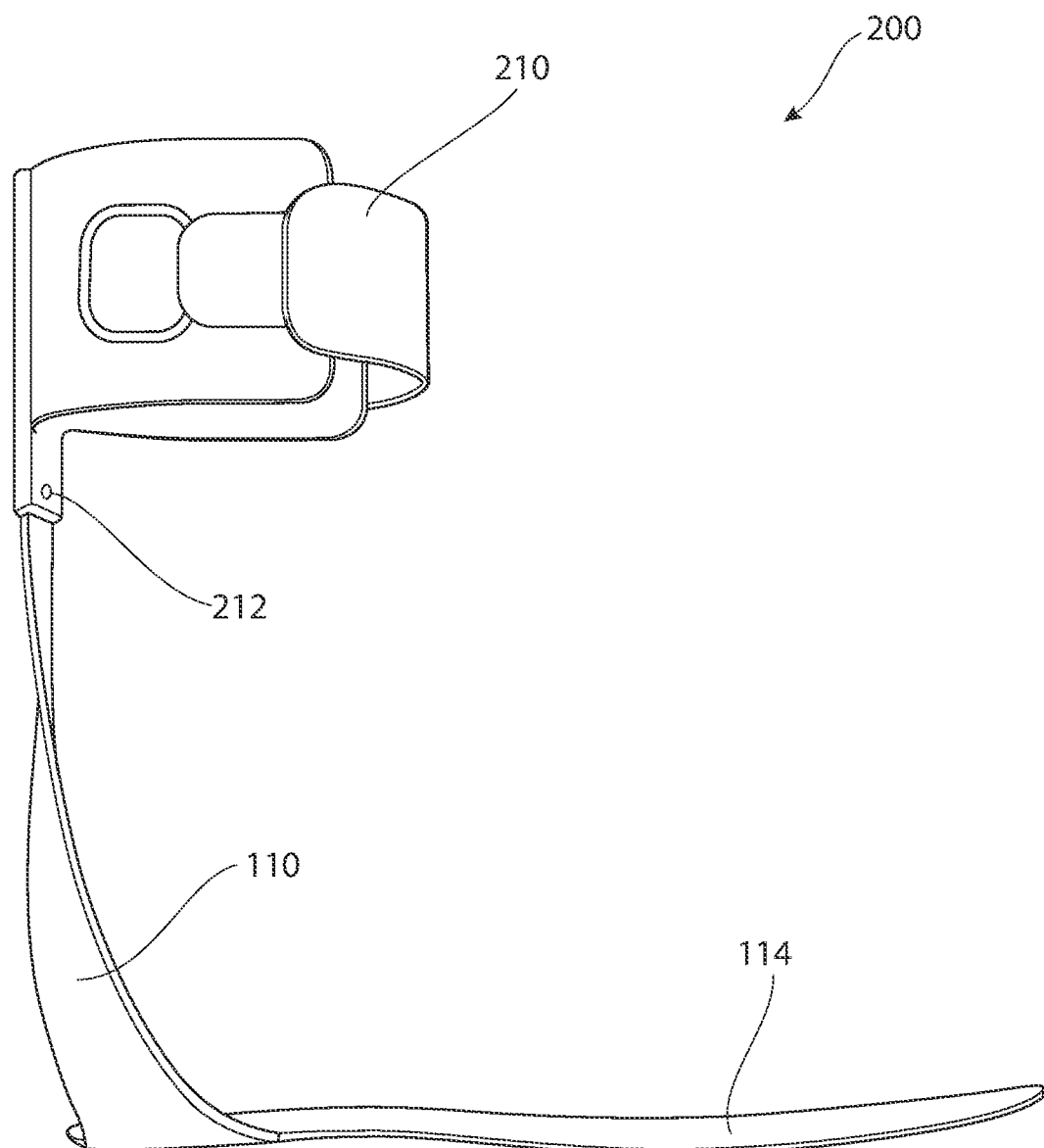
FIG. 2B is a side view of the exemplary AFO device of FIG. 2A, in accordance with the principles of the present disclosure.
Figure 2C:
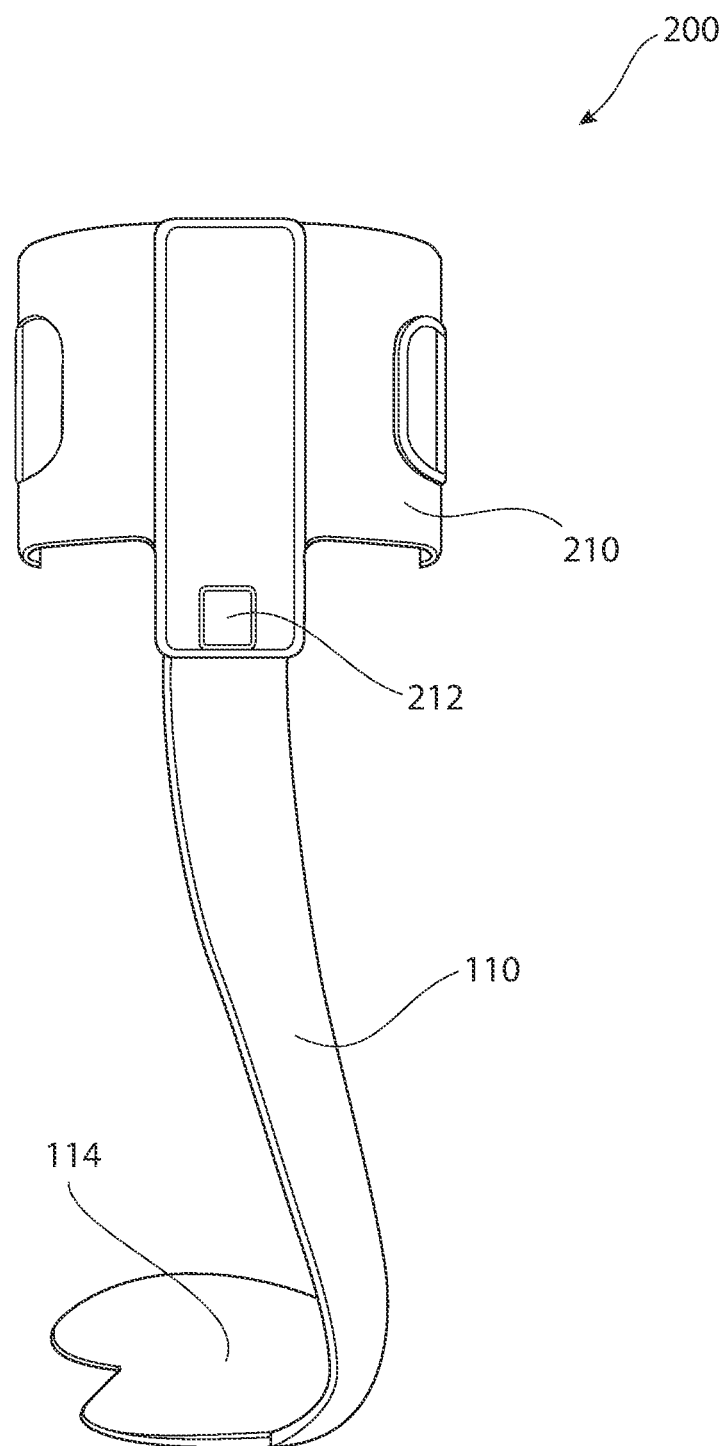
FIG. 2C is a back view of the exemplary AFO device of FIG. 2A, in accordance with the principles of the present disclosure.
Figure 2D:
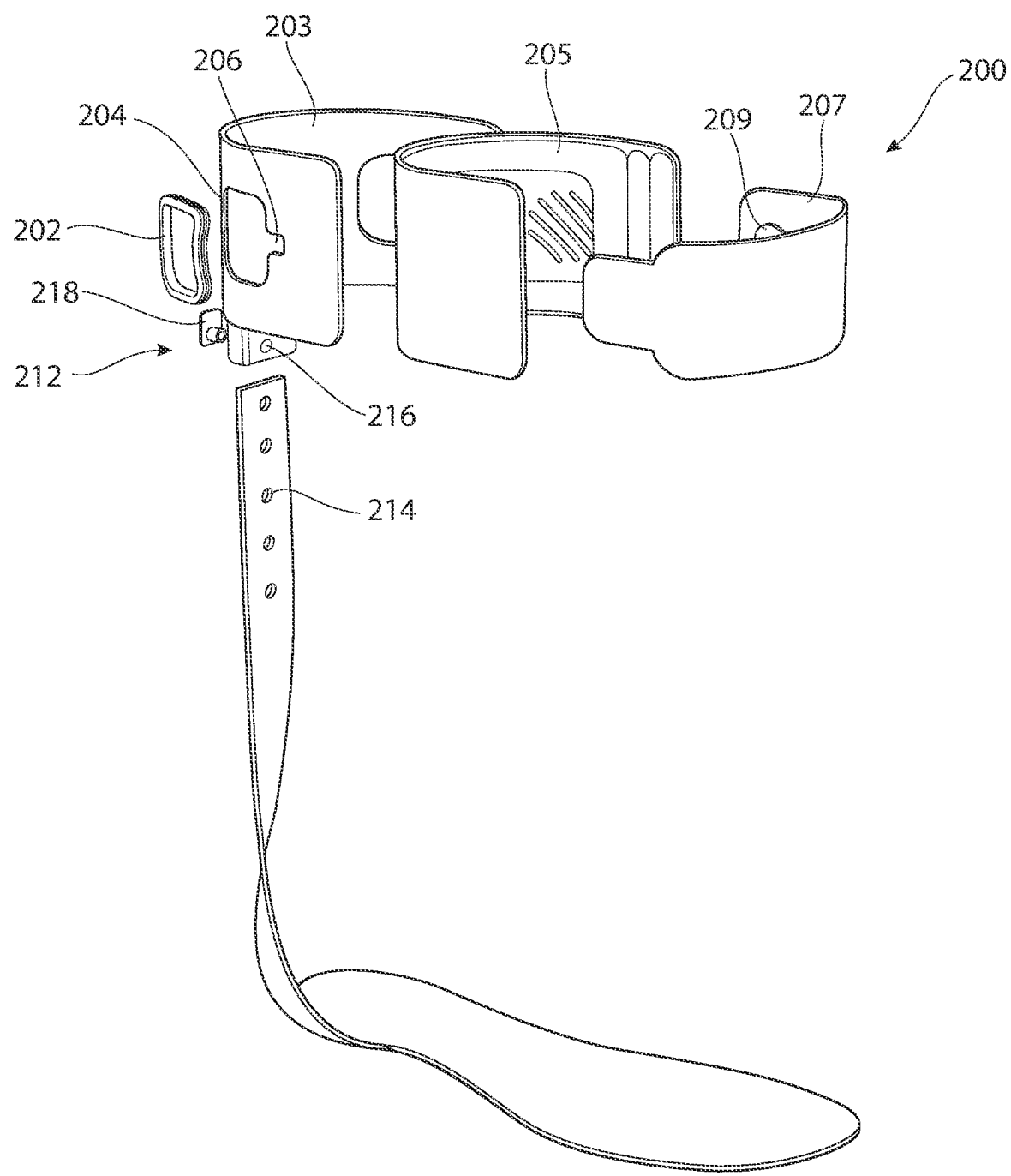
FIG. 2D is an exploded view of the exemplary AFO device of FIG. 2A, in accordance with the principles of the present disclosure.

As shown in, for example, FIGS. 2B and 2C, the AFO 200 includes a height adjustment feature 212. In FIG. 2D, the height adjustment feature 212 is shown in additional detail. Specifically, the strut 110 includes a plurality of apertures (e.g., five (5)), although more or fewer apertures 214 may be readily substituted in alternative variants. The supporting structure 210, and in particular rear cuff 203 also includes one or more apertures 216 along with a T nut and screw mechanism 218 although alternative mechanical locking mechanisms may be readily substituted in alternative variants. Herein lies one salient advantage of the AFO 200 of the present disclosure. Namely, the ability for a retailer to stock a single (or a small number) of AFO devices 200 that may be modified to fit a variety of differently sized wearers as needed. Moreover, while the example illustrated in FIGS. 2B-2D is height adjustable in a discrete number of positions, in alternative implementations, the height adjustability may have infinite adjustability which may be accomplished through, for example, a set screw which utilizes friction in order to position the supporting structure 210 at any number of suitable heights dependent upon the anatomy of the wearer (see also FIG. 8 described infra). In some variants, the top portion of the strut 110 may be trimmable in order to enable the orthosis 200 to accommodate tall individuals (for example, greater than six (6) feet) as well as shorter individuals (for example, less than five (5) feet). In some implementations, the spiral strut ensures a sufficient vertical strut section to allow for increased height adjustability (e.g., to capture patient sizes from an XS to XXXL). The vertical strut starts low on the spiral strut so that the calf piece can slide up and down a sufficient distance to accommodate these variations in a patient's anatomy. In some implementations, the AFO can be scaled down to be incorporated into a pediatric (kids) version to accommodate all sizes in those pediatric categories.

AFO's, such as the AFO 200 illustrated in FIGS. 2A-2I and other AFOs described herein, may be constructed in numerous ways, including as a: posterior spring AFO; posterior frame/posterior lateral strut connection to a footplate; posterior frame/posterior medial strut connection to a footplate; posterior frame/anterior lateral strut connection to a footplate; posterior frame/anterior medial strut connection to a footplate; anterior frame/posterior lateral strut connection to a footplate; anterior frame/posterior medial strut connection to a footplate; anterior frame/anterior lateral strut connection to a footplate; and an anterior frame/anterior medial strut connection to a footplate.

For example, with an AFO design that only supports plantar flexion, a posterior frame with the strut connection on the posterior lateral side for fit provides optimal support in one direction. As but another non-limiting example, when dorsiflexion support is needed an anterior frame with the strut connection on the anterior lateral side so that the brace carries more support in the forward flexion may be utilized.

For a one size fits all drop foot AFO the same structure may be optimal for a universal fit. Having a posterior frame, the strut connection may be more posterior so that the strut does not have to travel as far around the leg as if it were placed anteriorly. For a one size fits all drop foot AFO that provides dorsiflexion support an anterior frame for a one size fits all having the strut on the lateral side and more anterior makes the strut have to travel less distance around the leg compared to having the strut connection more posterior.

As depicted, the rear cuff 203 (or front cuff 207 in some implementations) also includes two cut-outs 204 that are disposed on alternative sides of the rear cuff 203, although more or less cut-outs 204 may be implemented in some implementations. Each of these cut-outs 204 includes a keyed feature 206 which is configured to receive a corresponding button 209 located on the front cuff 207. These buttons 209 are configured to be received within the cut-outs 204 and pulled forward so that they hook into respective keyed features 206. A snap ring 202 is inserted into one (or both) of the cut-outs 204 and prevents the button(s) from unintentionally being released from the rear cuff 203. For example, the use of the snap ring 202 prevents movement of a button 209 located within the keyed feature 206. A padded cuff 205 may also be inserted between the rear cuff 203 and the front cuff 207 in order to assist in comfort for the wearer of the AFO 200. While a specific implementation has been contemplated, it would be readily appreciated that alternative attachment structures such as D-rings, hook and loop fasteners, rotary tensioning mechanisms and other types of mechanical attachment mechanisms may be readily substituted in some implementations.

In some implementations, the rear cuff 203 (and/or front cuff 207) may be trimmable. For example, trim lines may be included on the rear cuff 203 and/or the front cuff 207 which enables, for example, a clinician to cut and shape the supporting structure 210 in order to properly fit with a given user's anatomy. The portion of the rear cuff 203 and/or the front cuff 207 that receives the strut 110 may itself be trimmable to enable further customization for a given user. For example, a clinician may be able to cut the length of this tunnel via provided lines with a pair of scissors, or in other implementations, may simply snap off the unneeded length.

Figure 2E:
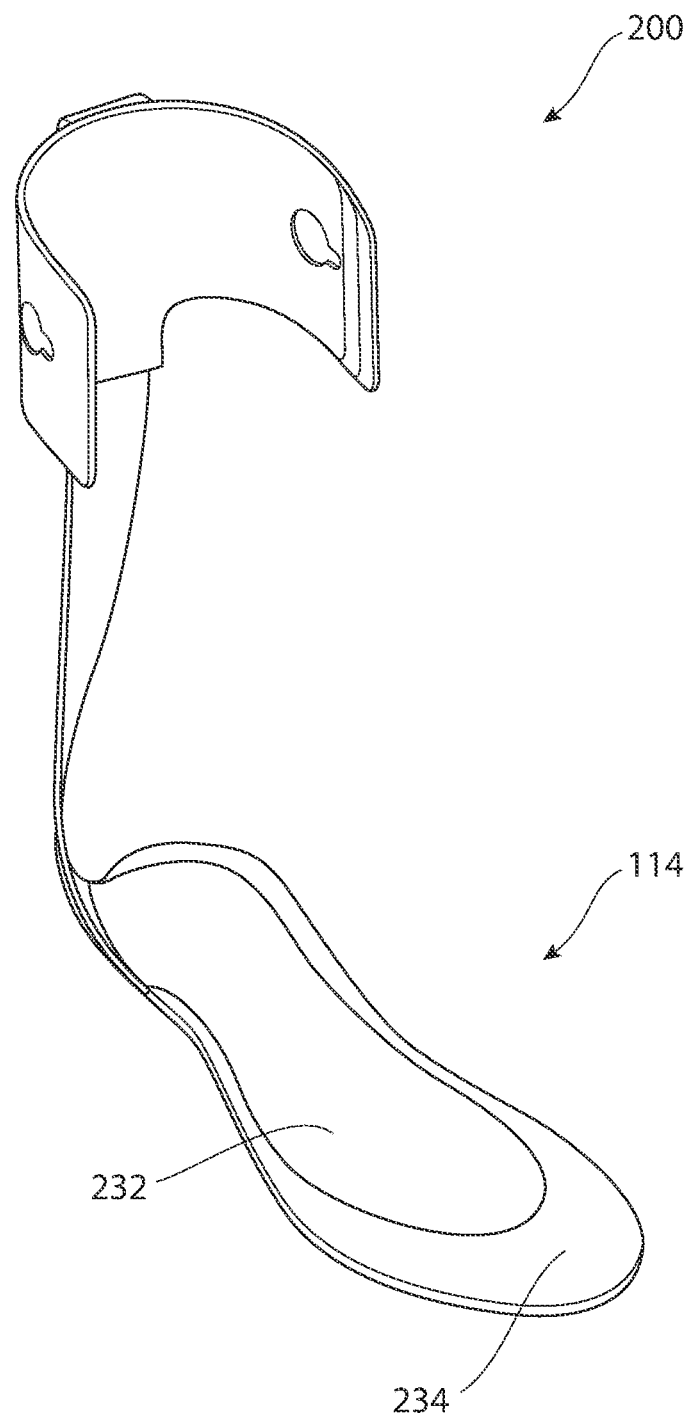
FIG. 2E is a front perspective view of the exemplary AFO device of FIG. 2A, illustrating a trimmable foot plate, in accordance with the principles of the present disclosure.
Figure 2F:
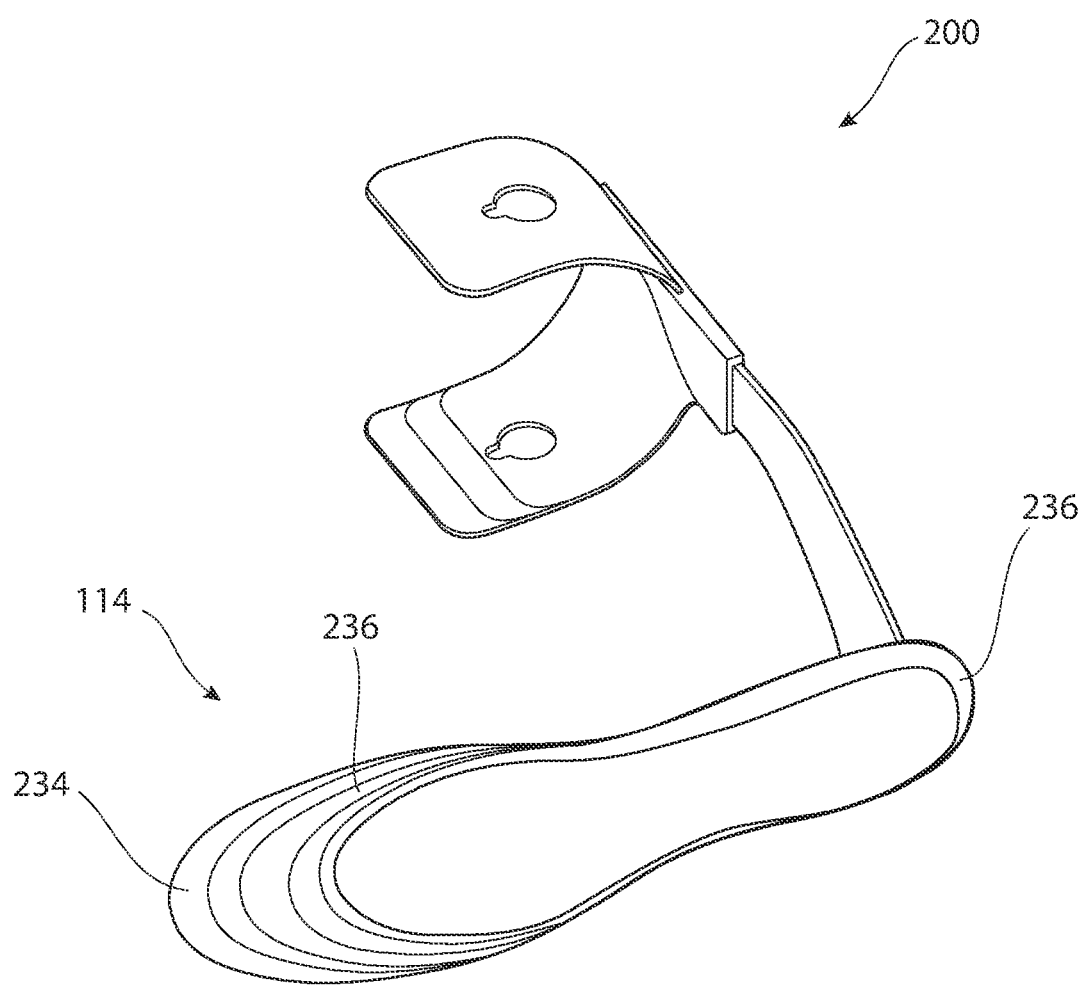
FIG. 2F is a bottom perspective view of the exemplary AFO device of FIG. 2A illustrating the trimmable foot plate, in accordance with the principles of the present disclosure.

Embodiments of the foot plate 114 are described with reference to FIGS. 2E and 2F. The foot plate 114 illustrated in FIGS. 2E and 2F may be trimmable in some implementations. For example, as shown in FIG. 2E, the AFO 200 may be sized from an extra small 232 to an extra-large 234. Portion 232 may be made from, for example, carbon fiber or other rigid materials. In some implementations, portion 232 may take the form of a spring-like material (e.g., aluminum or other suitable spring-like material) that has been overmolded with, for example, a soft rubber. Such a configuration may enable the foot plate 114 to be readily modified and molded to a given wearer's foot. Carbon and glass materials may form the front (disposed towards the metatarsals of a wearer) and rear-most (disposed towards the heel of a wearer) portions of portion 232 that are joined together using, for example, a spring like-material. For example, the spring-like material may have a thickness of approximately 1 mm and a width of approximately 25 mm. The extra-large portion 234 is intended to be trimmable so as to accommodate, for example, a size extra small foot to a size extra-large foot. The extra-large portion 234 may be made from a glass fiber material with resin, a plastic or rubber-like material, and/or a polyester fabric with resin, or any other suitable materials that are trimmable and provide the required support. These and other variations will be described herein with respect to the foot plate 114 described infra.

Trim lines 236 may be located on the top and/or bottom of the foot plate 114. These trim lines 236 may be resident around the external periphery (front, sides and rear) of the foot plate 114. Accordingly, a wearer may simply determine the periphery that fits his or her feet and trim the extra-large portion 234 accordingly in order to properly size the AFO 200. Herein lies another salient advantage of the AFO 200 of the present disclosure. Namely, the ability for a retailer to stock a single (or a small number) of AFO devices 200 that may be sized to a variety of differently sized wearers as needed. For example, a retailer may only need to stock one AFO intended for the right leg of its wearer and one AFO intended for the left leg of its wearer. In some implementations, the spring-like material may be able to conform to the shape of the wearer's foot enabling further adjustment for a variety of anatomical shapes/sizes. In order to capture the footplate shape of every user size XS to XXXL and in other cases pediatric and children's versions the entire periphery of the footplate may be trimmed, excluding the area where the spiral strut connects to the footplate. In some implementations, dependent on shoe shape and the size of the foot, the clinician may not have to trim the entire periphery of the footplate excluding where the strut connects to the footplate. In a majority of instances, at least the majority of the footplate must be trimmed to accommodate shoe sizes from size 6 to size 12 in adults.

Figure 2G:
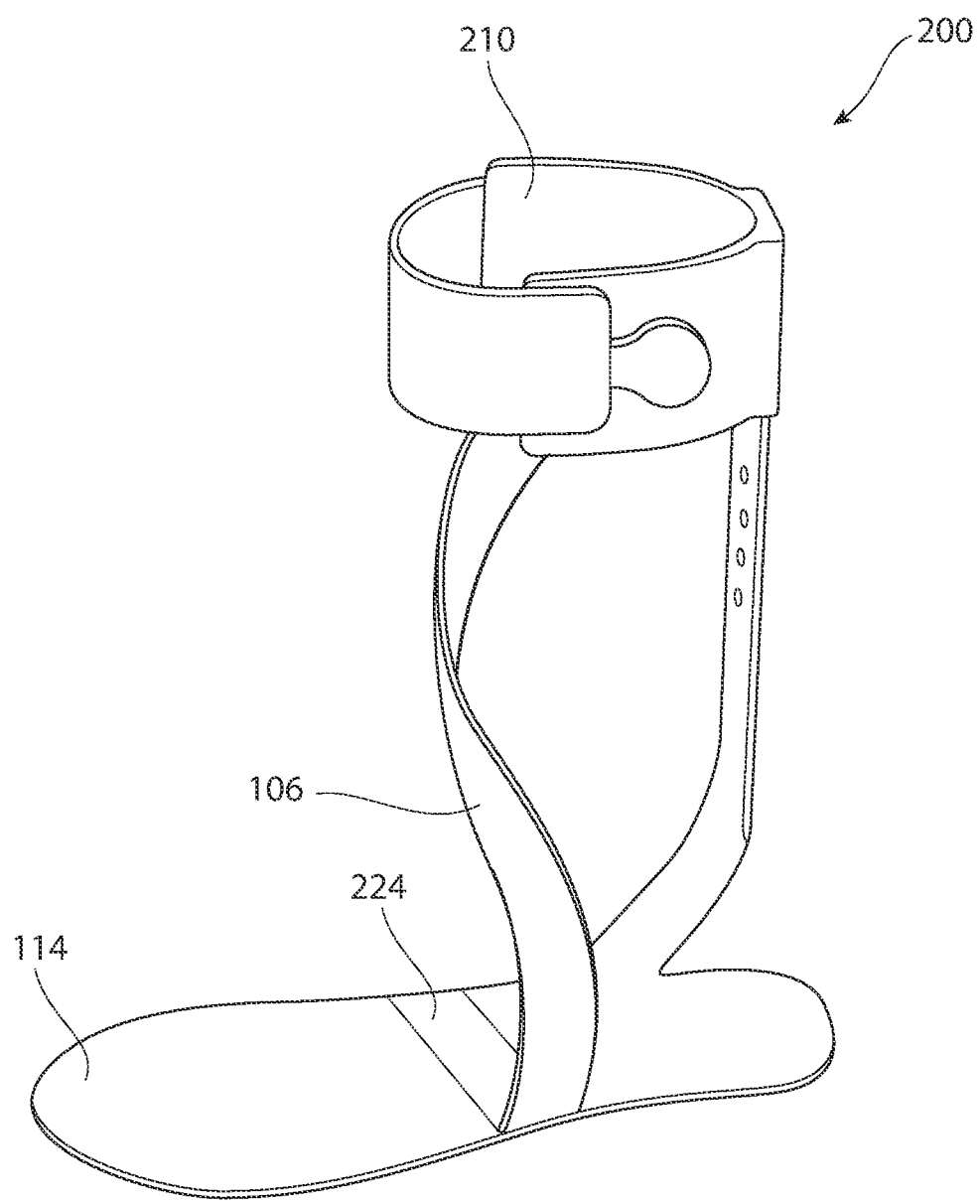
FIG. 2G is a front perspective view of the exemplary AFO device of FIG. 2A that incorporates a support strap, in accordance with the principles of the present disclosure.

FIG. 2G illustrates a support strap 106 that may be utilized in combination with the AFO 200. As shown, the support strap 106 includes a bottom portion 224 that is positioned on the top of the foot plate 114 so that it wraps around the medial side of the foot, wraps around the lower leg of the wearer and attaches to the support structure 210 on the lateral side of the calf. Such a configuration as illustrated provides support during plantar flexion as well as controls varus deformities. In some implementations, the support strap 106 may also come up medially at the foot, spiral up the lower leg of the wearer and be attached to the support structure 210 on the medial side of the calf. Such a configuration as illustrated provides support during plantar flexion as well as controls valgus deformities. The support strap 106 may also wrap around the lateral side of the foot, wrap around the lower leg of the wearer and attach to the support structure 210 either medially or laterally (or even in the forward or rear portion of the support structure 210). For example, the positioning of the support strap 106 may be configured to accommodate varus or valgus medical conditions within the wearer of the AFO 200. The lifting capabilities of such a support strap 106 is described in additional detail herein with respect to FIGS. 5A and 5B discussed infra. These and other variants would be readily apparent to one of ordinary skill given the contents of the present disclosure.

Figure 2H:
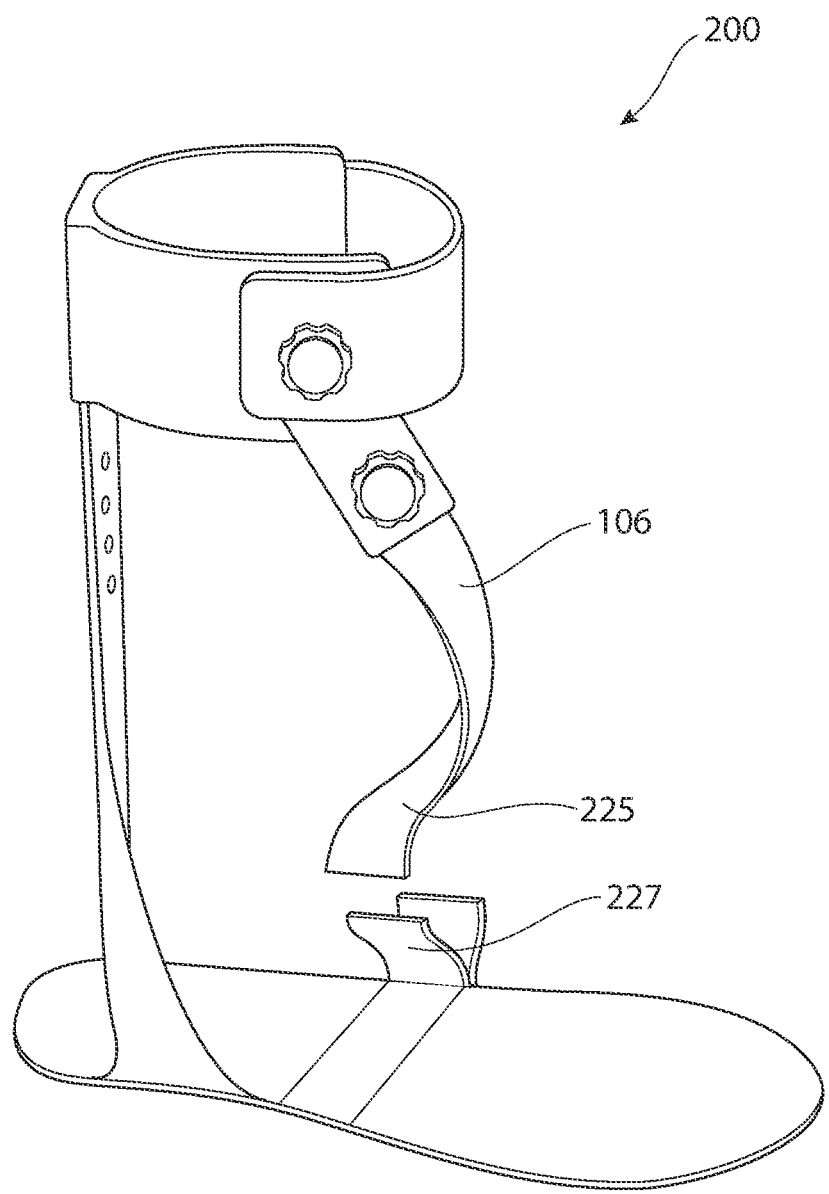
FIG. 2H is a side view of another exemplary AFO device with a bottom attachment feature for the support strap, in accordance with the principles of the present disclosure.
Figure 21:
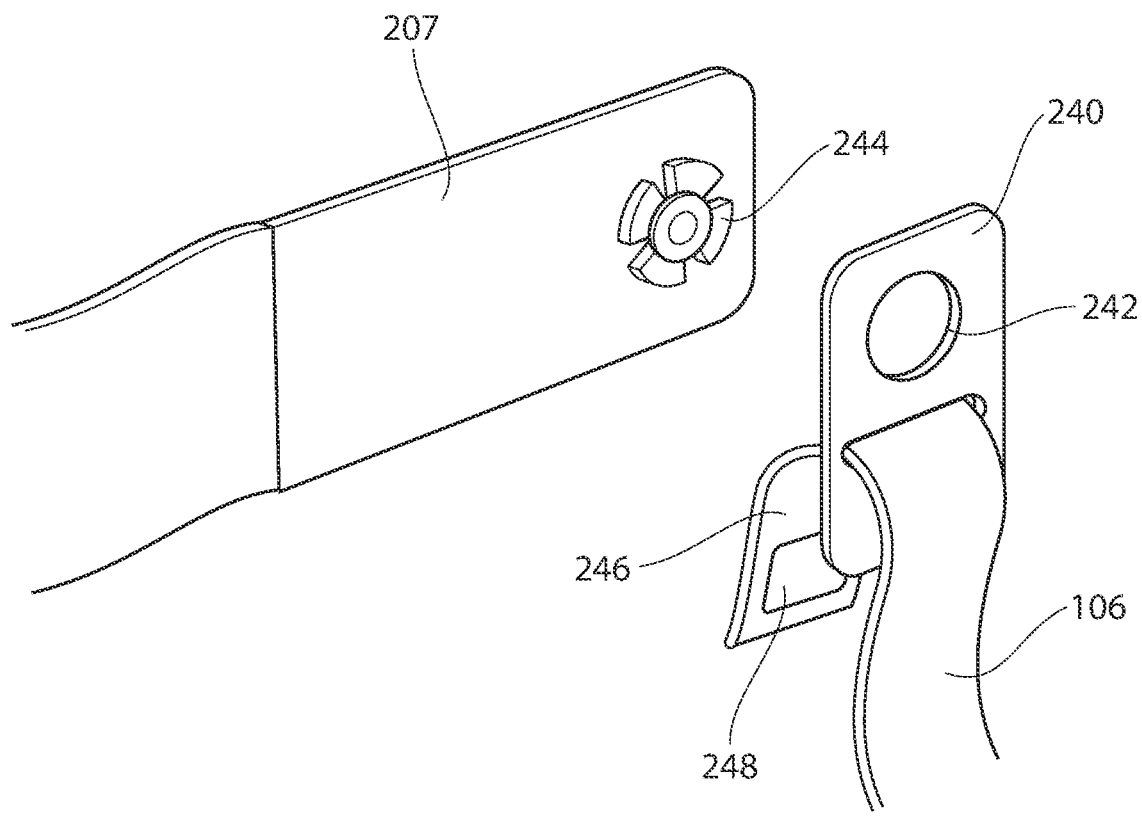

A rotary tensioning mechanism may be incorporated with the AFO 200 in some implementations and may operate in accordance with, for example, the embodiments discussed elsewhere herein. FIG. 2H illustrates an implementation which utilizes, for example, an alligator-clip type portion 227 that clips onto the bottom portion 225 of the support strap 106. In some variants, the alligator-clip type portion 227 may be obviated in favor of a hook and loop fastener (e.g., Velcro) that may be secured to the foot plate 114 using, for example, glue, rivets, etc. In such an implementation, the support strap 106 may secure to the hook and loop fastener by having a corresponding hook and loop fastener on the bottom portion 225 of the support strap 106. Other attachment means may be readily substituted including rivets or other types of mechanical attachments. The support strap 106 may be inelastic, may be fully elastic, or may have partial elasticity by having, for example, elastic materials sewn within the support strap 106. Referring now to FIG. 2I, a backside view of the rotary tensioning mechanism and its attachment to the front cuff 207 is shown and described in detail. The backside 244 of the rotary tensioning mechanism includes features which enables it to be coupled to a D-ring 240. In particular, aperture 242 is configured to receive the backside 244 of the rotary tensioning mechanism. The D-ring 240 is also configured to receive the support strap 106 in the illustrated variant. One end 246 of the support strap 106 may include a fastening mechanism 248 such as, for example, a hook and loop fastener, a clasp, a button, or any other suitable type of fastening mechanism which allows for the support strap 106 to be tightened to an appropriate amount of tension dependent upon the condition of the wearer.

Referring now to FIGS. 3A-3E, yet another exemplary AFO 300 is shown and described in detail, also known as an anterior AFO 300. Specifically, in this illustrated embodiment, the strut 110 is shown as coming up the lateral side of the foot plate 114 to the anterior portion of the wearer's leg. Both the strut 110 as well as portions of the foot plate 114 may be manufactured from carbon fiber. For example, in some implementations, carbon fiber strands present within the strut 110 may also be present within portions of the foot plate 114. In some implementations, the foot plate 114 may also be trimmable as described elsewhere herein. The strut 110, also known as a spiral strut, transitions from the lateral side of the foot to the anterior portion of the wearer's leg quickly which enables height adjustability for a variety of different user anatomies. For example, in some implementations, the transition portion (330, FIG. 3E) of the strut 110 may be coupled with the foot plate 114 and spiral by approximately 90° (i.e., a range between 80° and 100°) to an adjustable portion (332, FIG. 3E) of the strut 110 within less than approximately 160 mm (6.3 inches) of the bottom of the foot plate 114. In some implementations, the height between the bottom of the foot plate 114 and the adjustable portion (332, FIG. 3E) is greater than approximately 100 mm (4 inches). The transition portion (330, FIG. 3E) of the strut 110 is more aggressive than prior AFO designs yet provides numerous additional benefits over prior spiral strut AFO designs including providing an increased amount of strut 110 that can flex under loading thereby increasing the durability of the AFO 300.

The relatively compact dimension of the transition portion (330, FIG. 3E) of the strut 110, especially when the strut 110 is manufactured from carbon fiber, has been historically challenging as it has been difficult to lay up the carbon fibers without causing wrinkles in the laminate portion of the carbon fiber structure. Traditionally, prior art AFOs have been manufactured using a positive mold taken from the patient's anatomy. Plastic or carbon fiber is then laid up around the positive mold and a combination of heat and vacuum is applied to the underlying plastic or carbon fiber using an autoclave. However, after extensive experimentation, the assignee of the present application has produced an AFO strut 110 with a transition portion (330, FIG. 3E) that is less than approximately 160 mm (6.3 inches) in height from the bottom of the foot plate 114, through use of a compression molding technique. The compression molding technique involves acquiring a pre-impregnated carbon fiber sheet as well as a pre-impregnated glass fiber sheet. The carbon fiber sheet and the glass fiber sheet are trimmed to the desired size and layered inside a multi-piece mold made of a rigid material (e.g., steel and similar materials utilized in molding processes), dependent upon the underlying structural requirements of the finished AFO. In some implementations, the carbon fiber sheet (and optionally the glass fiber sheet) include so-called long carbon fiber sheets such that individual ones of the carbon fibers (and in some instances, glass fibers) are placed in the mold such that unitary ones of the fibers are present in both, for example, the strut 110 as well as the foot plate 114. For example, a single fiber carbon strand may start from inside the strut 110 in the adjustable portion (332, FIGS. 3E, 3I), transition into the transition portion (330, FIGS. 3E, 3I) of the strut 110, and run from the transition portion (330, FIGS. 3E, 3I) of the strut 110 into the foot plate 114 in accordance with the various geometries discussed elsewhere herein. The multi-piece mold is then closed and compressed under pressure and heat in order to activate the resin system(s) present within the pre-impregnated sheets of material. Once the resin system has hardened, the AFO 300, 350 is then removed from the mold. In some implementations, the AFO 300, 350 undergoes post-processing to clean up the edges from the molding process. Such compression molding techniques enable complex geometries to be formed that are highly repeatable and consistent in dimension.

In some implementations, the adjustable portion (332, FIG. 3E) of the strut 110 may consist of a straight (flat) vertical section of carbon fiber that enables a wide range of adjustability in height for the front cuff 302. For example, in some implementations, the adjustable/straight portion (332, FIG. 3E) of the strut 110 may be approximately 160 mm (6.3 inches) in length, thereby enabling the AFO 300 to accommodate users having a height ranging from approximately 1.5 m (4 foot, 10 inches) to 2.0 m (6 foot, 7 inches), dependent upon variations in tibial length for individual ones of these users, within a single AFO device 300. Accordingly, in some implementations, the overall height of the strut 110 may be approximately 320 mm (12.6 inches) and is achievable due to the placement of the strut 110 with respect to the foot plate 114, although it would be appreciated that overall height of the strut 110 may be suitably lengthened or shortened to accommodate larger individuals (e.g., over 2.0 m (6 foot, 7 inches) in height) and smaller individuals (e.g., less than 1.5 m (4 foot, 10 inches) in height). In some implementations, the thickness of the strut 110 may be relatively uniform in thickness due to the aforementioned compression molding process.

The front cuff 302 may also include a height adjustment mechanism 304, such as those described elsewhere herein. For example, the height adjustment mechanism 304 may enable discrete height adjustment for the AFO 300 (e.g., every 15 mm (0.6 inches)) or may enable infinite height adjustment, over the length (or vast majority of the length) of the adjustable portion of the strut 110, through use of a set screw, etc. as described elsewhere herein. In some implementations, the front cuff 302 may include a single adjustment point 304 which enables an increased amount of adjustability over the adjustable portion (332, FIG. 3E) of the strut 110 as compared with a comparable AFO with multiple adjustment points. For example, and referring specifically to FIG. 3A, if the AFO 300 included a second adjustment mechanism (similar to adjustment mechanism 304) at the top of the front cuff 302, the maximum height adjustability for the AFO 300 would be less when using a comparable strut 110, as compared with the embodiment illustrated in FIG. 3A. In other words, because the theoretical height adjustment mechanism would be present at the top of the front cuff 302 (as opposed to the approximate center as illustrated in FIG. 3A), the front cuff 302 would not be able to take advantage of the full range of motion enabled by the adjustable portion (332, FIG. 3E) of the strut 110.

In some implementations, the overall height of the AFO 300 depicted in FIGS. 3A-3E may range from between 360 mm (14.25 inches) to 432 mm (17 inches), or may range from between 375 mm (14.75 inches) to 413 mm (16.25 inches). Although specific dimensions have been provided herein, it would be appreciated by one of ordinary skill given the contents of the present disclosure that these specific dimensions may be varied dependent upon the specifics of the AFO design. Rather, it is a primary goal of embodiments of the present disclosure for the AFO 300 to incorporate a spiral strut 110 design that allows for a wide range of height adjustability, due to the strut's 110 positioning with respect to the foot plate, that can accommodate patient sizes from XS to XXXL. Moreover, it would be appreciated the specific dimensions described herein have been primarily discussed in the context of adult human beings, and that similar variability to accommodate various sizes are also possible with other populations of individuals such as, for example, children (pediatrics) or other populations of individuals which have a range other than the aforementioned 1.5 m (4 foot, 10 inches) to 2.0 m (6 foot, 7 inches).

The front cuff 302 may be elongated as compared with the rear cuff 308 to provide additional surface area that is in contact with the wearer, making the AFO 300 more comfortable to wear. Both the front cuff 302 as well as the rear cuff 308 may include a padded liner on its interior, thereby further facilitating comfort and support for the wearer. Padded inserts may be inserted into, for example, the front cuff 302 to accommodate different anatomies of the wearer. Cut-outs 312 along with apertures 306 located on the front cuff 302 may assist with breathability for the AFO 300 and comfort for the wearer. The rear cuff 308 may attach to the front cuff 302 using cutouts 312, using the mechanism described with reference to, for example, FIG. 2D described herein. A rotary tensioning mechanism 104 may be utilized to tighten (or loosen) the combination of the front cuff 302 and the rear cuff 308 around the wearer's calf thereby facilitating easy donning and doffing. The rotary tensioning mechanism 104 (or separate rotary tensioning mechanism 104) may also be utilized in combination with a support strap to support various varus and/or valgus deformities present with the wearer as described elsewhere herein.

Figure 3A:
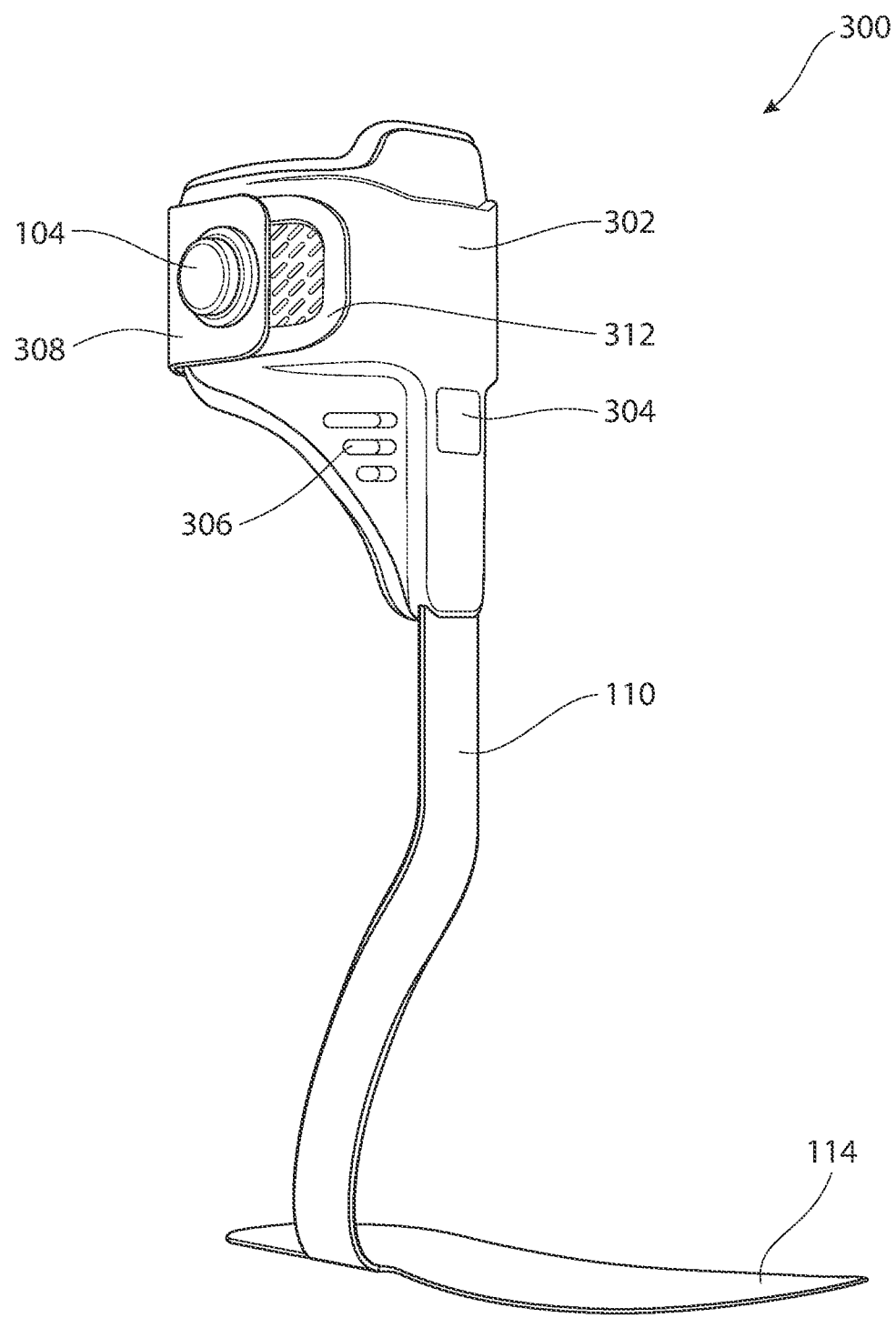
FIGS. 3A-3E are various views of an exemplary anterior AFO device, in accordance with the principles of the present disclosure.
Figure 3B:
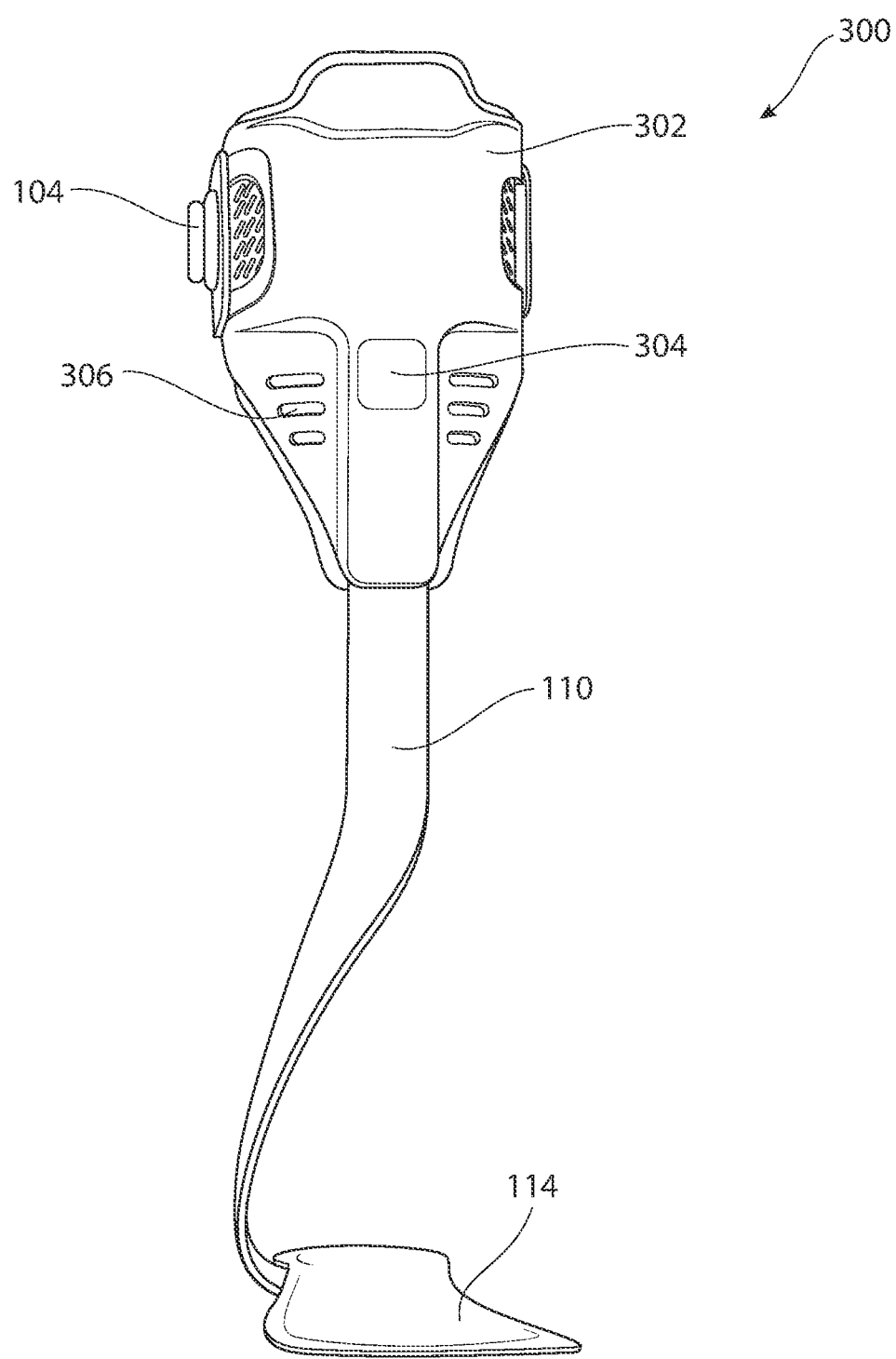
Figure 3C:
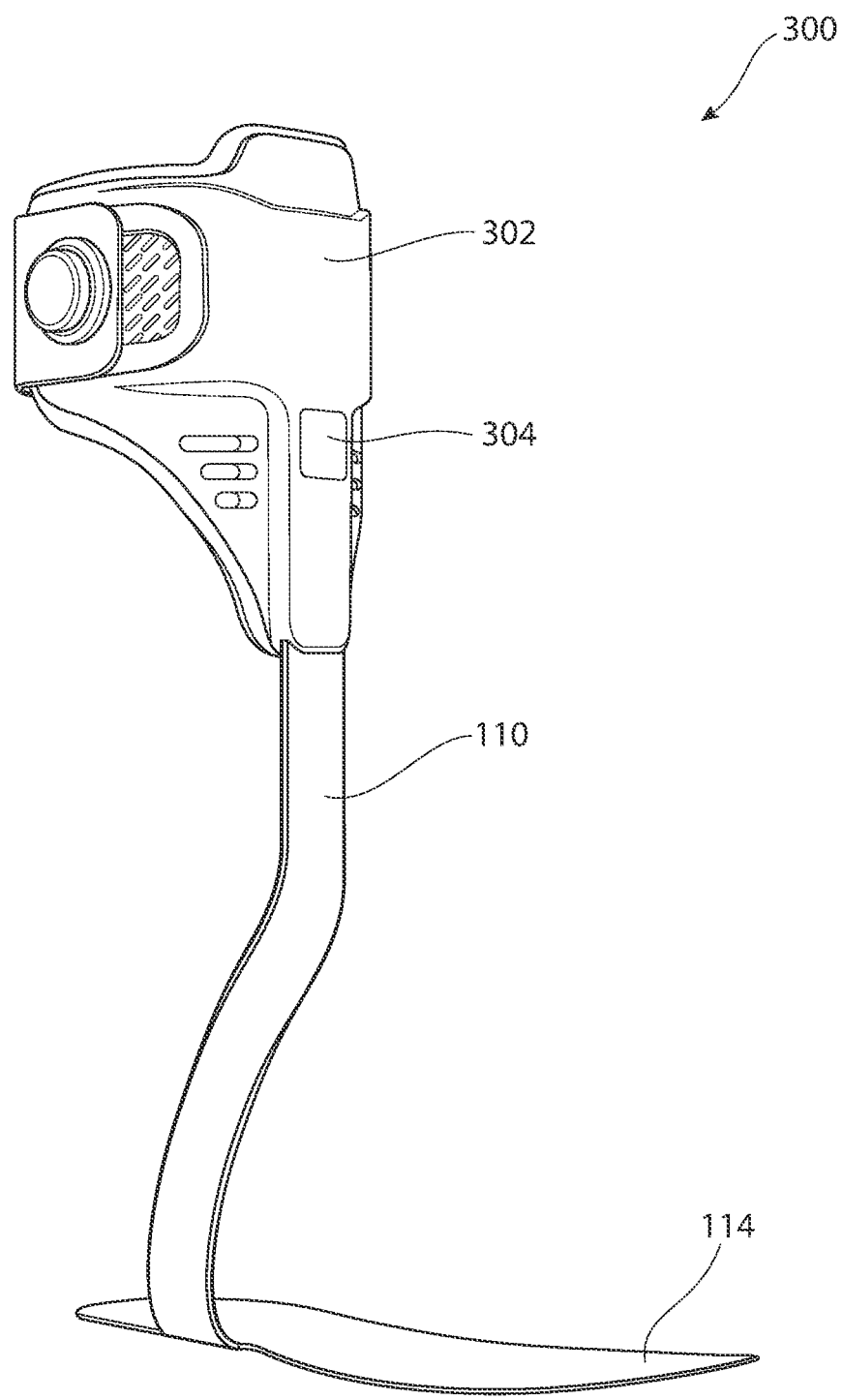
Figure 3D:
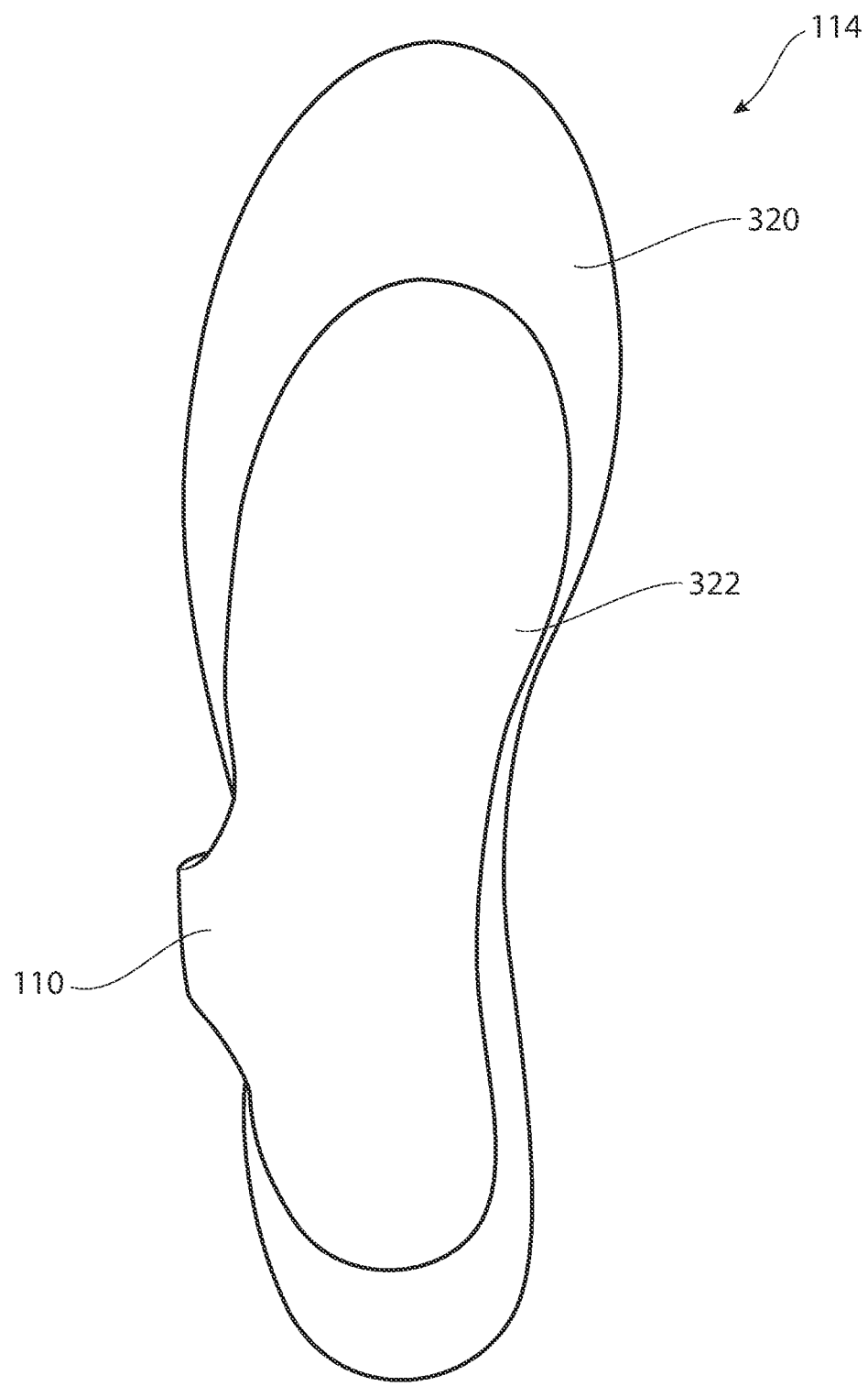
Figure 3E:
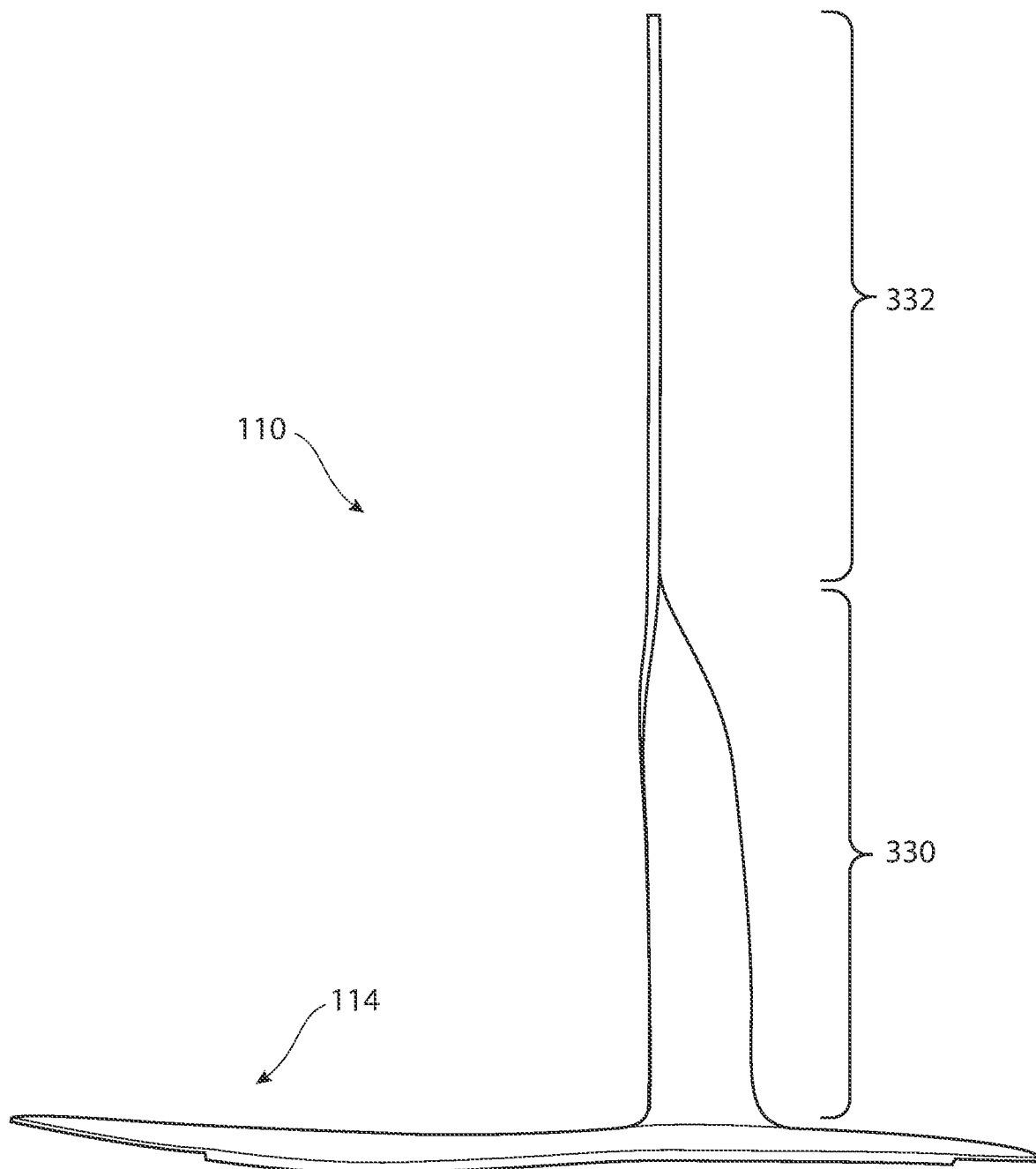
Figure 3F:
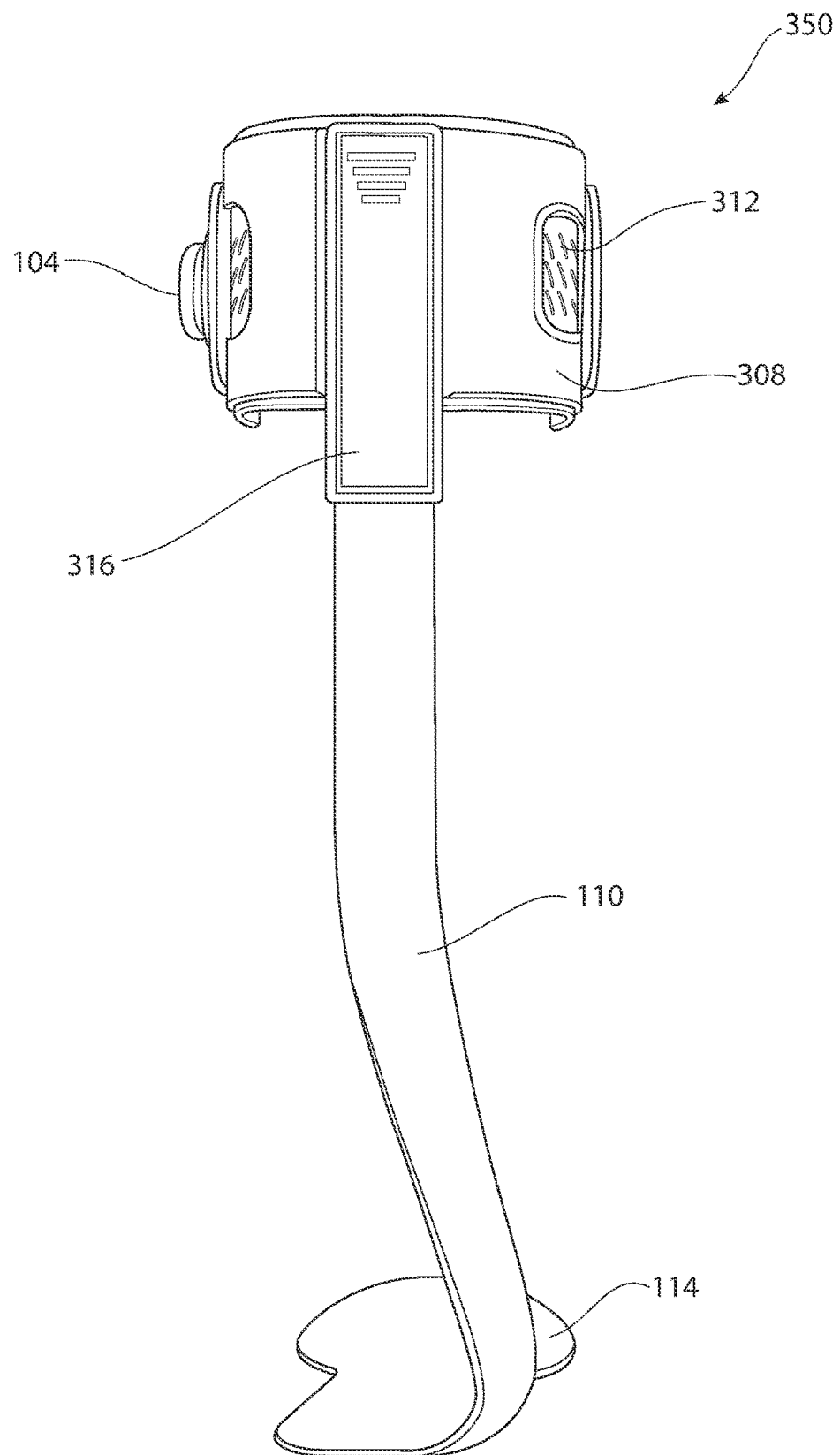

Referring now to FIG. 3D, an exemplary foot plate 114 is shown for use with, for example, the AFO 300 shown in FIGS. 3A-3C. The foot plate 114 may include a non-trimmable portion 322 that is coupled with the strut 110 as well as a trimmable portion 320 which surrounds much of the periphery of the non-trimmable portion 322. In some implementations, the non-trimmable portion 322 is manufactured from carbon fiber, while the trimmable portion 320 is manufactured from glass fiber. The trimmable portion 320 may share a common layer of material with the non-trimmable portion 322 and may be thinner in thickness than the non-trimmable portion 322 to provide, inter alia, a visual queue for the trimmable area 320 (i.e., a visual indication as to which areas may be trimmed). The transition area between the thinner trimmable portion 320 and the thicker non-trimmable portion 322 may include a fillet (or concaved junction), which strengthens the overall foot plate 114 design by minimizing areas of weakness. In other words, by including the fillet the trimmable portion 320 is less susceptible to unintentional fracture (and breaking off) from the non-trimmable portion 322 of the foot plate 114. In some implementations, the foot plate 114 may be constructed in accordance with the embodiment described with reference to FIGS. 6A and 6B described infra.

In some implementations, the overall length of the foot plate 114 may be approximately 305 mm (12 inches), while the non-trimmable portion 322 may have an overall length of approximately 214 mm (8.4 inches). In the area towards the wearer's toes, the trimmable portion 320 may have a maximum length of up to about 50 mm (2 inches), while the area near the heel of the wearer, the trimmable portion 320 may have a maximum length greater than 15 mm (0.6 inches) and up to about 25 mm (1 inch) or more. The foot plate 114 may be broken down into a hindfoot section, a midfoot section, and a forefoot section, which generally corresponds to the anatomy of its wearer. However, due to the wide variety of anatomical sizes of feet that the foot plate 114 is intended to accommodate, there may be instances where, for example, a wearer of the foot plate 114 may have their anatomical forefoot positioned in the midfoot section of the foot plate 114. The foot plate 114 profile, as seen in FIG. 3D, widens from the front portion of the foot plate 114 where it reaches a first maximum width. From this first maximum width, the foot plate begins to decrease in width until it reaches a first minimum width in the middle section of the foot plate 114. As you continue to proceed towards the back of the foot plate 114 from the first minimum width, the width of the foot plate 114 again widens (excluding the area of the strut 110) until it reaches its second maximum width. Proceeding towards the back portion of the foot plate 114 from the second maximum width, the foot plate 114 again starts to narrow in width. For purposes of clarity, the hind foot region of the foot plate 114 includes the portion of the foot plate 114 from the second maximum width to the back of the foot plate 114. The fore foot region of the foot plate 114 includes the portion of the foot plate 114 from the first maximum width to the front of the foot plate 114. The mid foot region of the foot plate 114 includes the region between the first maximum width and the second maximum width. In some implementations, the overall periphery of the non-trimmable portion 322 may mimic an extra-small foot, while the overall periphery of the trimmable portion 320 may mimic an extra-large foot. In some implementations, the non-trimmable portion 322 may provide support to the metatarsal region of the wearer, even when the wearer has an extra-large foot size. Moreover, it would be appreciated the specific dimensions described herein have been primarily discussed in the context of adult human beings, and that similar variability to accommodate various sizes are also possible with other populations of individuals such as, for example, children (pediatrics) or other populations of individuals which have a range other than the aforementioned typical adult sizes described herein.

Referring now to FIGS. 3F-3J, yet another AFO 350 (or portions thereof) is shown and described in detail. Specifically, in this illustrated embodiment, the strut 110 is shown as coming up the lateral side of the foot plate 114 to the posterior portion of the wearer's leg. Both the strut 110 as well as portions of the foot plate 114 may be manufactured from carbon fiber or a rigid material. In some implementations, the foot plate 114 may also be trimmable as described elsewhere herein. Similar to the embodiment described supra with reference to FIGS. 3A-3E, the strut 110, also known as a spiral strut, transitions from the lateral side of the hindfoot region of the foot plate 114 to the posterior portion of the wearer's leg quickly which enables height adjustability for a variety of different user anatomies. For example, in some implementations, the transition portion (330, FIG. 3I) of the strut 110 may be coupled with the foot plate 114 and spiral by approximately 65° (i.e., between 55° and 75°) to an adjustable portion (332, FIG. 3I) of the strut 110 within less than approximately 160 mm (6.3 inches) of the bottom of the foot plate 114. In some implementations, the height between the bottom of the foot plate 114 and the adjustable portion (332, FIG. 3I) is greater than approximately 100 mm (4 inches). Again, this transition portion (330, FIG. 3I) is more aggressive than prior AFO designs yet provides numerous additional benefits over prior spiral strut AFO designs including providing an increased amount of strut 110 that can flex under loading thereby increasing the durability of the AFO 350. In some implementations, the transition portion (330, FIG. 3I) includes a curved surface, while the adjustable portion (332, FIG. 3I) includes a flat surface. As described elsewhere herein, the relatively compact dimension of the transition portion (330, FIG. 3I) of the strut 110, especially when the strut 110 is manufactured from carbon fiber, has been historically challenging as it has been difficult to lay up the carbon fibers without causing wrinkles in the laminate portion of the carbon fiber structure. However, after extensive experimentation, the assignee of the present application has produced an AFO strut 110 with a transition portion (330, FIG. 3I) that is less than approximately 160 mm (6.3 inches) in height from the bottom of the foot plate 114, through use of the aforementioned compression molding technique.

As a brief aside, current carbon fiber AFO devices on the market today are made with an autoclave process. This process involves a positive rigid tool in the shape of a foot with the fibers laid onto the mold with vacuum pressure then applied with a soft bladder to the outside of the AFO. The challenges with this process are the dimensional inconsistencies especially given the outer mold which is flexible. In other words, having a flexible outer mold inherently makes a curved shape and it also provides less of a controlled area to hold the fibers in place during the curing process. Accordingly, when attempting to construct relatively sharp angles using unidirectional carbon fibers that create a rectangular beam, a bladder mold on the outside of the part will cause the unidirectional fibers to shift away from a sharp angle to more of a gradual angle thereby making the shape more curved than desired with the present disclosure. In some implementation, the carbon fiber AFO of the present disclosure has moved away from these traditional manufacturing processes and instead uses the aforementioned compression molding techniques to overcome these traditional challenges associated with the manufacture of carbon fiber. The benefits of this process for embodiments of the present disclosure enable improved dimensional consistency from part-to-part that is essentially identical to the way the AFO was intended. Additionally, relatively small radiuses and curves, as well as rectangular box shapes are now possible through use of this process.

Figure 3G:
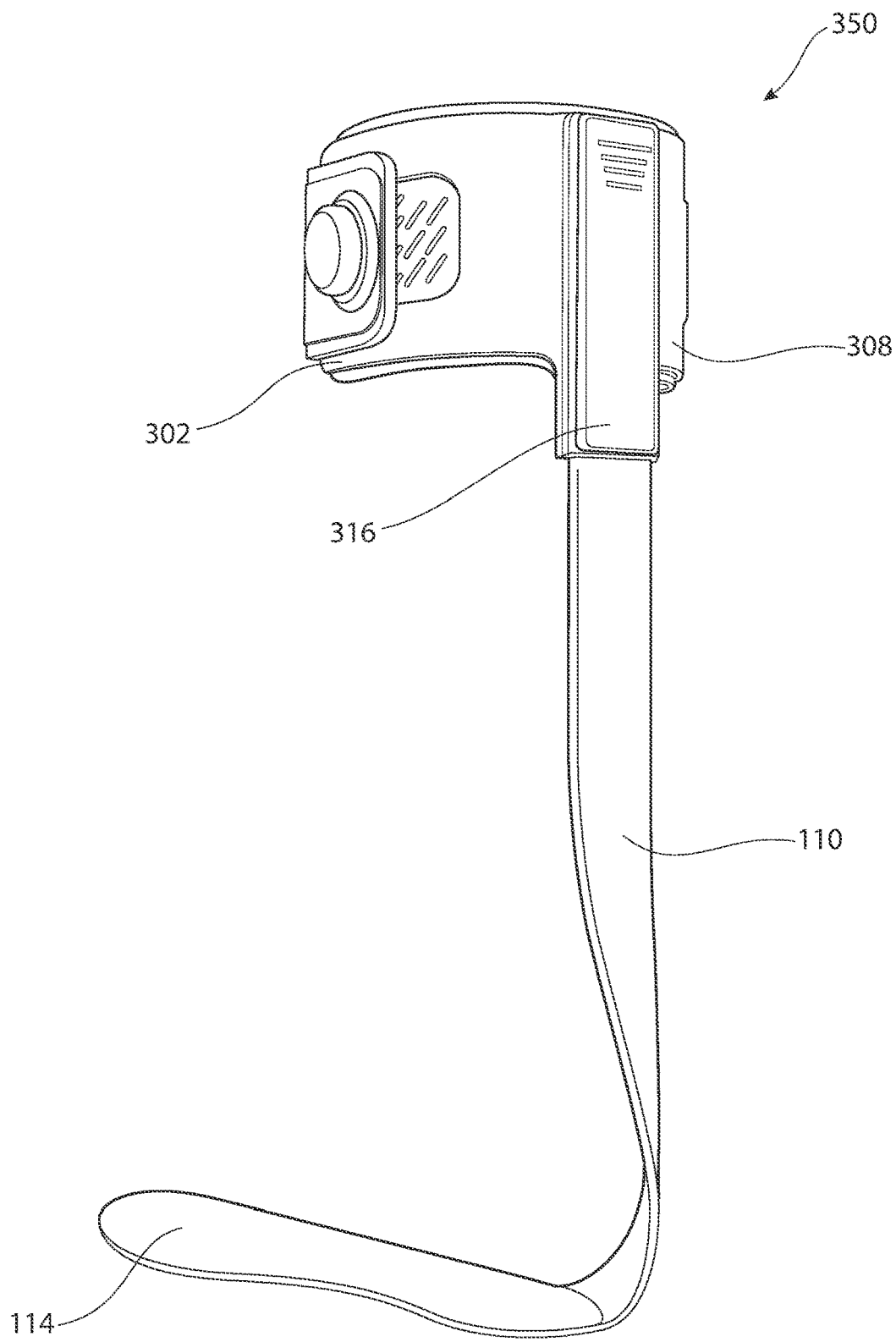

Referring again to the figures disclosed herein, the adjustable portion (332, FIG. 3I) of the strut 110 may consist of a straight (flat) section of carbon fiber that enables a wide range of adjustability in height for the rear cuff 308. For example, in some implementations, the adjustable/straight portion (332, FIG. 3I) of the strut 110 may be approximately 126 mm (5.0 inches) in length, thereby enabling the AFO 350 to accommodate users having a height ranging from approximately 1.5 m (4 foot, 10 inches) to 2.0 m (6 foot, 7 inches), dependent upon variations in tibial length for individual ones of these users, within a single AFO device 350. Accordingly, in some implementations, the overall height of the strut 110 may be approximately 286 mm (11.3 inches). The rear cuff 308 may also include a height adjustment mechanism 316, such as those described elsewhere herein. For example, the height adjustment mechanism 316 may enable discrete height adjustment for the AFO 350 (e.g., every 20 mm (0.8 inches)) or may enable infinite height adjustment, over the length (or vast majority of the length) of the adjustable portion (332, FIG. 3I) of the strut 110, through use of a set screw, etc. as described elsewhere herein. In some implementations, the rear cuff 308 may include a single adjustment point 316 which enables an increased amount of adjustability over the adjustable portion (332, FIG. 3I) of the strut 110 as compared with a comparable AFO with multiple adjustment points. For example, and referring specifically to FIG. 3G, if the AFO 350 included a second adjustment mechanism (similar to adjustment mechanism 316) at the top of the rear cuff 308, the maximum height adjustability for the AFO 350 would be less when using a comparable strut 110, as compared with the embodiment illustrated in FIG. 3G. In other words, because the theoretical height adjustment mechanism would be present at the top of the rear cuff 308 (as opposed to the center/bottom portion as illustrated in FIG. 3G), the rear cuff 308 would not be able to take advantage of the full range of motion enabled by the adjustable portion (332, FIG. 3I) of the strut 110.

In some implementations, the overall height of the AFO 300 depicted in FIGS. 3F-3J may range from between 295 mm (11.6 inches) to 384 mm (15.1 inches), or may range from between 320 mm (12.6 inches) to 365 mm (14.4 inches). Although specific dimensions have been provided herein, it would be appreciated by one of ordinary skill given the contents of the present disclosure that these specific dimensions may be varied dependent upon the specifics of the AFO design. Rather, it is a primary goal of embodiments of the present disclosure for the posterior AFO 350 to incorporate a spiral strut 110 design that allows for height adjustability that can accommodate patient sizes from XS to XXXL. Moreover, it would be appreciated the specific dimensions described herein have been primarily discussed in the context of adult human beings, and that similar variability to accommodate various sizes are also possible with other populations of individuals such as, for example, children (pediatrics) or other populations of individuals which have a range other than the aforementioned 1.5 m (4 foot, 10 inches) to 2.0 m (6 foot, 7 inches).

The front cuff 302 as well as the rear cuff 308 may include a padded liner on its interior, thereby further facilitating comfort and support for the wearer. Padded inserts may be included that may attach to the front cuff 302 using, for example, hook and loop fasteners that enables the front cuff 302 to accommodate different anatomies. Cut-outs 312 along with apertures located on the rear cuff 308 may assist with breathability for the AFO 300 and comfort for the wearer. The rear cuff 308 may attach to the front cuff 302 using cutouts 312, using the mechanism described with reference to, for example, FIG. 2D described herein. A rotary tensioning mechanism 104 may be utilized in order to tighten (or loosen) the combination of the front cuff 302 and the rear cuff 308 around the wearer's calf thereby facilitating easy donning and doffing. The rotary tensioning mechanism 104 (or separate rotary tensioning mechanism 104) may also be utilized in combination with a support strap (not shown) to support various varus and/or valgus deformities present with the wearer as described elsewhere herein.

Figure 3H:
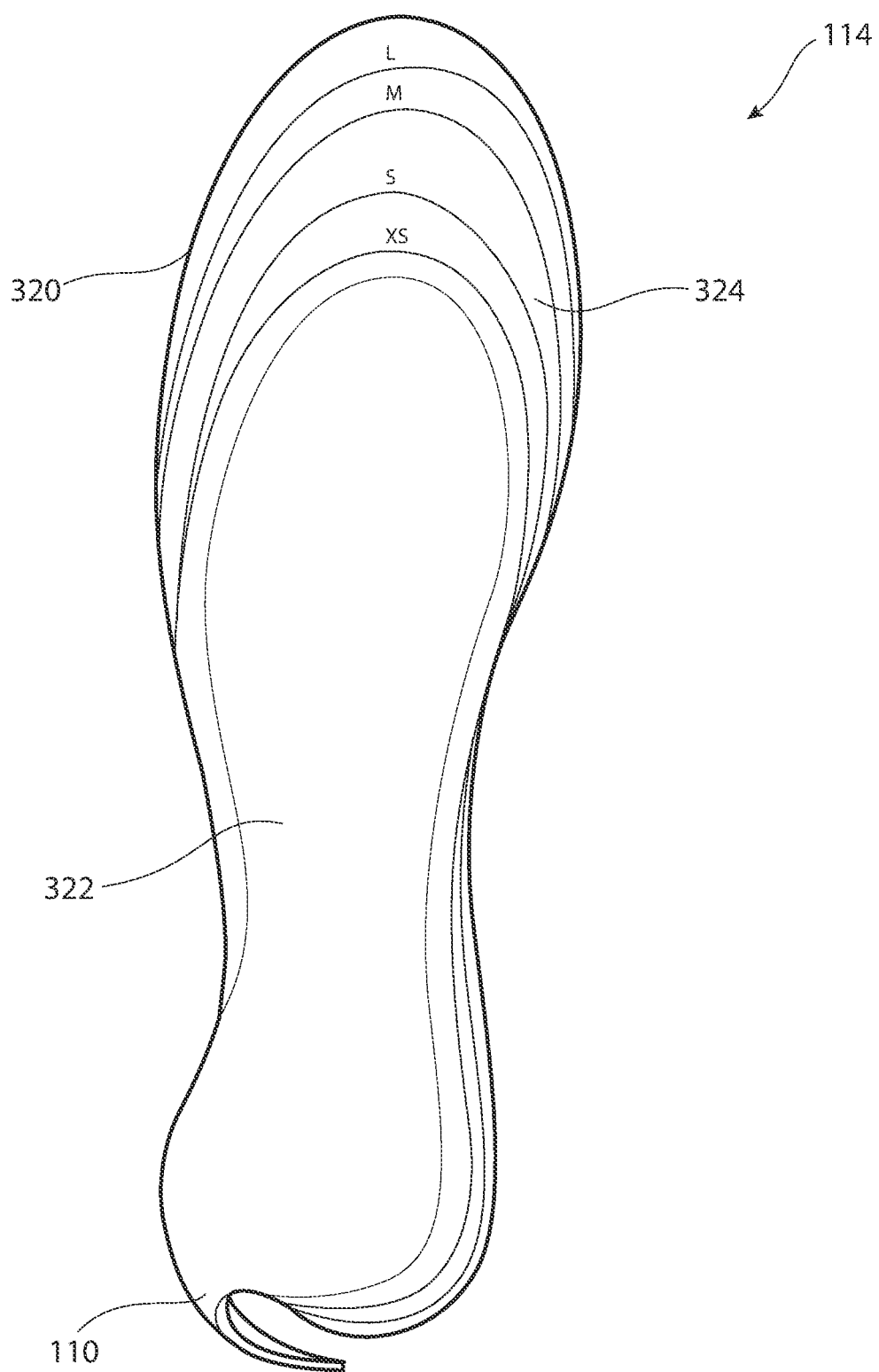
Figure 31:
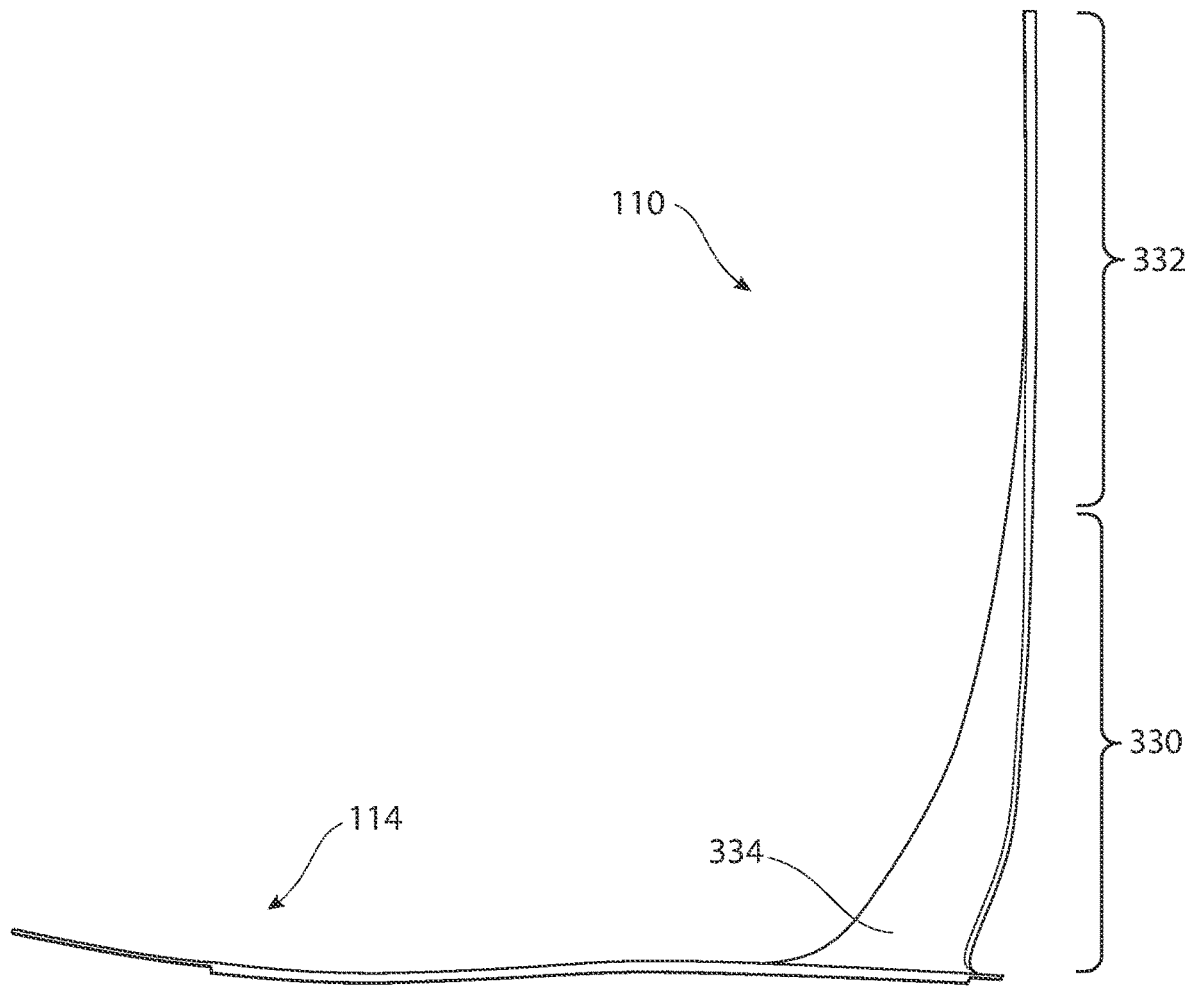

Referring now to FIG. 3H, an exemplary foot plate 114 is shown for use with, for example, the AFO 350 shown in FIGS. 3E-3H. The foot plate 114 may include a non-trimmable portion 322 that is coupled with the strut 110 as well as a trimmable portion 320 which surrounds much of the periphery of the non-trimmable portion 322. In some implementations, the non-trimmable portion 322 is manufactured from carbon fiber, while the trimmable portion 320 is manufactured from glass fiber. The trimmable portion 320 may be thinner in thickness than the non-trimmable portion 322 so as to provide, inter alia, a visual queue for the trimmable area 320 (i.e., a visual indication as to which areas may be trimmed). See also FIG. 3I which illustrates a side profile of the foot plate 114. The transition area between the thinner trimmable portion 320 and the thicker non-trimmable portion 322 may include a fillet (or concaved junction), which strengthens the overall foot plate 114 design by minimizing areas of weakness. In other words, by including the fillet the trimmable portion 320 is less susceptible to unintentional fracture (and breaking off) from the non-trimmable portion 322 of the foot plate 114. The foot plate 114 may also include trim lines 324 which may be, for example, applied to the external surface of the foot plate 114. These trim lines 324 may, for example, depict a range of sizes (e.g., from XS to L, shoe size ranges, etc.). In some implementations, the foot plate 114 may be constructed in accordance with the embodiment described with reference to FIGS. 6A and 6B described infra.

In some implementations, the overall length of the foot plate 114 may be approximately 305 mm (12 inches), while the non-trimmable portion 322 may have an overall length of approximately 228 mm (9 inches). In the area towards the wearer's toes (i.e., the forefoot region), the trimmable portion 320 may have a maximum length of up to about 60 mm (2.4 inches), while the area near the heel of the wearer (i.e., the hindfoot region), the trimmable portion 320 may have a maximum length of up to about 13 mm (0.5 inches). In some implementations, the overall periphery of the non-trimmable portion 322 may mimic an extra-small foot, while the overall periphery of the trimmable portion 320 may mimic an extra-large foot. In some implementations, the non-trimmable portion 322 may provide support to the metatarsal region of the wearer, even when the wearer has an extra-large foot size.

Figure 3J:
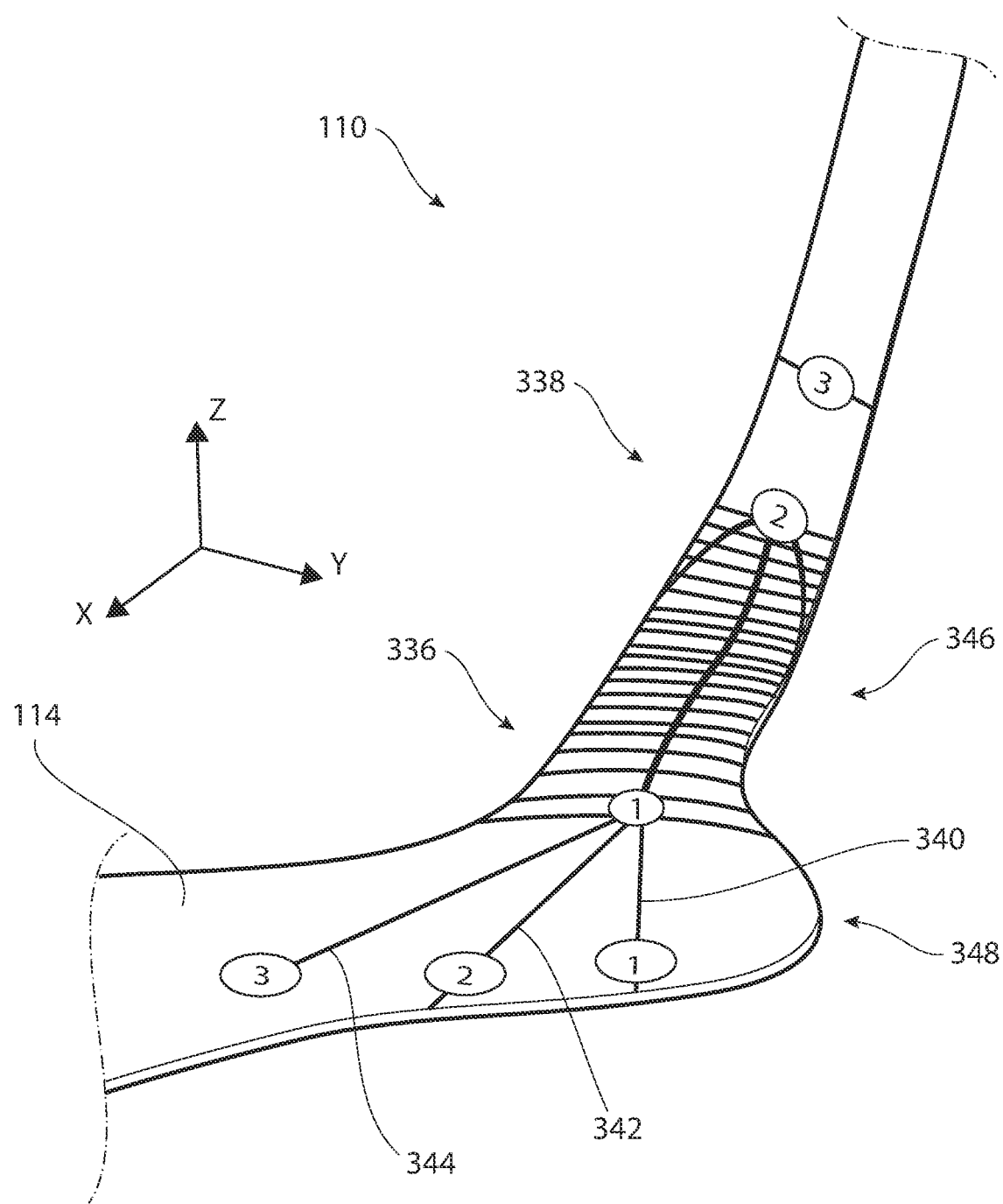

Referring now to FIG. 3J, the curvature of the strut 110 for the posterior AFO 350 that provides comfort, enables improved gait, and improves durability is shown and described in detail. For purposes of illustration, the strut 110 illustrated in FIG. 3J has been divided into three zones, namely zone "1", zone "2", and zone "3". For consideration of comfort, in zone "1", the radius of curvature in the X-Y plane near the rear portion 346 of the strut 110 is smaller than the radius of curvature in the X-Y plane near the front portion 336 of the strut. For example, in some implementations the rear portion 346 of this interface between strut 110 and foot plate 114 may have a radial dimension of approximately 32 mm (1.3 inches), while the front portion 336 of this interface between strut 110 and foot plate 114 may have a radial dimension of approximately 82 mm (3.5 inches). A portion between the rear 346 and front portions 336 may have radial dimension between these dimensions (e.g., 71 mm (2.8 inches)). Initially, it was unclear to the assignee of the present disclosure how the interface between the strut 110 and foot plate 114 could be made comfortable for both patients with extra-large feet as well as patients with extra-small feet, especially when the AFO 350 is worn within the patient's shoes. However, through extensive experimentation, this was accomplished in part via the trimmable portion of the foot plate at the back of the heel 348 of the foot plate 114 which results in the heel of a wearer with extra-small feet being positioned further forward on the foot plate 114 than the heel of a wearer with extra-large feet within the AFO 350. In other words, the radius of curvature towards the rear portion 346 of the strut 110 is intended to more completely surround the heel of an extra-small foot as compared with an extra-large foot where the strut 110 is positioned further forward on the heel of the extra-large foot.

In terms of improved gait, when a patient wearing the AFO 350 goes into heel strike and push off, energy stored within the strut 110 during heel strike is released at push off aiding in patient ambulation. The force vector direction driven from the energy storage is perpendicular to the lines displayed on the orthosis for each zone (i.e., zone "1" releases energy along line "1" 340, zone "2" releases energy along line "2" 342, and zone "3" releases energy along line "3" 344, etc.). It has been found by the assignee of the present disclosure that more efficient gait is achieved where the line of progression travels from the center of the heel moving laterally relative to the midline of the foot and then around the metatarsals contacting the floor where the center of pressure turns medially between the first and second metatarsal. As depicted in FIG. 3J by the direction of the lines of force vectors 340, 342, 344 on the AFO 350, the lines of curvature on the strut 110 directs the medial shift of the center of pressure as well as the tibia progression by providing energy propulsion of the strut 110 at push off into a medial direction.

When considering durability of the AFO 350 the assignee of the present disclosure has found that increasing the area of flexibility along the strut 110 drastically reduces the stress on the strut 110/foot plate 114 of the AFO 350. This is accomplished by ensuring that the effective radius in the x-y plane in zone "1" is relatively large where the stress is the highest to significantly strengthen that interface area between the strut 110 and foot plate 114. However, when traveling up 338 the strut 110 in the z-direction, the radius of curvature progressively flattens until the strut 110 becomes completely flat in zone "3". What this ultimately accomplishes is a very large flex area in the upper portion of the strut 110 where the stresses are lower, thereby significantly increasing the durability of the strut 110 and AFO 350. It will be appreciated that while specific dimensions described herein have been primarily discussed in the context of adult human beings, similar variability to accommodate various size ranges are also possible with other populations of individuals such as, for example, children (pediatrics) or other populations of individuals which have a range other than the aforementioned typical adult sizes described herein.

Figure 4A:
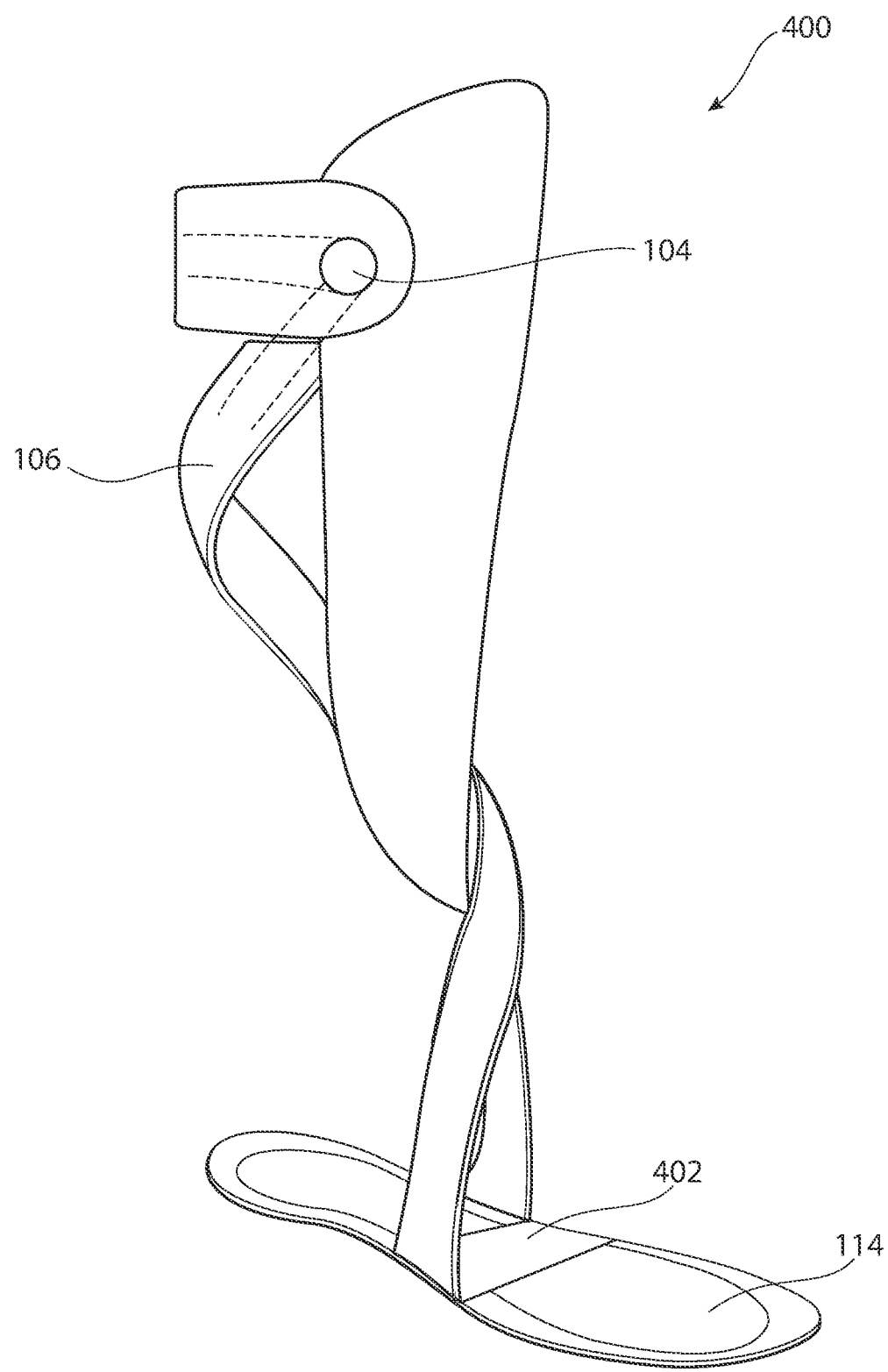
FIGS. 4A-4B are perspective views of an exemplary anterior AFO device, in accordance with the principles of the present disclosure.
Figure 4B:

Referring now to FIGS. 4A-4B, a variation to an AFO 400 is illustrated that can be used in combination with the other orthoses or AFO embodiments described herein. For example, FIGS. 4A and 4B illustrate an anterior AFO embodiment in which the support strap 106 is attached to the foot plate 114 on the lateral side. The support strap 106 runs along the top of the foot plate 114 to the medial side. Accordingly, the section 402 of the support strap 106 is positioned between the wearer's foot and the foot plate 114. Such a variant may be desirable as the section 402 of the support strap 106 will conform to the wearer's foot when tightened. From there, the support strap 106 will spiral up the wearer's leg and attach to, for example, a rotary tensioning mechanism 104 located on the medial side of the wearer's leg. Such an illustrated embodiment provides both dorsiflexion and plantar flexion support for the wearer of the AFO 400. This support strap 106 may also attach independently to the tibia shell. To provide additional support to the ankle a heel strap can be provided which attaches to the back of the footplate at the heel section on top of the footplate, spirals around the calcaneus and over the dorsum of the foot to attach to the first spiral strap. This provides more complete capture around the entire arch, midfoot and calcaneus.

Exemplary Foot Plate Variants

Figure 6A:
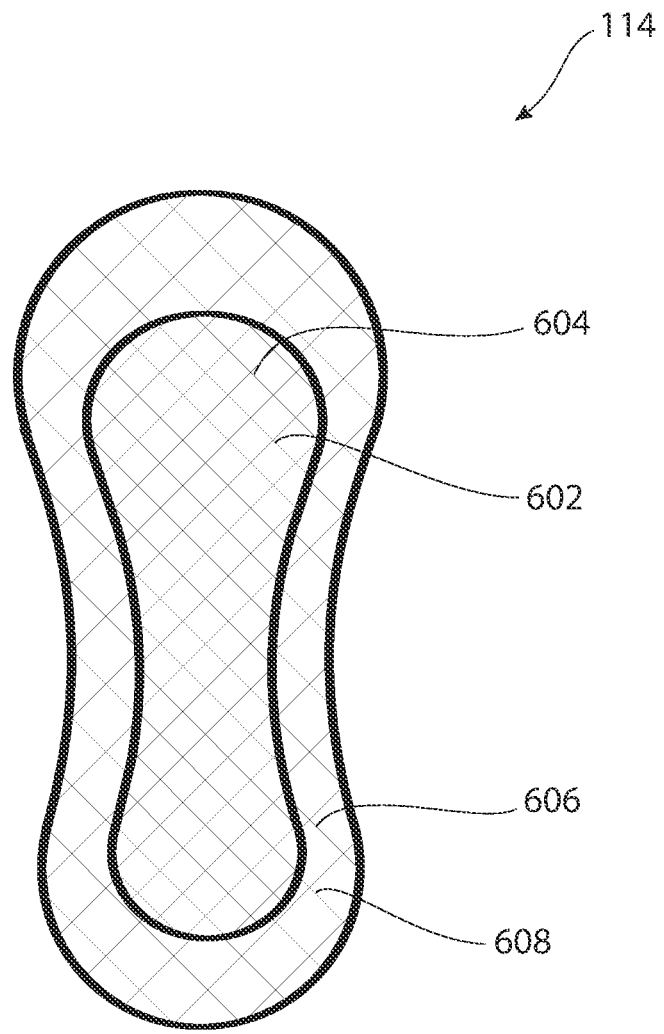
FIG. 6A is a top plan view of an exemplary foot plate, in accordance with the principles of the present disclosure.
Figure 6B:
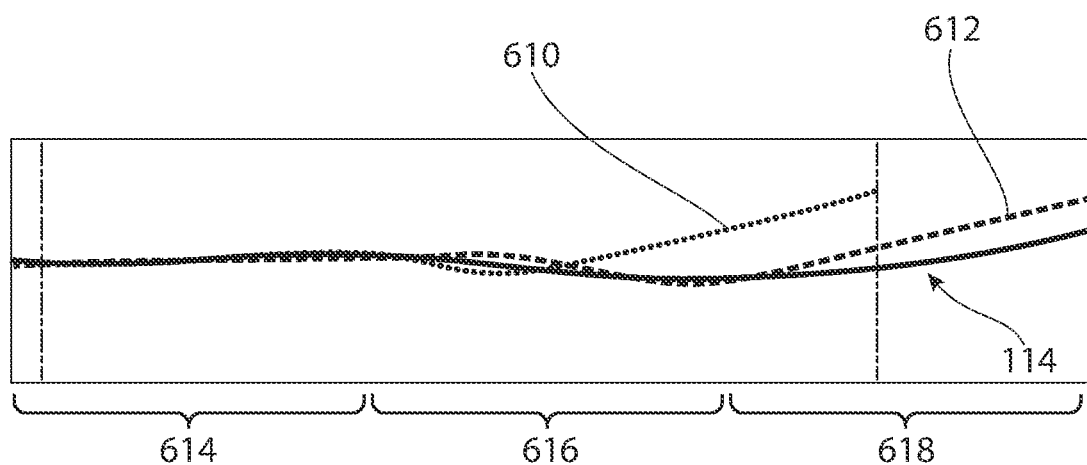
FIG. 6B is a side view of the exemplary foot plate of FIG. 6A shown in comparison with prior art foot plate designs, in accordance with the principles of the present disclosure.

Referring now to FIG. 6A-6B, one exemplary foot plate 114 is shown and described in detail. The foot plate 114 may include two (or more) different composite materials. For example, one section 602 may be manufactured from a rigid composite material (e.g., carbon fiber), while the other section 606 may be manufactured from a trimmable composite material (e.g., a fiber glass material). The individual strands 604, 608 of these composite materials may be oriented at an angle as illustrated in FIG. 6A. This angle may be at 45° with respect to the lengthwise direction (or the line of progression) of the foot plate 114 to reduce the stiffness and brittleness in the interface between the two section 602, 606. The angle of orientation of the fibers (or strands) 604, 608 makes the underlying composite material more durable as compared with a similar foot plate in which the underlying strands are oriented parallel (and orthogonal with) the lengthwise direction of the foot plate. In some implementations, this angle of orientation may be maintained consistent with the outline of the rigid composite material 602. In some implementations, the transition between the two sections 602, 606 will further include a smooth radius that, in combination with the angular oriented strands, prevents accidental cracking caused by tension applied to the foot plate 114 during use by the wearer.

Referring now to FIG. 6B, a side view of the exemplary foot plate 114 is illustrated along with a prior size extra-small foot plate 610 and a prior extra-large foot plate 612. Various features of the foot plate 114 are now described which enable the foot plate 114 to accommodate a variety of sizes (e.g., from extra-small to extra-large) for various wearers of the orthosis. Specifically, anthropometric data is taken from the anatomy of a population of diverse individuals in accordance with three planes. For example, these three planes may be the transverse plane, the frontal plane, and the sagittal plane. Traditionally, the sagittal plane is an anatomical plane which divides the body into right and left parts. However, the anthropometric data may be taken along multiple planes that are parallel with the sagittal plane. Moreover, the transverse plane traditionally divides the body into the top and bottom halves while the frontal plane divides the body into the front and back parts of the body. Similar to the sagittal plane example set forth above, anthropometric data may be taken along multiple planes that are parallel with both the transverse and frontal planes with the primary concern for the foot plate 114 being the wearer's foot. The foot plate 114 may take the average of all (or a statistically meaningful subset) of all wearer's in order to provide for a universal (one-size fits all) anatomically correct foot plate 114. Accordingly, a single profile that does not cause discomfort to the user while providing the needed support for a variety of users can be created. Moreover, because some implementations of the foot plate 114 are trimmable, the foot plate 114 may provide for exact adjustable sizing in the transverse and frontal planes, while being average in the sagittal plane.

The foot plate 114 may be thought of as being divided into three functional sections, namely the: (1) heel section 614; (2) mid-foot section 616; and (3) forefoot section 618. The heel section 614 may slope slightly upward (or remain relatively flat) as you move from the posterior portion towards the anterior portion of the user's foot. The mid-foot section 616 may start to slope slightly downward as you move from the posterior portion of the mid-foot section 616 towards the anterior portion of the user's foot. The forefoot section 618 may in turn slope slightly upward as you move from the posterior portion of the forefoot section 618 towards the anterior portion of the user's foot. Another advantage of the foot plate 114 may be seen from the view shown in FIG. 6B. Specifically, the angle of slope for the forefoot section 618 may be less than that of corresponding prior art foot plates which may provide for greater energy return and support during the entire gait cycle as compared with prior footplates 610, 612. In other words, as the incline for the foot plate 114 (in particular the forefoot section 618) is less than prior footplate designs 610, 612 (i.e., less than about ten degrees (10°)), the illustrated profile for the foot plate 114 provides increased support as the foot moves from dorsiflexion to plantar flexion for the user of the orthosis.

Figure 7:
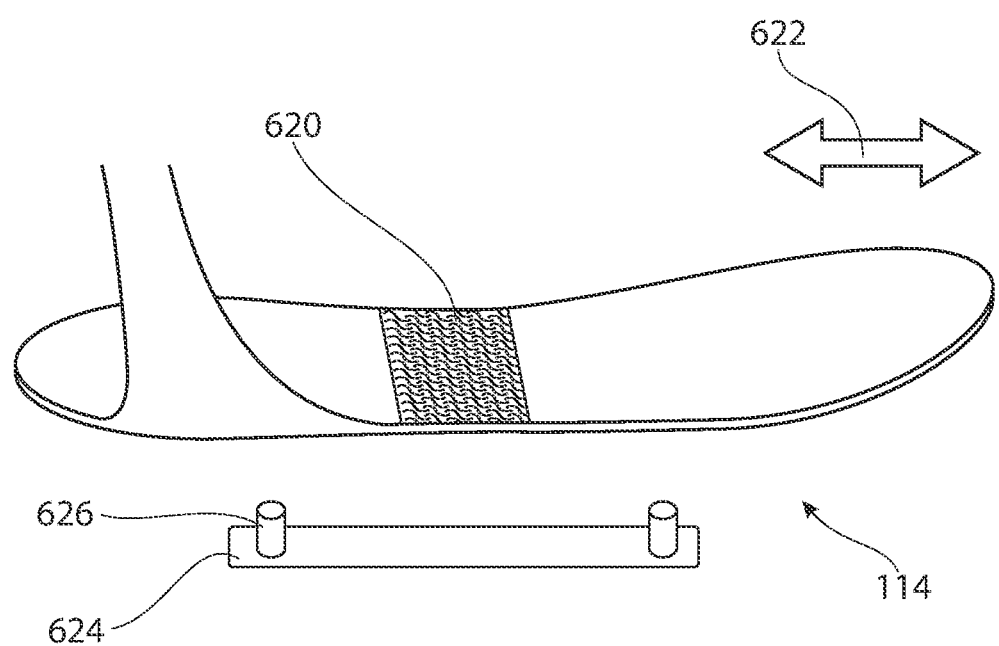
FIG. 7 is a perspective view of another exemplary foot plate, in accordance with the principles of the present disclosure.

Referring now to FIG. 7, another implementation of a foot plate 114 is shown and described in detail. The foot plate 114 includes an accordion-like material 620 near the mid-foot region. This accordion-like material 620 allows the length of the foot plate 114 to lengthen or shorten when the forefoot region of the foot plate 114 is pulled (or shortened) away (or towards) the heel section of the foot plate 114 generally in direction 622. For example, via use of the accordion-like material 620, the foot plate 114 can be sized from an extra-small all the way up to an extra-large size with varying degrees of granularity from the extra-small and extra-large sizes. In some implementations, the edges of the foot plate 114 may remain trimmable as is discussed elsewhere herein (see e.g., FIGS. 2E-2F). The foot plate 114 may also include a locking strut 624 which enables a desired size to remain fixed via use of snap features 626 that interface with respective features located on the bottom (and/or top) of the foot plate 114. The specific implementations of the foot plate 114 described herein with respect to FIGS. 6A-7 may be utilized in combination with various ones of the orthoses described herein with respect to FIGS. 1A-4B.

Figure 9A:
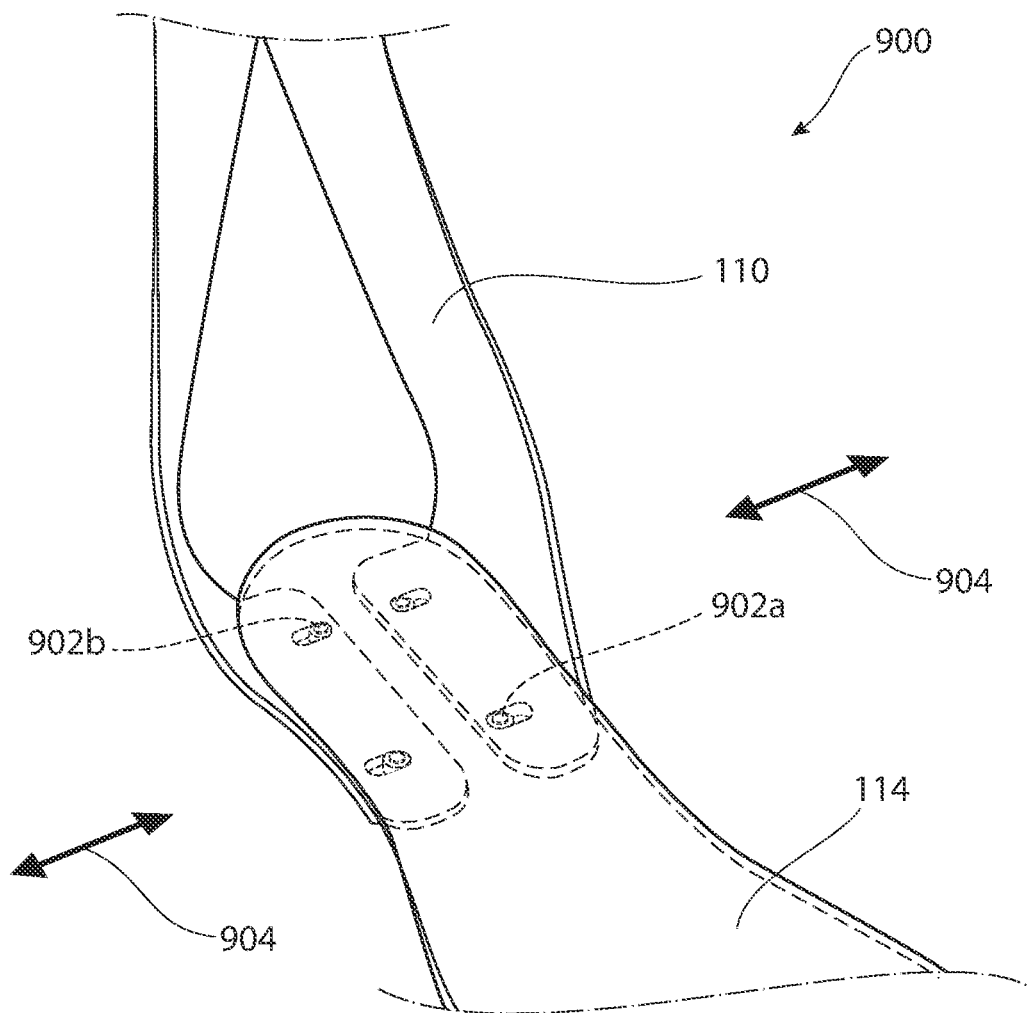
FIG. 9A is a perspective view of a plastic AFO illustrating how the two struts slide on a footplate to accommodate different widths, in accordance with the principles of the present disclosure.

Referring now to FIGS. 9A-9D, one exemplary so-called plastic AFO 900 is shown and described in detail. Referring to FIG. 9A, the AFO 900 includes a foot plate 114 as well as a strut 110. The strut 110 may be coupled to the foot plate 114 at front attachment points 902a which are positioned farther away from the back/heel of the foot plate 114 than the rear attachment points 902b. That attachment points 902 enable the width of the two strut arms 110 to be adjusted to accommodate different anatomies. For example, front attachment points 902a and rear attachment points 902b enable the strut arms 110 to be positioned closer to one another generally along direction 904. As but another non-limiting example, front attachment points 902a and rear attachment points 902b enable the strut arms 110 to be positioned farther from one another generally along direction 904. As but yet another non-limiting example, front attachment points 902a and rear attachment points 902b enable the strut arms 110 to be adjusted independently (e.g., front attachment points 902a may be adjusted differently than the adjustment of the rear attachment points 902b). Such adjustability enables the AFO 900 to be adapted to a wide variety of patient anatomies.

Figure 9B:
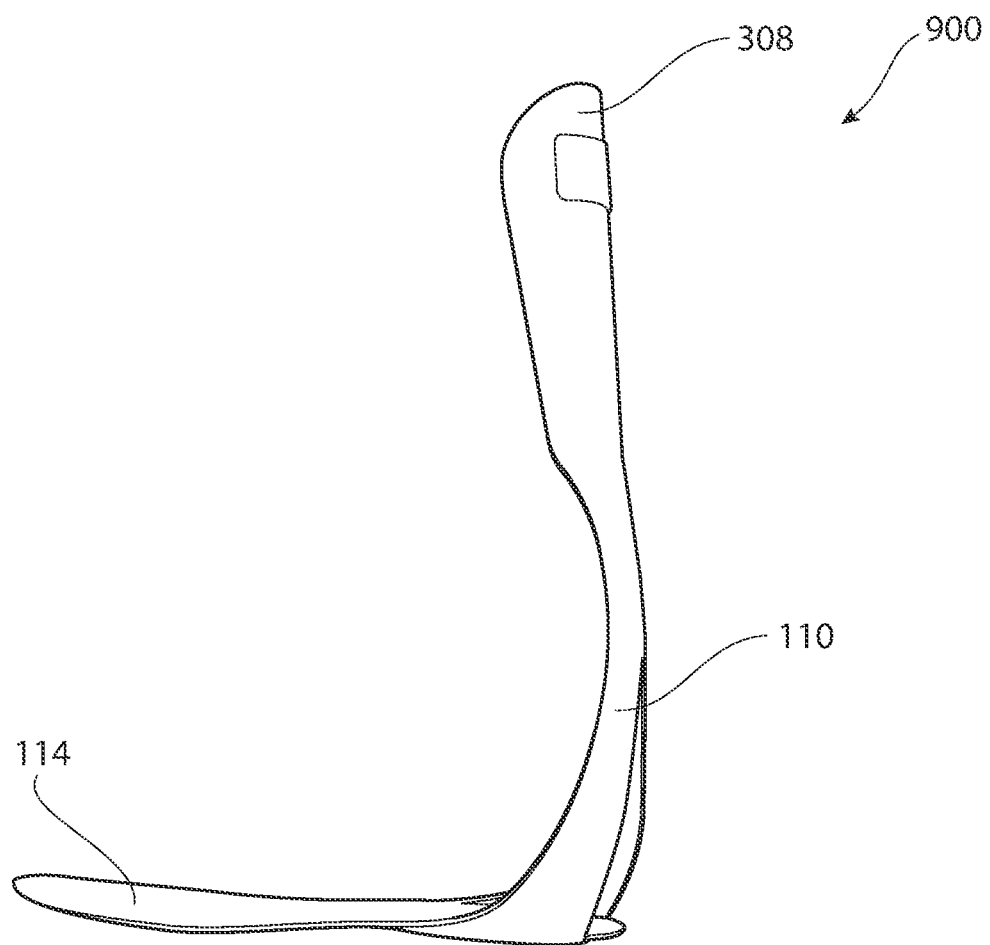
FIG. 9B illustrates the AFO of FIG. 9A from a side perspective, in accordance with the principles of the present disclosure.
Figure 9C:
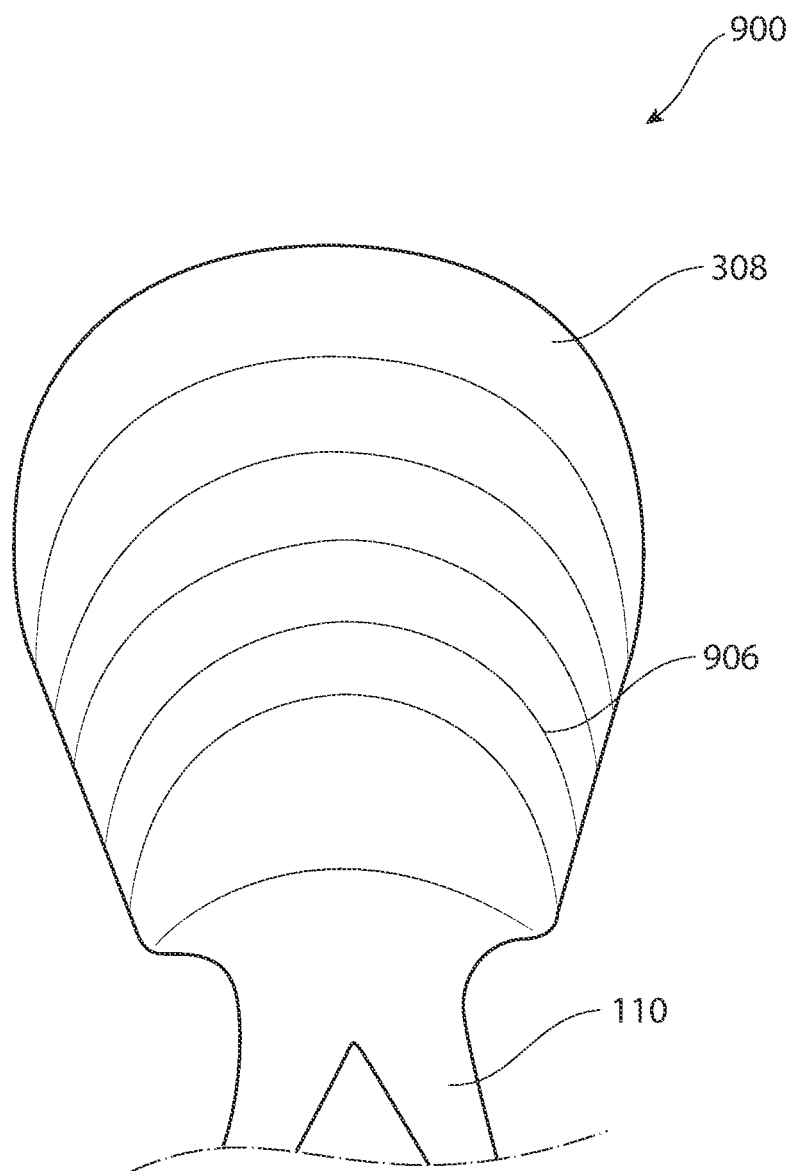
FIG. 9C illustrates the trimlines in the calf section of the AFO of FIG. 9A, in accordance with the principles of the present disclosure.

Referring now to FIGS. 9B and 9C, the AFO 900 may include a foot plate 114, a strut 110, and a rear cuff 308. In some implementations, the rear cuff 308 may be formed integrally with the struts 110 during manufacture (as depicted in FIG. 9B), although it would be readily apparent given the contents of the present disclosure that these components (strut 110 and rear cuff 308) may be manufactured independently from one another in some variants. The rear cuff 308 as depicted in FIG. 9C may include a plurality of trim lines 906. These trim lines 906 provide a visual queue as to where material may be removed from the rear cuff 308 using, for example, a pair of scissors, a rotary cutting disk, and other suitable types of trimming tools. The plastic AFO 900 may be manufactured from various polymers or copolymers such as, for example, polypropylene, acrylonitrile butadiene styrene (ABS), and/or other suitable types of polymers or copolymers. The material underlying the plastic AFO 900 enables the rear cuff 308 to be trimmed to accommodate a variety of differing patient anatomies. Accordingly, in some implementations, the combination of the adjustable width strut arms 110 and the trimmable rear cuff 308 enable the AFO 900 to accommodate a wide variety of patient anatomies.

Figure 9D:
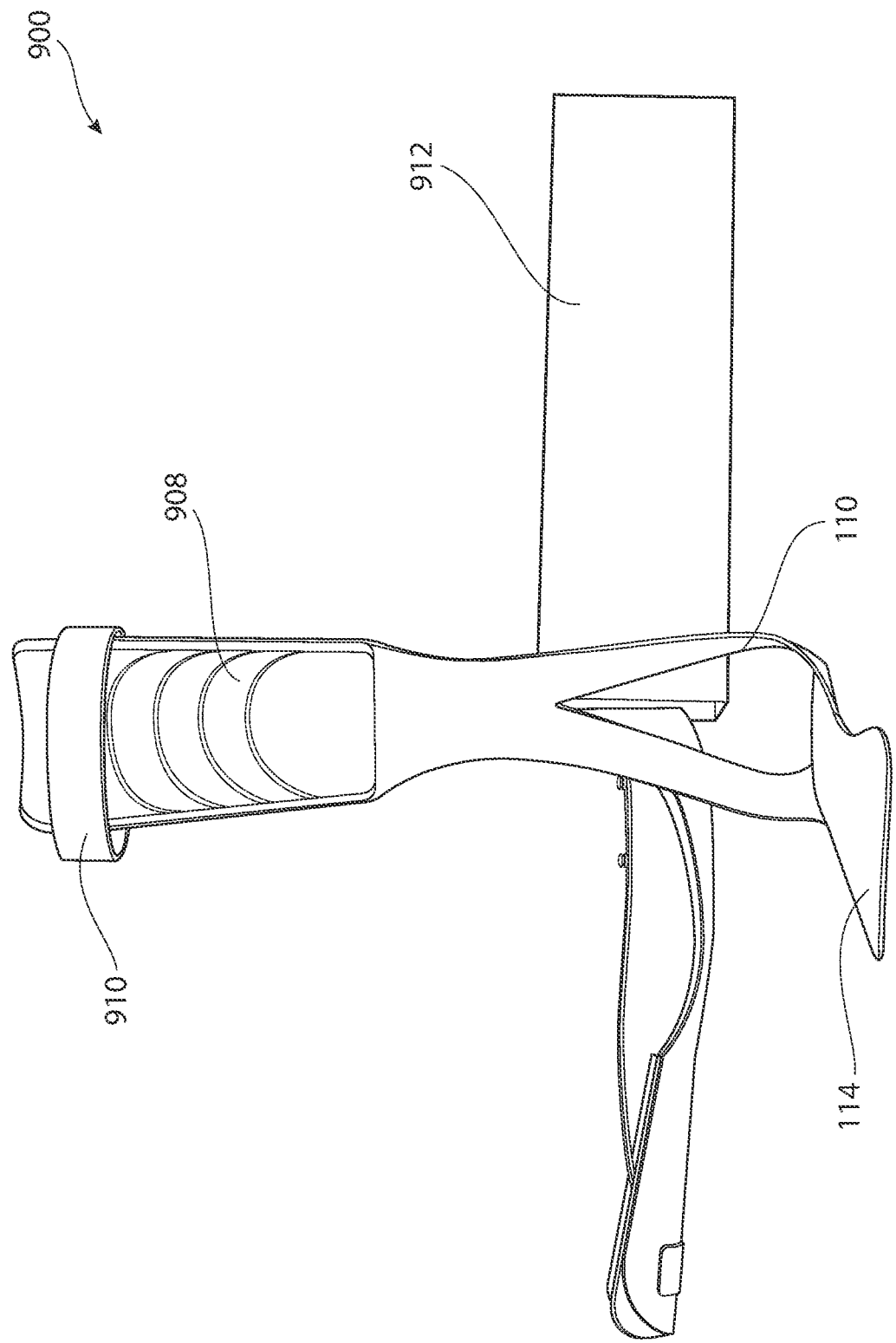
FIG. 9D is a perspective view of the AFO of FIG. 9A illustrating that the foot plate may be separable from the calf section in order to package the AFO in a manner that further reduces inventory space, in accordance with the principles of the present disclosure.

Referring now to FIG. 9D, the AFO 900 may include a padded line 908 that may also be trimmed to accommodate modifications to the rear cuff 308 as well as one or more straps 910 that enable the AFO 900 to be secured to a patient's leg. Another advantage of the attachment points between the strut 110 and foot plate 114 is also depicted in FIG. 9D, namely the ability for the strut 110 and foot plate 114 to be separated from one another so that it may be packaged in a box 912 that minimizes inventory space within, for example, a treating physician's offices. In some implementations, the foot plate 114 may also be trimmable as is described elsewhere herein so that a single AFO 900 can be utilized to accommodate both right and left legs of patients having a variety of anatomical differences (see also discussion of FIG. 11 infra). In some implementations, the foot plate 114 may be trimmable so that a left-leg and right-leg variant of the AFO 900 can be utilized to accommodate patients having a variety of anatomical differences (see also, for example, the discussion of FIGS. 2E, 2F, 3D and 3H supra). These and other variants would be readily apparent to one of ordinary skill given the contents of the present disclosure.

Figure 11:
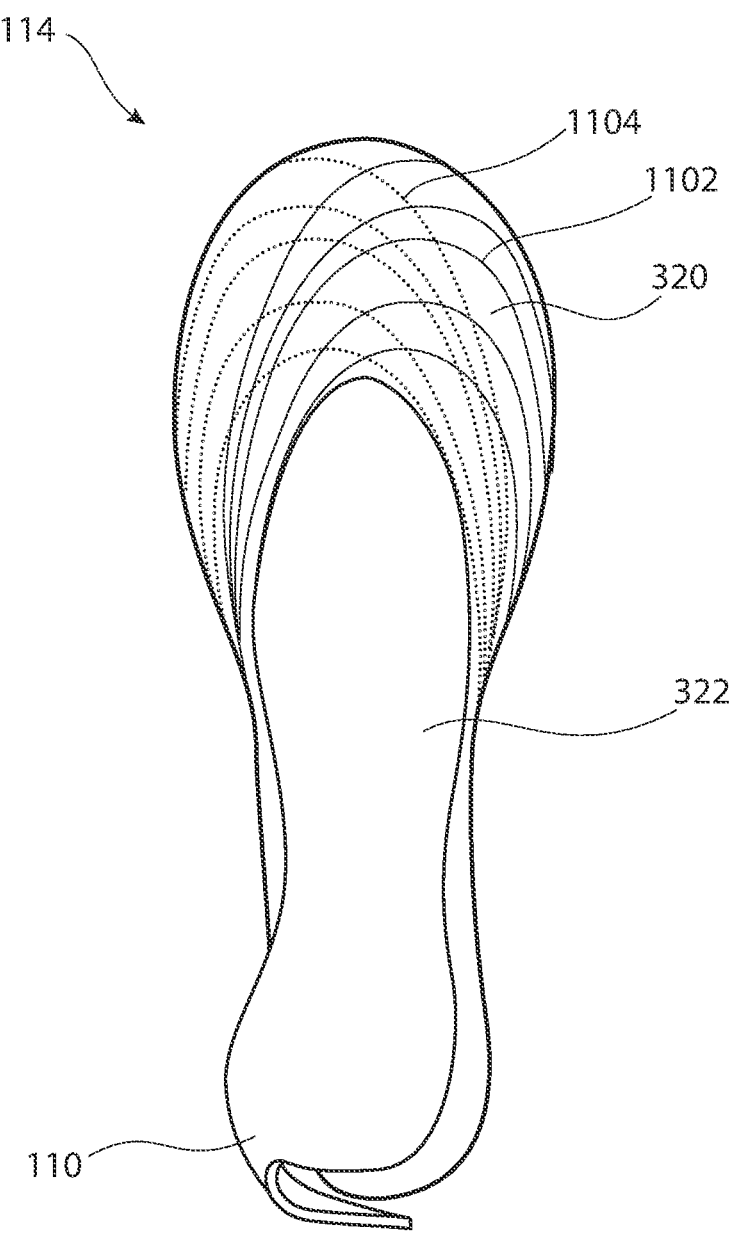
FIG. 11 is a bottom plan view of a trimmable foot plate that can accommodate both left and right feet, in accordance with the principles of the present disclosure.

Referring now to FIG. 11, another exemplary foot plate 114 is shown and described in detail. Similar to other foot plate configurations described herein, the foot plate 114 may include a non-trimmable portion 322 that is coupled with the strut 110 as well as a trimmable portion 320 which surrounds much of the periphery of the non-trimmable portion 322. In some implementations, the non-trimmable portion 322 is manufactured from carbon fiber, while the trimmable portion 320 is manufactured from glass fiber. The trimmable portion 320 may be thinner in thickness than the non-trimmable portion 322 to provide, inter alia, a visual queue for the trimmable area 320 (i.e., a visual indication as to which areas may be trimmed). The transition area between the thinner trimmable portion 320 and the thicker non-trimmable portion 322 may include a fillet (or concaved junction), which strengthens the overall foot plate 114 design by minimizing areas of weakness. In other words, by including the fillet the trimmable portion 320 is less susceptible to unintentional fracture (and breaking off) from the non-trimmable portion 322 of the foot plate 114.

The foot plate 114 of FIG. 11 includes two sets of trim lines 1102, 1104. The first set of trim lines 1102 enable trimming for a right-foot, while the second set of trim lines 1104 enable trimming for a left-foot. Herein lies a salient advantage of the foot plate 114 illustrated in FIG. 11, namely the ability for, for example, a treating physician to stock a single AFO variant that may be utilized on either the left or right leg of a patient. In the embodiment illustrated in FIG. 11, the spiral strut 110 is positioned on a lateral side of the patient's leg when worn on the right leg of the patient, while the spiral strut 110 is positioned on a medial side of the patient's leg when worn on the left leg of the patient. Other variants are also envisaged whereby the spiral strut 110 is positioned on a medial side of the patient's leg when worn on the right leg of the patient, while the spiral strut 110 is positioned on a lateral side of the patient's leg when worn on the left leg of the patient. Moreover, while illustrated as being incorporated into a posterior AFO, it would be readily apparent to one of ordinary skill given the contents of the present disclosure that the above-referenced "universal" foot plate may be incorporated into an anterior AFO.

Exemplary Modular Strut Variants

Figure 8:
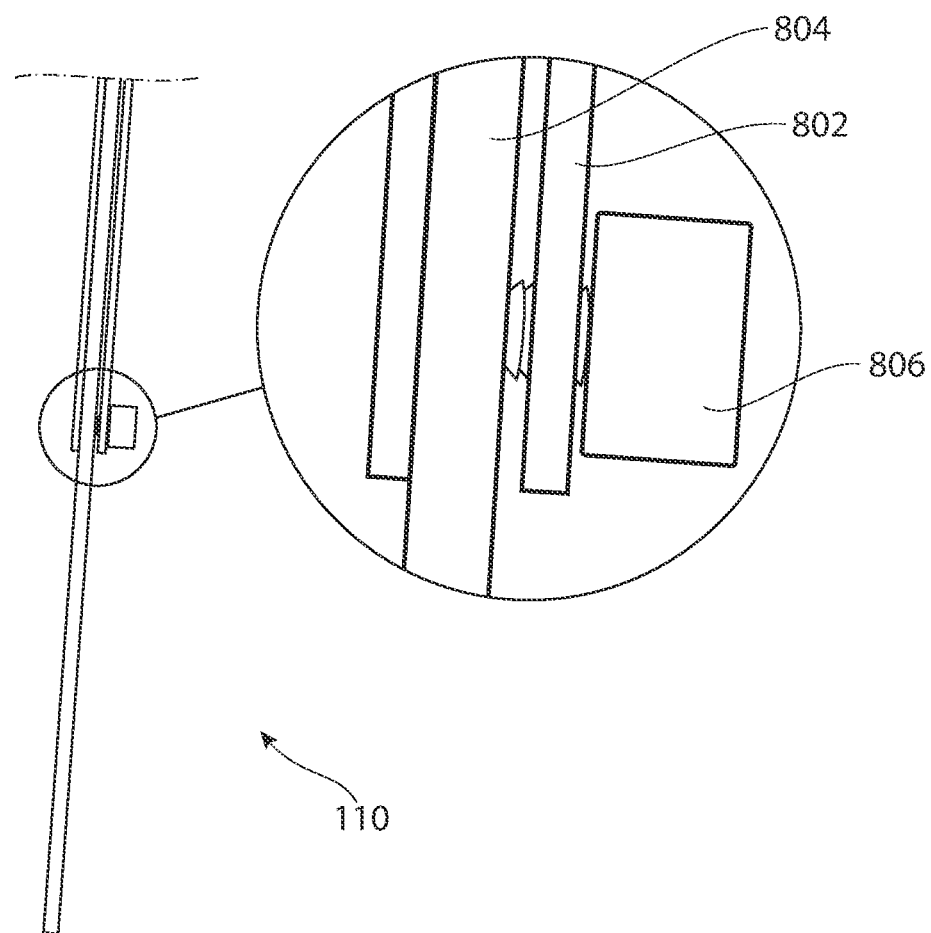
FIG. 8 is a perspective view of one exemplary adjustable strut, in accordance with the principles of the present disclosure.

Referring now to FIG. 8, one exemplary adjustable strut 110 is shown and described in detail. In this implementation, the strut 110 is made up of an inner portion 804 that is received within an outer portion 802. The inner portion 804 of the strut 110 can be adjusted in height as the inner portion 804 is translated with reference to the outer portion 802. Accordingly, this adjustable strut 110 can be sized to accommodate, for example, a variety of tibial lengths for the wearer of the orthosis. In some implementations, the inner portion 804 and the outer portion 802 can be locked into place once a desired height for the strut 110 is achieved through the use of a locking screw 806 that can be manually tightened and loosened in order to achieve the desired height. In some implementations, a detent mechanism can be used in addition to (or alternatively from) the aforementioned locking screw 806. The detent mechanism can be, for example, a ball detent which may typically utilize a sphere that is configured to slide within a bored cylinder and utilizes a spring in order to hold the sphere within a detent in order to temporarily (or even permanently) position the inner portion 804 and outer portion 802 of the strut. In some implementations, the strut may incorporate a rack and pinion to translate the inner portion 804 with respect to the outer portion 802. The inner portion 804 and the outer portion 802 of the strut may be manufactured from carbon fiber, metals, polymers, and/or other suitable materials. For example, the strut 110 may be manufactured from metal or polymer that is co-molded with carbon fiber.

Exemplary Support Strap Variants

Figure 5A:
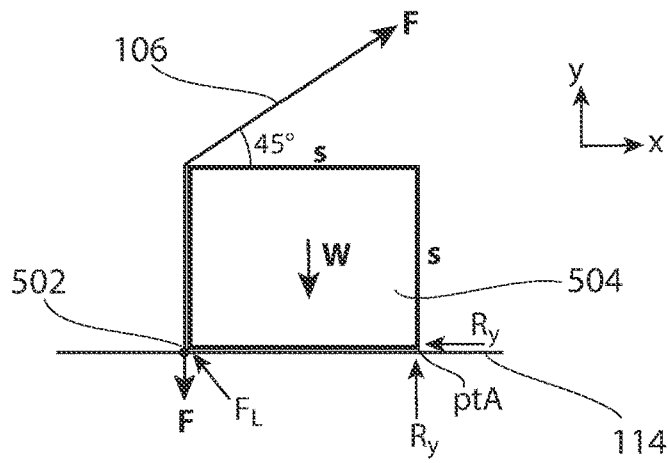
FIG. 5A is a plot of the force required to secure an exemplary varus/valgus strap, in accordance with the principles of the present disclosure.
Figure 5B:
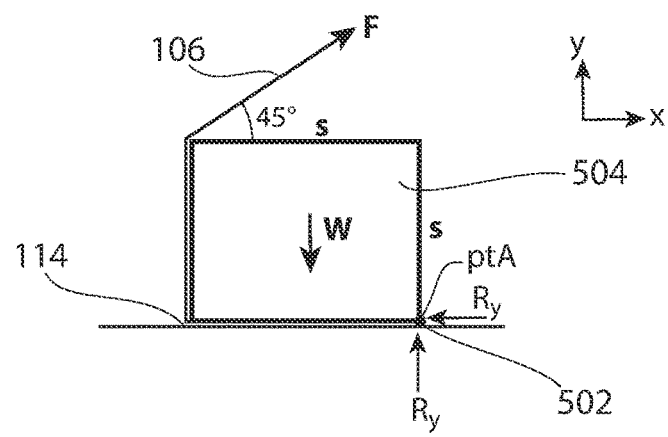
FIG. 5B is a plot of the force required to secure the varus/valgus strap illustrated in, for example, FIGS. 2G-2I, 4A-4B, and 10A-10L, in accordance with the principles of the present disclosure.

Referring now to FIGS. 5A and 5B, the principle of operation of support strap 106 variants are shown and described in detail. FIG. 5A represents a foot 504 positioned on a foot plate 114. In the example of FIG. 5A, the support strap 106 (e.g., a varus/valgus strap) is anchored at anchor point 502 on the foot plate 114 on one side of the foot 504. In the example of FIG. 5B, the support strap 106 (e.g., a varus/valgus strap) is anchored at anchor point 502 on the foot plate 114 on the opposing side of the foot 504 as illustrated in FIG. 5A. In the example of FIG. 5B, the support strap 106 runs from the anchor point 502 underneath the foot 504 (i.e., between the foot 504 and the foot plate 114) and wraps around the foot 504 on the opposing side from the anchor point 502. As is illustrated, the support strap 106 variant of FIG. 5A requires 1.21 times the load of the foot 504 "W" to support the foot 504. However, the support strap 106 variant of FIG. 5B only requires 0.35 times the load of the foot 504 "W" to support the foot 504. In other words, by anchoring the support strap 106 at anchor point 502 on one side of the foot 504, running the support strap 106 underneath the foot 504 (i.e., between the foot 504 and the foot plate 114), and running the support strap 106 around the foot 504 on the opposing side of the anchor point 502, approximately 30% of the force is required to support the foot 504 as compared with the example illustrated in FIG. 5A. In addition, the example of FIG. 5B provides additional comfort and support to the wearer as compared with the example of FIG. 5A. The principles described with reference to FIGS. 5A and 5B find utility in the embodiments set forth and described with reference to, for example, FIGS. 1A-1C, 2G-2I, 4A-4B, 10A-10F, and 10H-10L herein.

Figure 10A:
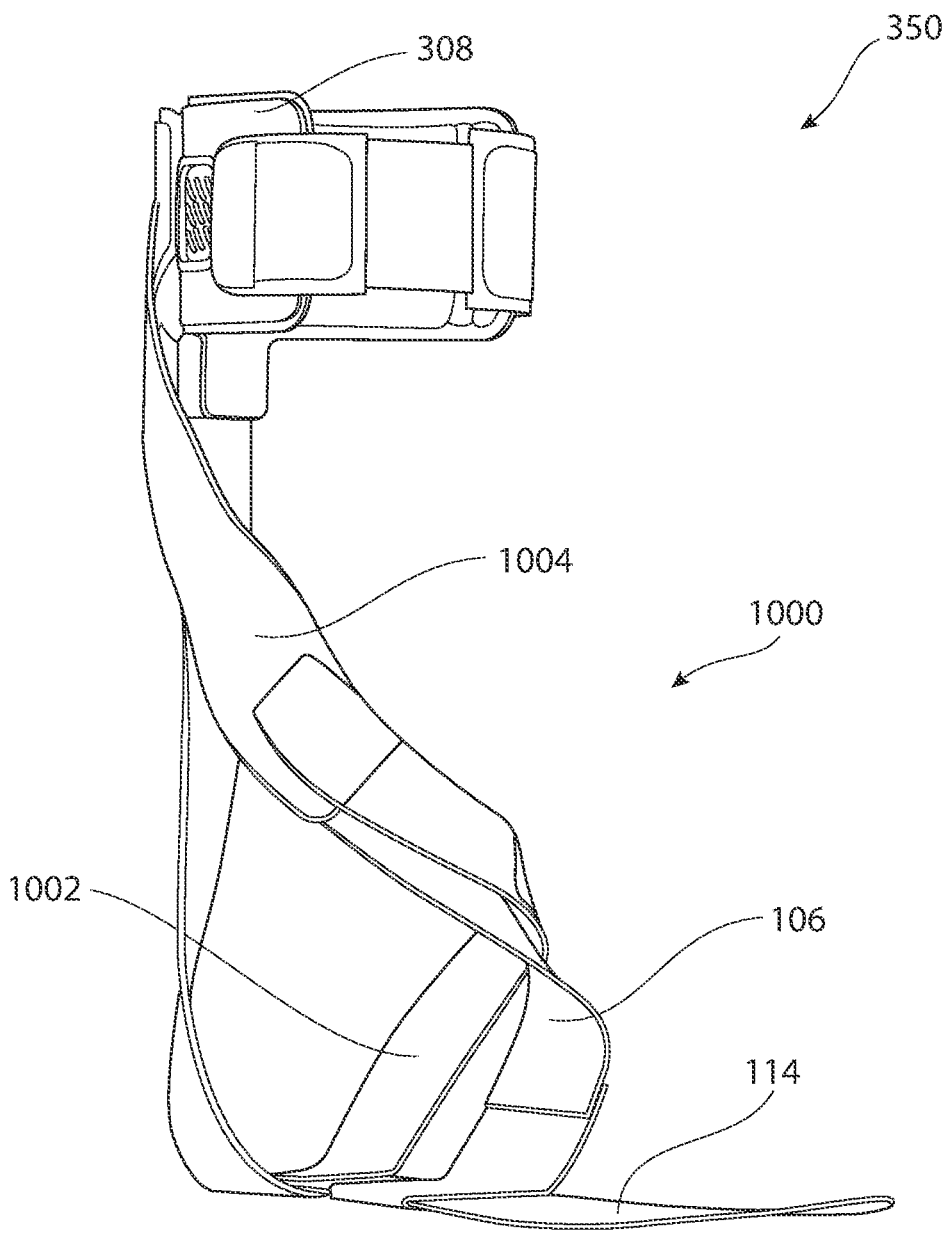
FIG. 10A is a perspective view of the AFO of FIGS. 3F-3J illustrating a configuration of a combination varus/valgus strap with a calcaneus strap, in accordance with the principles of the present disclosure.
Figure 10B:
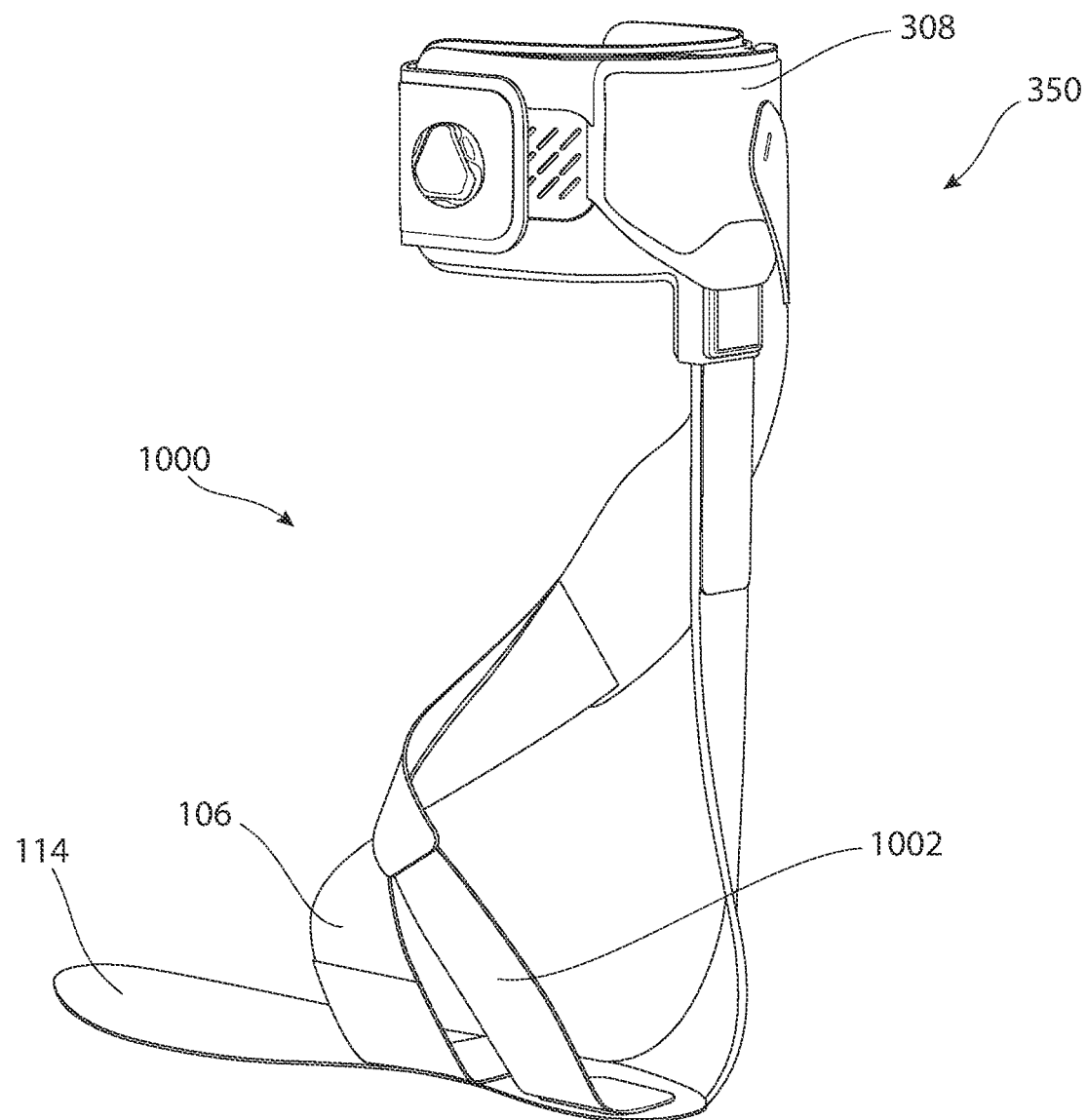
FIG. 10B is a perspective view of the AFO of FIG. 10A shown from a different perspective, in accordance with the principles of the present disclosure.
Figure 10C:
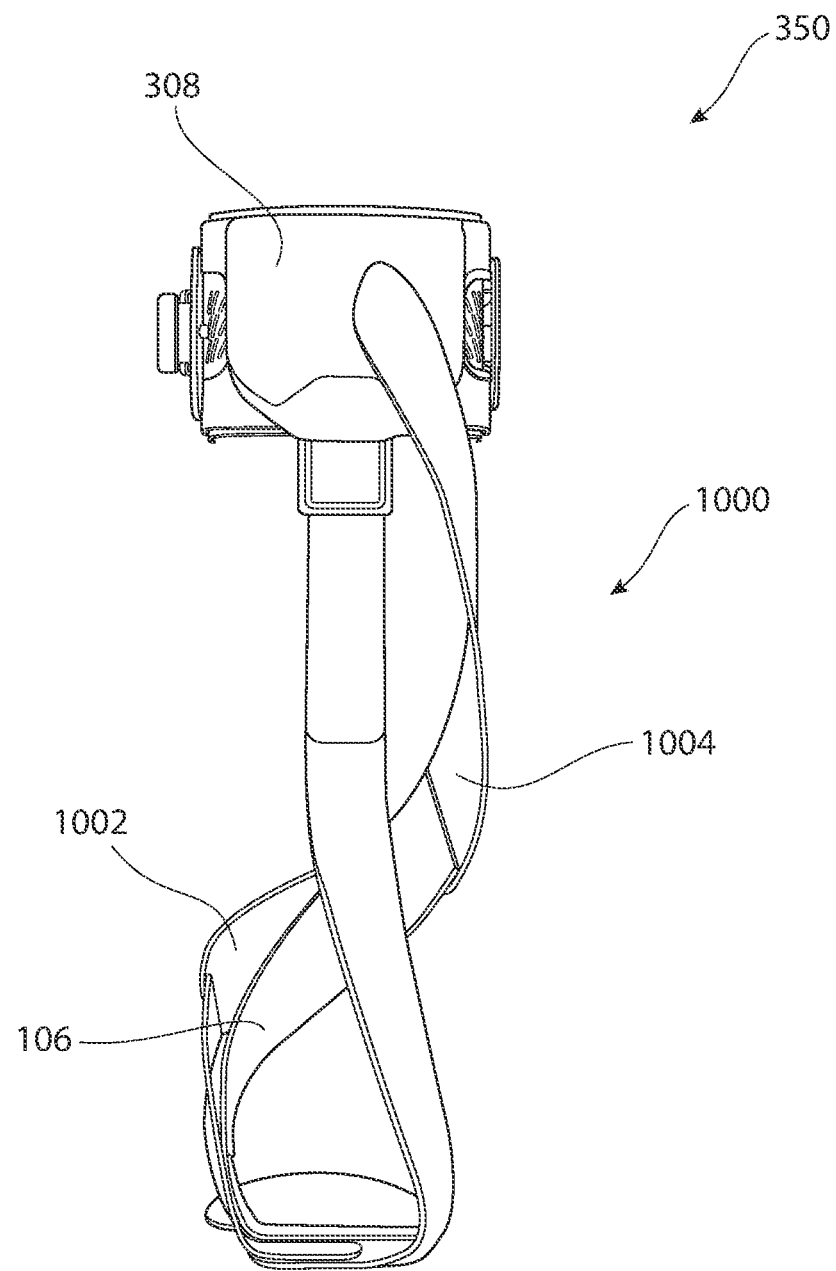
FIG. 10C is a back elevation view of the AFO of FIG. 10A, in accordance with the principles of the present disclosure.

Referring now to FIGS. 10A-10C, one exemplary strapping system 1000 is shown and described utilized in combination with a posterior AFO 350 such as that shown and described with reference to, for example, FIGS. 3E-3H. The strapping system 1000 includes a support strap 106 that is anchored to the foot plate 114 and positioned around the mid-foot region of the wearer of the posterior AFO 350. The anchoring of the support strap 106 to the foot plate 114 may be accomplished using, for example, a hook and loop fastener (e.g., Velcro®), epoxy and/or glue, and/or other suitable types of fasteners. The support strap 106 is intended to spiral around the wearer's leg and attached to the back of the cuff 308. The attachment point at the back of the cuff 308 may be, for example, a hook and loop fastener, a button (e.g., on support strap 106 or rear cuff 308) with a slot (e.g., on rear cuff 308 or support strap 106), and/or other suitable type of fastening mechanism. The strapping system 100 may also include a second support strap 1002 (e.g., a calcaneus strap). In some implementations, the second support strap 1002 is intended to be anchored to the foot plate 114 underneath the heel of the wearer of the posterior AFO 350. The anchoring of the second support strap 1002 to the foot plate 114 may be accomplished using, for example, a hook and loop fastener (e.g., Velcro®), epoxy and/or glue, and/or other suitable types of fasteners. The second support strap 1002 is intended to be secured at its opposing end to the support strap 106. Advantageously, this allows donning (and doffing) of the strapping system 1000 by attaching (or removing) of the support strap 106 at the back of the cuff 308. When secured, the strapping system 1000 may be considered dynamic in the sense that they tighten up when the foot of the wearer moves into plantar flexion (i.e., when the wearer requires the most support) and loosens when the foot goes into dorsiflexion. Additionally, at heel strike, the strapping system 1000 provides proprioceptive feedback underneath the foot of the wearer of the posterior AFO 350. The strapping system 1000 may also control instability of the foot by controlling the arch of the foot, especially for wearer's where their arch may tend to collapse and fall inwards as well their calcaneus going into a valgus position. For patients that may have more of a varus instability, the straps can be reversed to apply the opposite directional force as shown in, for example, FIG. 10L.

Figure 10D:
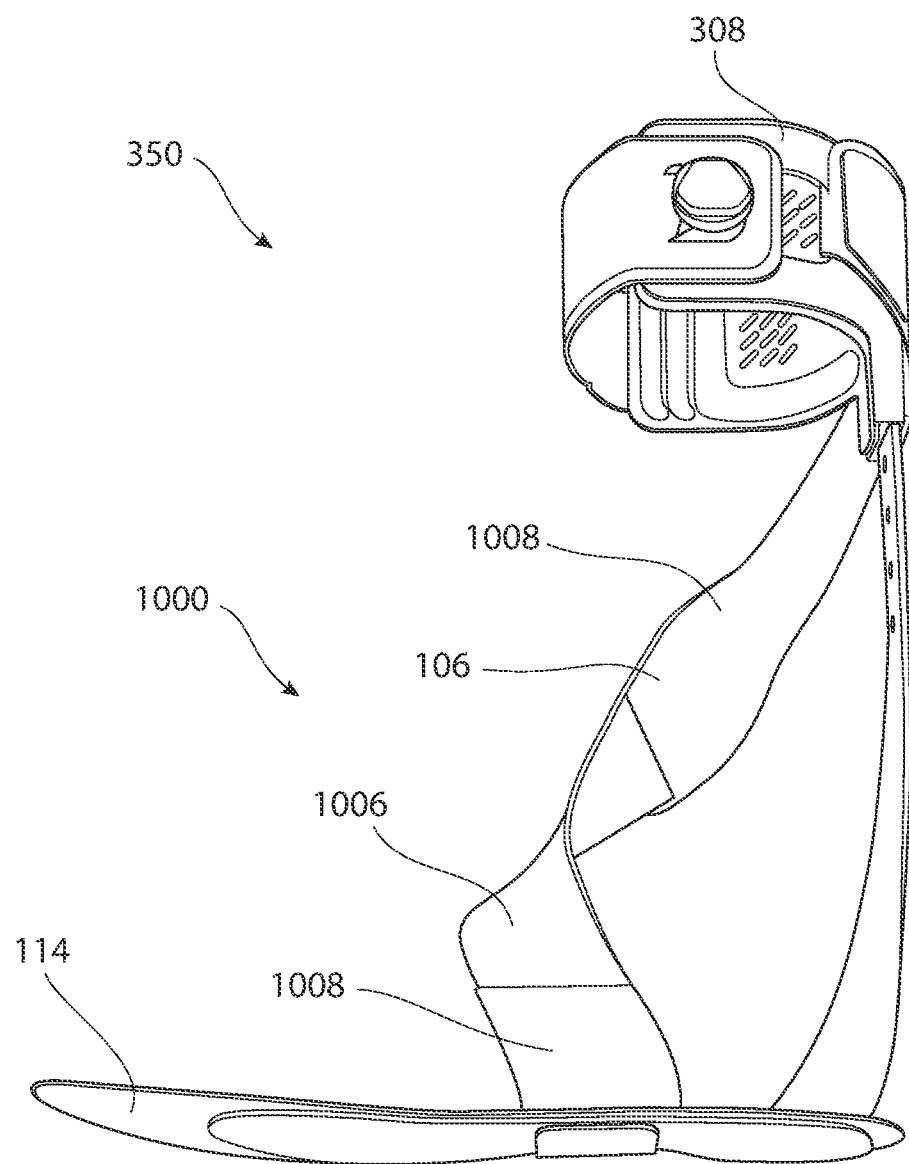
FIG. 10D is a perspective view of a variant of the AFO of FIG. 10A with a single varus/valgus strap that anchors underneath the footplate, crosses over the footplate to pick up the arch of the foot, spirals over the dorsum of the foot and up the leg to attach with the back of the calf, in accordance with the principles of the present disclosure.
Figure 10E:
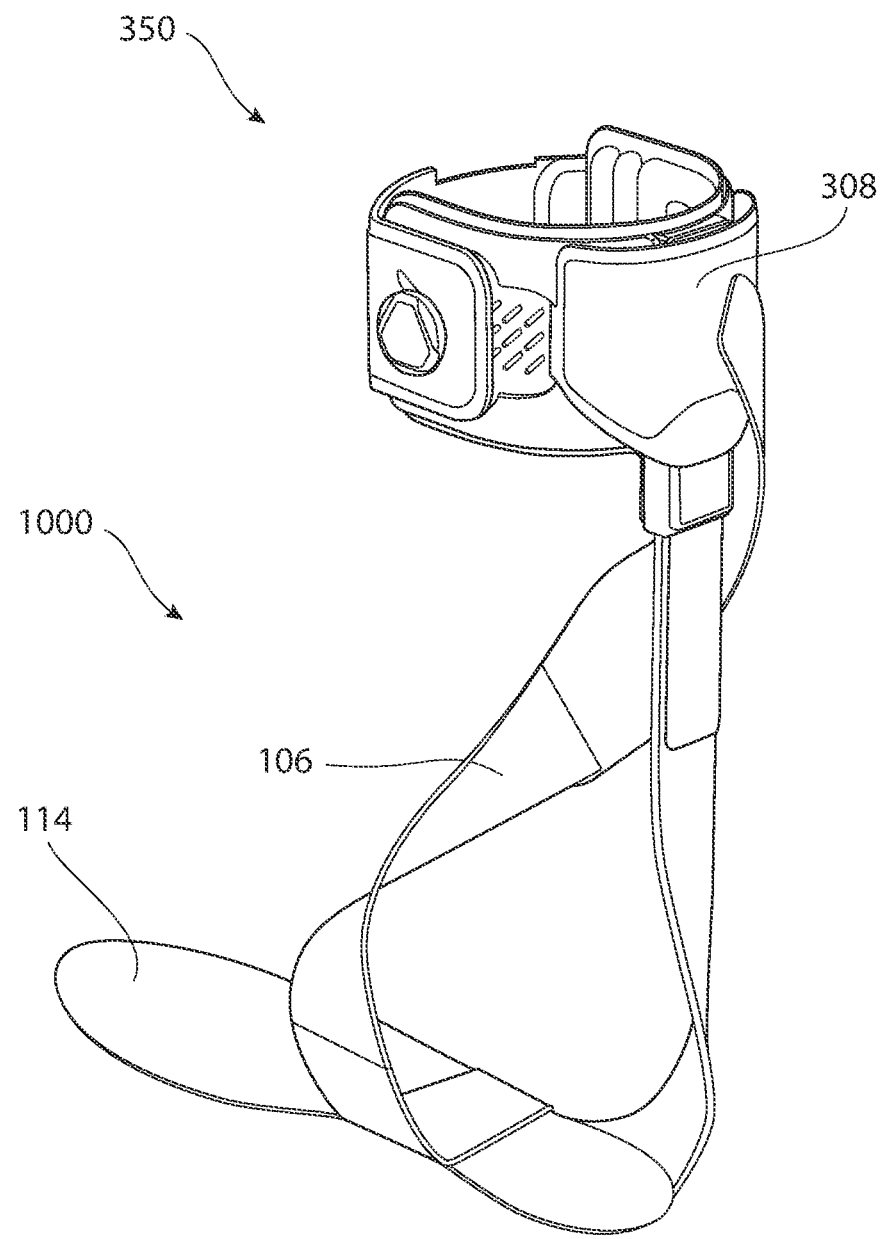
FIG. 10E is a rear perspective view of the AFO of FIG. 10D illustrating a different perspective, in accordance with the principles of the present disclosure.

Referring now to FIGS. 10D and 10E, a variant of the strapping system 1000 depicted in FIGS. 10A-10C is shown and described in detail. The strapping system 1000 depicted in FIGS. 10D and 10E includes a single support strap 106 that is intended for patients that do not have the same amount of instability as those patients intended for the strapping system 1000 of FIGS. 10A-10C. In other words, the patients intended for the strapping system of FIGS. 10D-10E do not require a second strap (e.g., a separate calcaneus strap). As depicted in FIG. 10D, the support strap 106 is anchored underneath the foot plate where it then wraps around the lateral part of the foot plate 114. As depicted in FIG. 10E, the support strap 106 wraps around the lateral part of the foot plate 114 and is intended to run along the top of the foot plate 114 underneath the wearer of the posterior AFO's foot. The support strap 106 is then intended to spiral around the patient's leg where it is secured to the cuff 308.

In some implementations, the support strap 106 may be constructed of two or more pieces of material with varying degrees of stretch. For example, one portion 1006 of the support strap 106 may have more (or less) stretch than a second portion 1008 of the support strap 106. As but one non-limiting example, portion 1008 of support strap 106 may have less stretch than portion 1006 of support strap to provide, inter alia, additional comfort for the wearer of the posterior AFO 350. As but another non-limiting example, portion 1008 may be constructed from a thinner material than portion 1006 of support strap 106. Such a variant may be desirable as the thinner material is less intrusive underneath the patient's foot, while providing adequate support in other areas of the support strap (e.g., portion 1006). In some implementations, the support strap 106 may be color-coded dependent upon the amount of elasticity and support that the support strap 106 provides. For example, one color (e.g., red) may provide a small amount of support, while another color (e.g., blue) may provide a large amount of support, while yet another color (e.g., yellow) may provide a level of support between the small amount of support and the large amount of support. Such a system may enable, for example, a treating physician to adapt the AFO 300/350 to suit a given patient's needs while minimizing the amount of inventory that needs to be stocked on-site. These and other variations would be readily apparent to one of ordinary skill given the contents of the present disclosure.

Figure 10F:
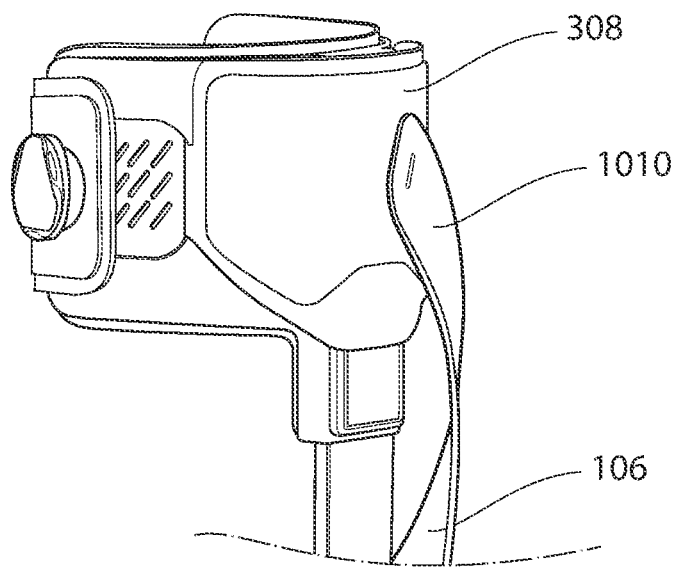
FIG. 10F is a close-up perspective view of the back of the calf piece of the AFO of FIG. 10D, in accordance with the principles of the present disclosure.
Figure 10G:
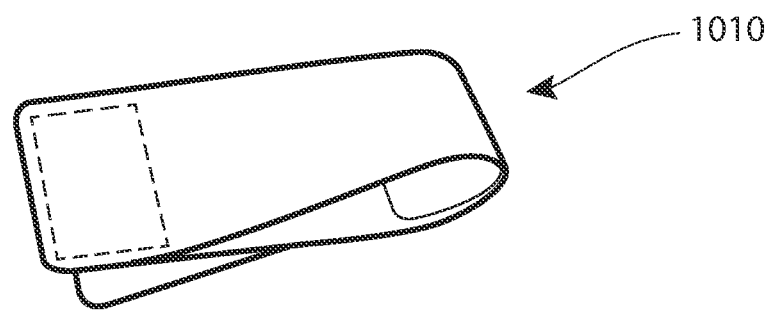
FIG. 10G is a perspective view of a thumb loop that can be applied to a varus/valgus strap, in accordance with the principles of the present disclosure.

Referring now to FIG. 10F, in some implementations the rear cuff 308 may include a hook and loop material that in combination hook and loop material on the end 1010 of the support strap 106 enables the support strap 106 to be conveniently secured to the rear cuff 308. Additionally, the area of the rear cuff 308 with the hook and loop fastener may occupy a relatively large area enabling the end 1010 of the support strap 106 to be secured medially on the rear cuff 308, laterally on the rear cuff 308, posteriorly on the rear cuff, or at some other position on the rear cuff 308. The relatively large area of hook and loop fastening material on the rear cuff 308 enables the wearer of the AFO to adjust the amount of support provided by the support strap 106 dependent upon, for example, the activity level of the wearer. While the embodiment depicted in FIG. 10F is described in the context of having the hook and loop fastener material on the rear cuff 308, it would be readily appreciated that other variants may include the hook and loop fastener material on the front cuff or on the front cuff and the rear cuff 308. FIG. 10G illustrates a variant of the support strap end 1010. In this variant, the support strap end 1010 may include a loop of material integrated into the end 1010 which facilitates attachment of the support strap 106 to the rear cuff/front cuff for patient's that may have, for example, grip weakness in one (or both) of their hands.

Figure 10H:
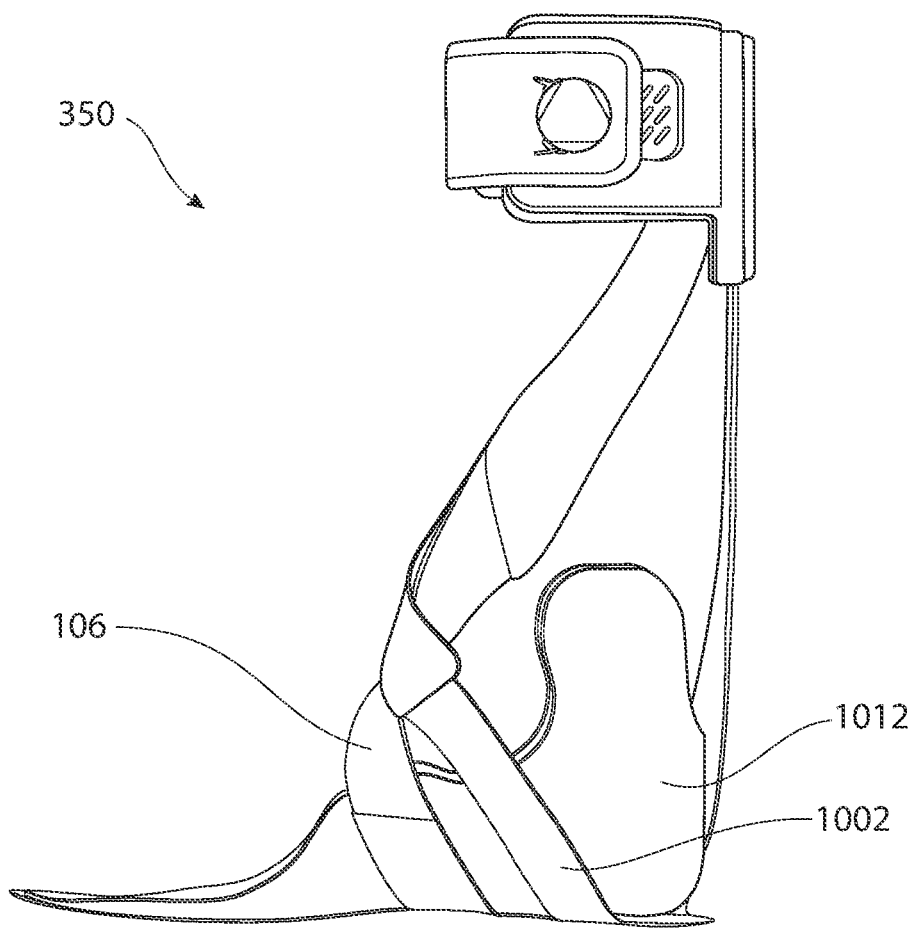
FIG. 10H is a side elevation view of the AFO of FIG. 10A with a supra malleolar orthotic (SMO) that is configured with a varus/valgus strap and a calcaneus strap, in accordance with the principles of the present disclosure.

Referring now to FIG. 10H, a posterior AFO 350 with a support strap 106, a second strap 1002, and a SMO 1012 is depicted. As a brief aside, an SMO is intended to support the foot just above the ankle bone or malleolus and are intended to maintain the heel of the wearer of the SMO in a neutral position while also supporting the arch of the foot. SMOs are typically manufactured from a semi-rigid polymer and due to the way it supports the foot, can irritate the skin/tissue surrounding the arch, instep, and/or bony areas of the foot/ankle. However, the SMO 1012 depicted in FIG. 10H may be manufactured from a relatively soft material as compared with traditional SMOs resultant from its use in combination with the support strap 106 and/or the second strap 1002. In other words, due to the additional support provided via use of the support strap 106 and/or the second strap 1002 of the AFO 350, a softer more pliable SMO 1012 may be utilized which can minimize irritation, while also fulfilling its function of supporting the arch of the foot.

Figure 10I:
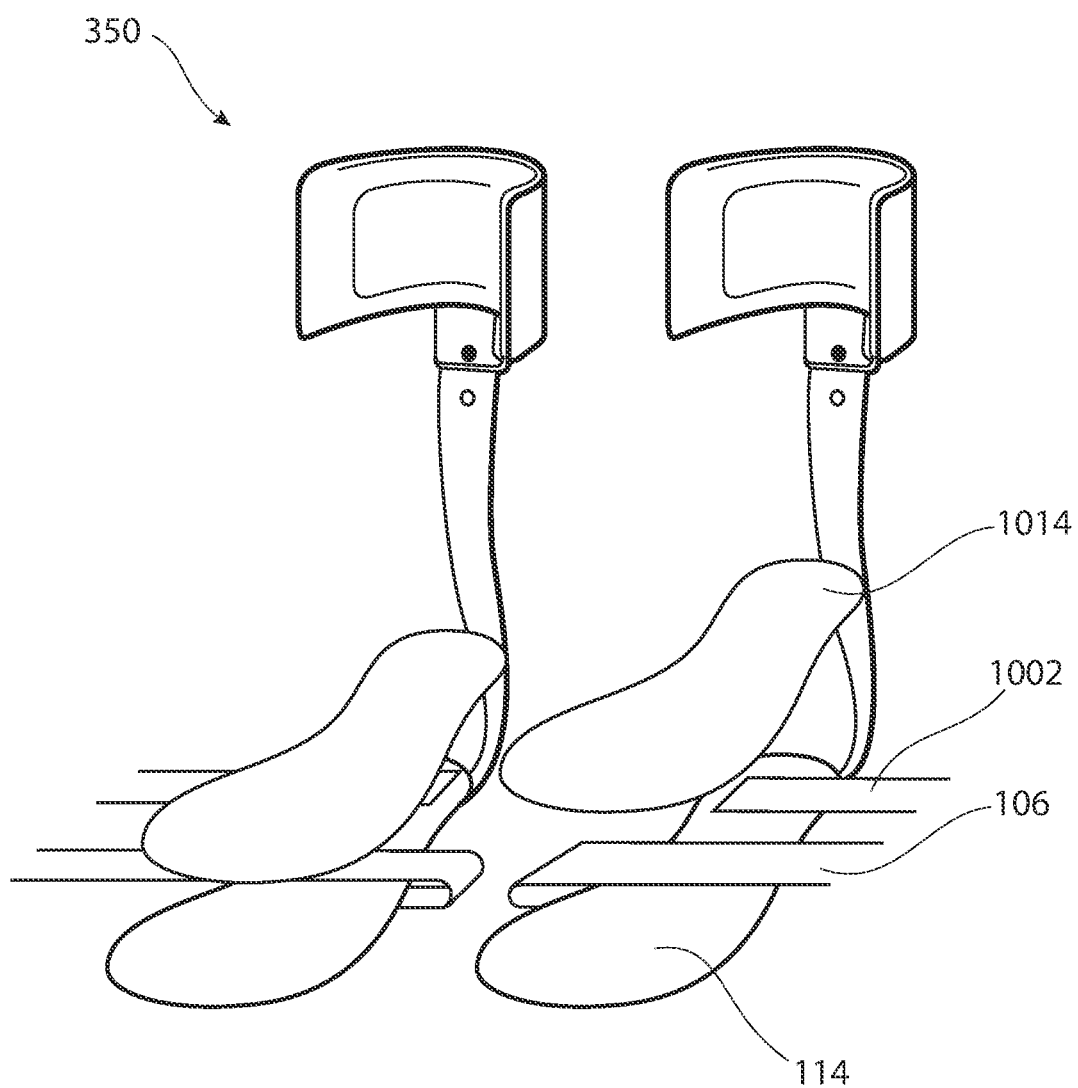
FIG. 10I is a front perspective view of a pair of the AFOs of FIG. 10A with an integrated insole that is configured to hold a varus/valgus strap and a calcaneus strap in place using hook and loop fasteners, in accordance with the principles of the present disclosure.

FIG. 10I illustrates a posterior AFO 350 variant which includes an insole 1014 in combination with the foot plate 114 and the support strap 106 and/or the second strap 1002. The insole 1014 may include slots on its underside (not shown) that are sized to accommodate the width of the support strap 106 and/or the second strap 1002. The insole 1014 may provide benefits by securing the position of the support strap 106 and/or the second strap 1002 when, for example, the patient inserts his foot into a shoe while wearing the AFO 350. The insole 1014 may also provide a flat surface for the wearer of the AFO 350, thereby minimizing discomfort associated with the support strap 106 and/or the second strap 1002 being placed between the foot of the patient and the foot plate 114 of the AFO 350. In the variant depicted in FIG. 10I, the insole 1014 may accommodate both varus and/or valgus deformity variants of the support strap 106 and/or the second strap 1002.

Figure 10J:
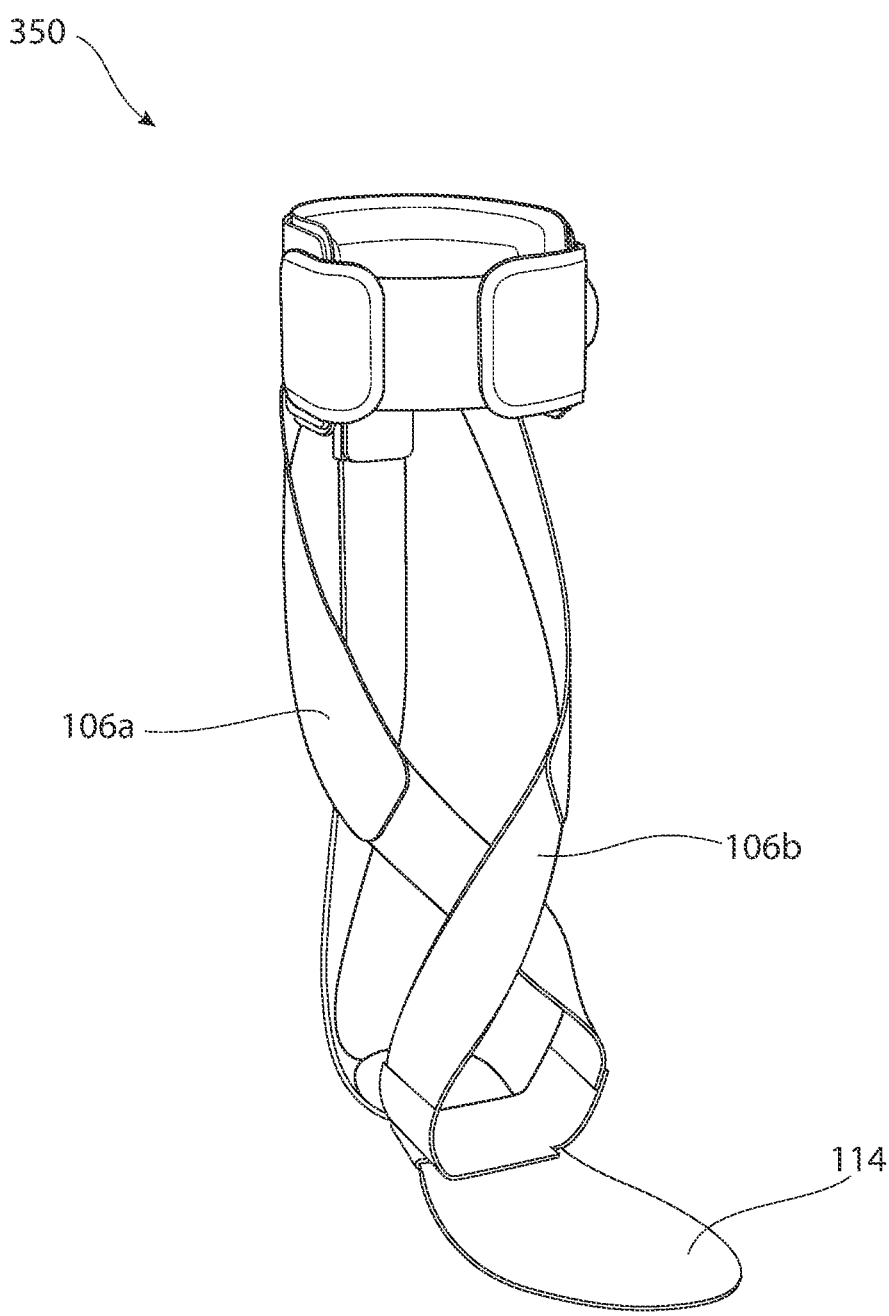
FIG. 10J is a perspective view of the AFO of FIG. 10A with a double varus/valgus strap configuration, in accordance with the principles of the present disclosure.
Figure 10K:
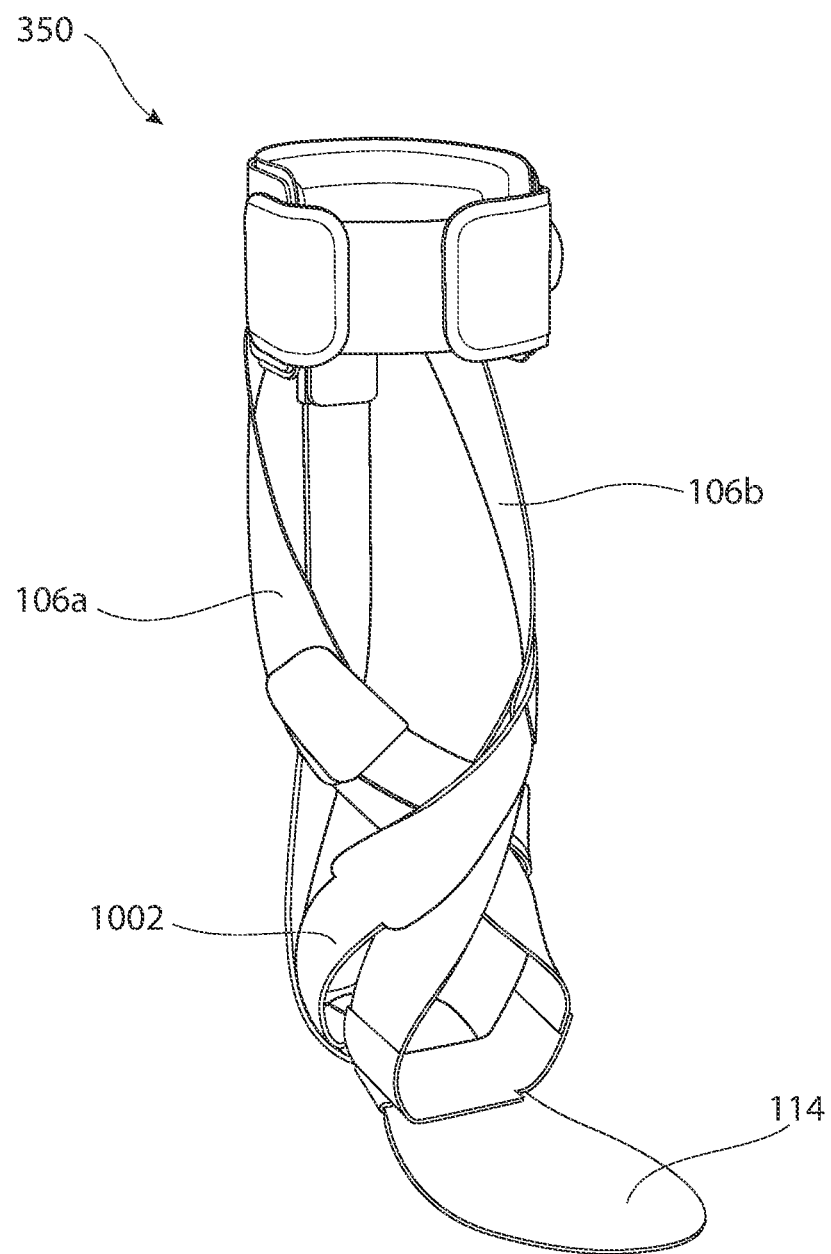
FIG. 10K is a perspective view of the AFO of FIG. 10J with a double varus/valgus strap and a double calcaneus strap configuration, in accordance with the principles of the present disclosure.

FIG. 10J illustrates a posterior AFO 350 variant in which two support straps 106 are utilized to provide both varus and valgus support for the wearer of the AFO 350. The interface of the support straps 106 to the foot plate 114 may be accomplished by having the width of the support straps 106 be halved at the portion of the support strap 106 that interfaces with the foot plate. For example, the portion of support strap 106a along the foot plate 114 may be half its width, while the portion of support strap 106b along the foot plate 114 may also be half its width. One portion of the support strap 106a on the foot plate 114 may be positioned in front of the other portion of the support strap 106b on the foot plate 114. In another variant, one or more slots may be incorporated into the support straps 106 adjacent to the foot plate. Accordingly, an end of support strap 106a can be inserted into a slot located on support strap 106b, with the end of support strap 106a being secured to the underside of the foot plate 114. Conversely, an end of support strap 106b can be inserted into a slot located on support strap 106a, with the end of support strap 106b being secured to the underside of the foot plate 114 opposite to the end of support strap 106a. FIG. 10K illustrates a variant of the embodiment illustrated in FIG. 10J with two secondary straps 1002 incorporated into the strapping system for the AFO 350. The attachment of the secondary straps 1002 to the foot plate 114 may be accomplished via similar means as described above with reference to FIG. 10J.

Figure 10L:
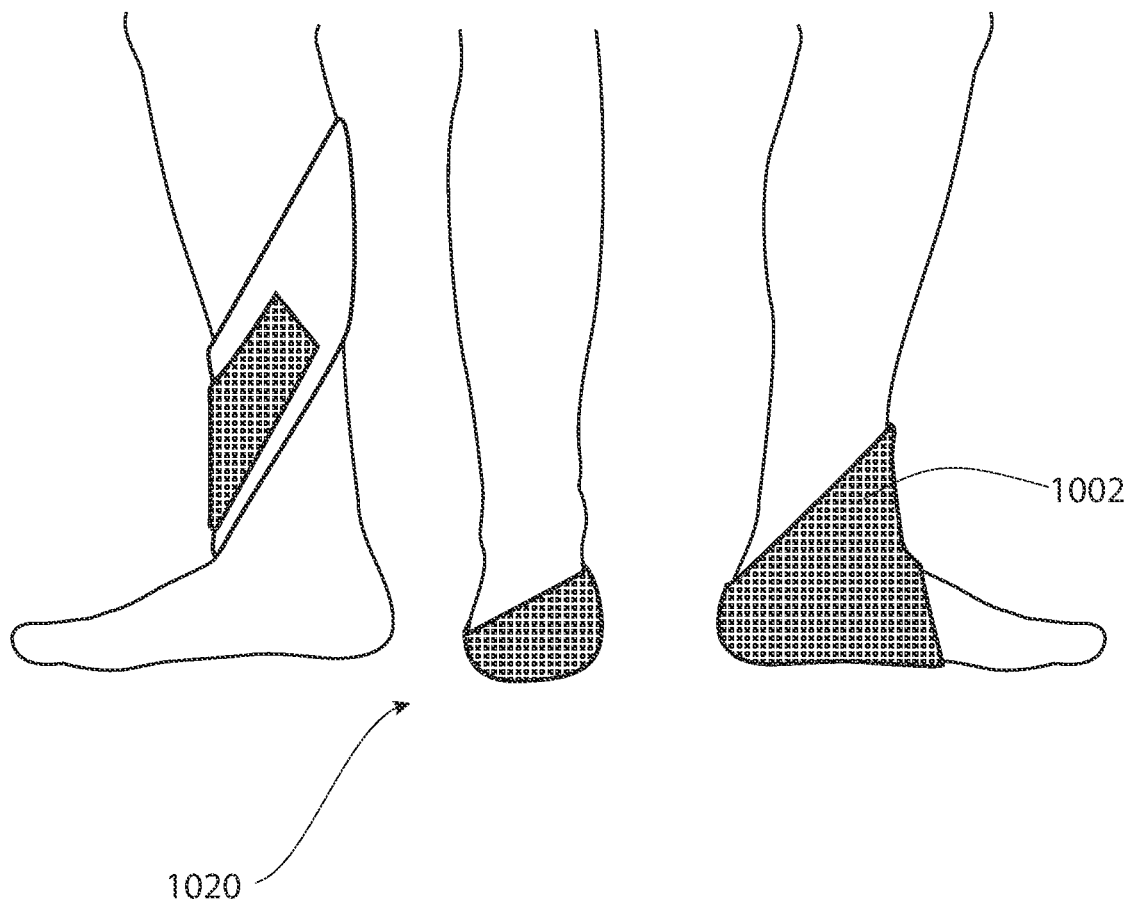
FIG. 10L is a multiple view illustration of a knitted varus/valgus strap where both straps have been integrated into one knitted structure that captures the entire footbed including the heel, in accordance with the principles of the present disclosure.
Figure 10M:
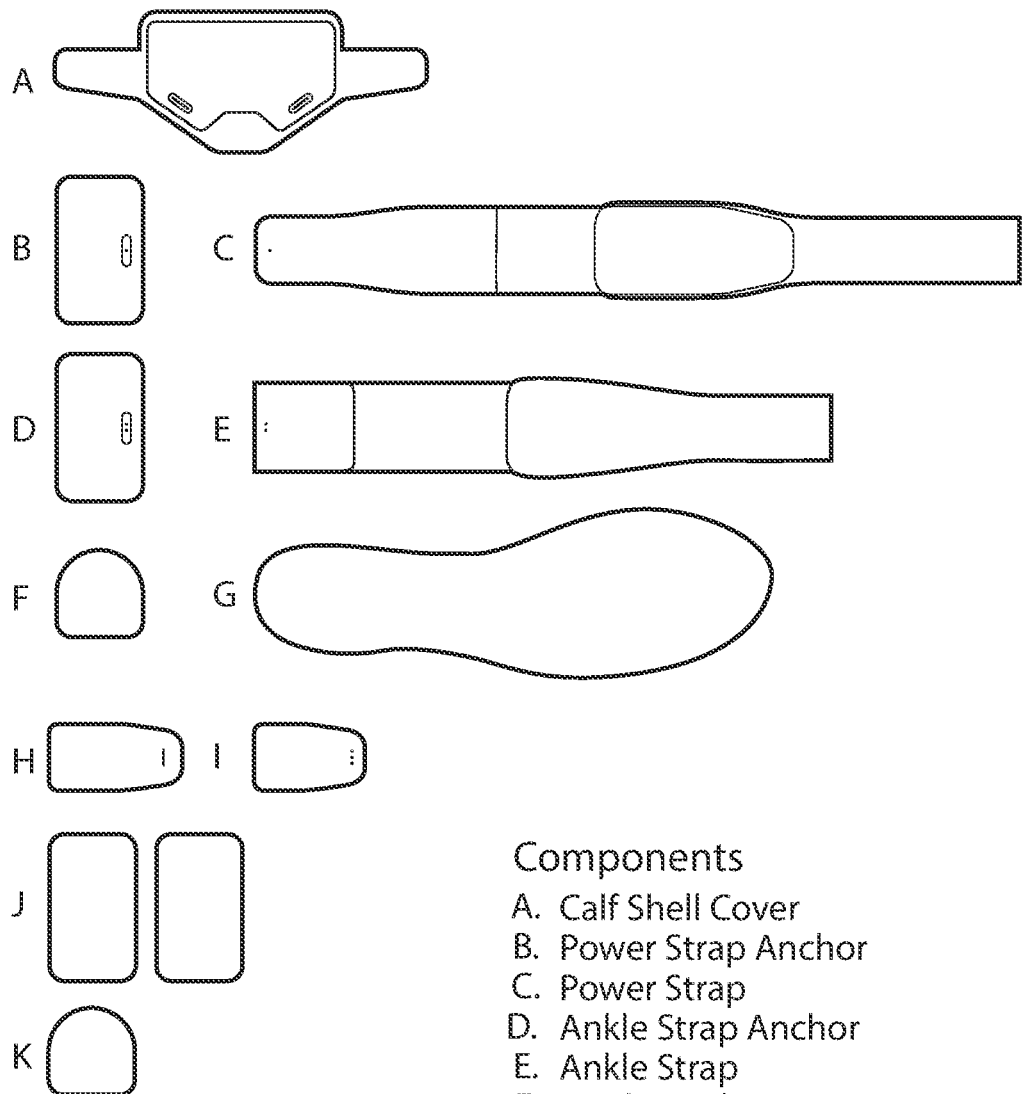
FIG. 10M is a perspective view of an AFO kit for an exemplary AFO device, in accordance with the principles of the present disclosure.

FIG. 10L illustrates an alternative implementation of the second strap 1002. The second strap 1002 is intended to be secured to the footplate 114. The second strap 1002 may be secured to the foot plate 114 on the medial side of the foot plate as depicted (or alternatively may be secured to the foot plate 114 on the lateral side of the foot plate 114). The second strap 1002 may be wrapped around the heel of the wearer so that the second strap 1002 encapsulates the heel, wrapped around the lateral (or medial side) of the foot, where it is ultimately secured to the support strap 106 or cuff of an AFO device. The alternative implementation of the second strap 1002 illustrated in FIG. 10L may be utilized in replacement of the second straps 1002 depicted in FIGS. 10A-10C, 10H, 10I, and 10K in some implementations. FIG. 10M depicts an exemplary parts list for an exemplary AFO kit.

Where certain elements of these implementations can be partially or fully implemented using known components, only those portions of such known components that are necessary for an understanding of the present disclosure are described, and detailed descriptions of other portions of such known components are omitted so as not to obscure the disclosure.

In the present specification, an implementation showing a singular component should not be considered limiting; rather, the disclosure is intended to encompass other implementations including a plurality of the same component, and vice versa, unless explicitly stated otherwise herein.

Further, the present disclosure encompasses present and future known equivalents to the components referred to herein by way of illustration.

It will be recognized that while certain aspects of the technology are described in terms of a specific sequence of steps of a method, these descriptions are only illustrative of the broader methods of the disclosure and may be modified as required by the particular application. Certain steps may be rendered unnecessary or optional under certain circumstances. Additionally, certain steps or functionality may be added to the disclosed implementations, or the order of performance of two or more steps permuted. All such variations are considered to be encompassed within the disclosure disclosed and claimed herein.

While the above detailed description has shown, described, and pointed out novel features of the disclosure as applied to various implementations, it will be understood that various omissions, substitutions, and changes in the form and details of the device or process illustrated may be made by those skilled in the art without departing from the disclosure. The foregoing description is of the best mode presently contemplated of carrying out the principles of the disclosure. This description is in no way meant to be limiting, but rather should be taken as illustrative of the general principles of the technology. The scope of the disclosure should be determined with reference to the claims.

What is claimed:

1. A method of manufacturing an ankle foot orthosis (AFO), comprising:
    acquiring a pre-impregnated carbon fiber sheet of material;
    cutting the pre-impregnated carbon fiber sheet of material to a desired shape;
    inserting the cut pre-impregnated carbon fiber sheet of material into a multi-piece mold, the multi-piece mold manufactured from a metallic material;
    compressing the multi-piece mold with the inserted and cut pre-impregnated carbon fiber sheet of material disposed therein;
    heating the multi-piece mold so as to activate resin within the cut pre-impregnated carbon fiber sheet of material; and
    removing the activated cut pre-impregnated carbon fiber sheet of material from the multi-piece mold.

2. The method of claim 1, wherein individual strands of the cut pre-impregnated carbon fiber sheet are greater than one hundred and twenty-six millimeters (126 mm) in length.

3. The method of claim 2, wherein the individual strands of the cut pre-impregnated carbon fiber sheet are greater than one hundred and sixty millimeters (160 mm) in length.

4. The method of claim 2, wherein the multi-piece mold includes a cavity to form a transition portion and an adjustable portion of an ankle foot orthosis (AFO) strut and the method further comprises placing the cut pre-impregnated carbon fiber sheet into the multi-piece mold such that the individual strands of the cut pre-impregnated carbon fiber sheet are present within each of the transition portion and the adjustable portion of the AFO strut as well as a foot plate portion of the AFO.

5. The method of claim 1, wherein the compressing of the multi-piece mold with the inserted and cut pre-impregnated carbon fiber sheet of material disposed therein further comprises:
    forming a foot plate comprising a trimmable portion and a non-trimmable portion; and
    forming a spiral strut coupled with the foot plate.

6. The method of claim 5, wherein the forming of the spiral strut coupled with the foot plate further comprises forming the spiral strut such that the spiral strut is coupled with a hindfoot region of the foot plate laterally of a mid-line of the foot plate at an interface region.

7. The method of claim 6, wherein the forming of the spiral strut further comprises forming a transition portion for the spiral strut that spirals approximately sixty-five degrees (65°) over less than one-hundred sixty millimeters (160 mm) in height from a bottom surface of the foot plate.

8. The method of claim 5, further comprising forming the trimmable portion of the foot plate such that the trimmable portion of the foot plate is located in both a hindfoot region of the foot plate as well as portions anterior to the hindfoot region of the foot plate.

9. The method of claim 5, wherein the forming of the foot plate further comprises forming the foot plate such that the trimmable portion of the foot plate shares a common surface with the non-trimmable portion of the foot plate and the non-trimmable portion of the foot plate extends below the trimmable portion of the foot plate and wherein a concaved junction is disposed on at least a portion of an interface between the trimmable portion and the non-trimmable portion.

10. The method of claim 5, wherein the forming of the spiral strut coupled with the foot plate further comprises forming the spiral strut such that the spiral strut is coupled with a hindfoot region of the foot plate lateral of a mid-line of the foot plate at an interface region, the spiral strut comprising a transition portion that spirals approximately sixty-five degrees (65°) over less than one-hundred sixty millimeters (160 mm) in height.

11. The method of claim 10, wherein the trimmable portion of the foot plate is located in both a hindfoot region of the foot plate as well as portions anterior to the hindfoot region of the foot plate.

12. The method of claim 11, wherein the trimmable portion located in portions anterior to the hindfoot region of the foot plate enables an overall length of the foot plate to be trimmed by approximately sixty millimeters (60 mm).

13. The method of claim 12, wherein the trimmable portion of the foot plate enables an overall length of the foot plate to be trimmed by greater than seventy-five millimeters (75 mm).

14. The method of claim 12, wherein the trimmable portion of the foot plate shares a common surface with the non-trimmable portion of the foot plate and the non-trimmable portion of the foot plate extends below the trimmable portion of the foot plate and wherein a concaved junction is disposed on at least a portion of an interface between the trimmable portion and the non-trimmable portion.

15. The method of claim 10, wherein the forming of the transition portion of the spiral strut further comprises forming a curved surface that transitions towards a flat surface of the spiral strut.

16. The method of claim 15, wherein an adjustable portion of the spiral strut comprises the flat surface, the flat surface enabling an adjusting of an overall height of the AFO to vary between three hundred and twenty millimeters (320 mm) and three hundred and sixty-five millimeters (365 mm).

17. The method of claim 16, wherein the flat surface of the adjustable portion of the spiral strut enables an adjusting of an overall height of the AFO to vary between two hundred and ninety-five (295 mm) and three hundred and eighty-four millimeters (384 mm).

18. A method of manufacturing an ankle foot orthosis (AFO), comprising:
    acquiring a pre-impregnated fiber sheet of material;
    cutting the pre-impregnated fiber sheet of material to a desired shape;
    inserting the cut pre-impregnated fiber sheet of material into a multi-piece mold, the multi-piece mold manufactured from a metallic material;
    compressing the multi-piece mold with the inserted and cut pre-impregnated fiber sheet of material disposed therein;
    heating the multi-piece mold so as to activate resin within the cut pre-impregnated fiber sheet of material; and removing the activated cut pre-impregnated fiber sheet of material from the multi-piece mold.

19. The method of claim 18, wherein the compressing of the multi-piece mold with the inserted and cut pre-impregnated fiber sheet of material disposed therein further comprises:
   forming a foot plate comprising a trimmable portion and a non-trimmable portion; and
   forming a spiral strut coupled with the foot plate.

20. The method of claim 19, wherein the forming of the spiral strut coupled with the foot plate further comprises forming the spiral strut such that the spiral strut is coupled with a hindfoot region of the foot plate laterally of a mid-line of the foot plate at an interface region.

* * * * *